United States Patent
Cepko et al.

(10) Patent No.: US 11,827,926 B2
(45) Date of Patent: Nov. 28, 2023

(54) METHODS AND COMPOSITIONS FOR THE DIAGNOSIS AND TREATMENT OF COVID 19

(71) Applicant: PRESIDENT AND FELLOWS OF HARVARD COLLEGE, Cambridge, MA (US)

(72) Inventors: Constance L. Cepko, Boston, MA (US); Brian Anthony Rabe, Boston, MA (US)

(73) Assignee: PRESIDENT AND FELLOWS OF HARVARD COLLEGE

( * ) Notice: Subject to any disclaimer, the term of this patent is extended or adjusted under 35 U.S.C. 154(b) by 100 days.

(21) Appl. No.: 17/209,985

(22) Filed: Mar. 23, 2021

(65) Prior Publication Data

US 2021/0310060 A1   Oct. 7, 2021

Related U.S. Application Data

(60) Provisional application No. 63/001,935, filed on Mar. 30, 2020, provisional application No. 62/993,423, filed on Mar. 23, 2020.

(51) Int. Cl.
*C12Q 1/6853* (2018.01)
*C12Q 1/70* (2006.01)

(52) U.S. Cl.
CPC .......... *C12Q 1/6853* (2013.01); *C12Q 1/701* (2013.01)

(58) Field of Classification Search
None
See application file for complete search history.

(56) References Cited

U.S. PATENT DOCUMENTS

| | | | |
|---|---|---|---|
| 3,687,808 | A | 8/1972 | Merigan et al. |
| 7,423,142 | B2 | 9/2008 | Vornlocher et al. |
| 8,710,200 | B2 | 4/2014 | Schrum et al. |
| 9,074,249 | B2 | 7/2015 | Tanner et al. |
| 9,580,748 | B2 | 2/2017 | Tanner et al. |
| 10,253,357 | B2 | 4/2019 | Mitra et al. |
| 10,968,493 | B1 * | 4/2021 | Tanner ................ C12Q 1/6844 |
| 2012/0003630 | A1 | 1/2012 | Collins et al. |
| 2016/0367702 | A1 | 12/2016 | Hoge et al. |
| 2019/0060458 | A1 | 2/2019 | De Fougerolles |

OTHER PUBLICATIONS

Boom et al., "Rapid and simple method for purification of nucleic acids." Journal of clinical microbiology 28.3: 495-503 (1990).
Calvert et al., "Rapid colorimetric detection of Zika virus from serum and urine specimens by reverse transcription loop-mediated isothermal amplification (RT-LAMP)." PloS one 12.9: e0185340 (2017).
CDC, Interim Guidelines for Collecting, Handling, and Testing Clinical Specimens from Persons for Coronavirus Disease 2019 (COVID-19) (Mar. 19, 2020).
Englisch et al., "Chemically modified oligonucleotides as probes and inhibitors." Angewandte Chemie International Edition in English 30.6: 613-629 (1991).
Gill et al., "Nucleic acid isothermal amplification technologies—a review." Nucleosides, Nucleotides and Nucleic Acids 27.3: 224-243 (2008).
Hardinge et al., "Reduced false positives and improved reporting of loop-mediated isothermal amplification using quenched fluorescent primers." Scientific reports 9.1: 7400 (2019).
Kim et al., "Isothermal DNA amplification in bioanalysis: strategies and applications." Bioanalysis 3.2: 227-239 (2011).
Levesque-Sergerie et al., "Detection limits of several commercial reverse transcriptase enzymes: impact on the low-and high-abundance transcript levels assessed by quantitative RT-PCR." BMC molecular biology 8.1: 93 (2007).
Nagamine, et al. "Loop-mediated isothermal amplification reaction using a nondenatured template." Clinical chemistry 47.9: 1742-1743 (2001).
Nagamine et al., "Accelerated reaction by loop-mediated isothermal amplification using loop primers." Molecular and cellular probes 16.3: 223-229 (2002).
New England Biolabs, "Isothermal Amplification" Available on the world wide web at: www.neb.com/applications/dna-amplification-pcr-and-qpcr/isothermal-amplification (accessed by Web Archive on Jul. 13, 2017).
New England Biolabs, "WarmStart Colorimetric LAMP 2X Master Mix Typical LAMP Protocol (M1800)." Available on the world wide web at: www.neb.com/protocols/2016/08/15/warmstart-colorimetric-lamp-2x-master-mix-typical-lamp-protocol-m1800 (2016b).
New England Biolabs, "WarmStart LAMP Kit (DNA & RNA) Protocol (E1700)." Available on the world wide web at: www.neb.com/protocols/2016/08/15/warmstart-lamp-kit-dna-rna-protocol-e1700 (2016a).
Notomi et al., "Loop-mediated isothermal amplification of DNA." Nucleic Acids Res. 28(12): E63 (2000).
Notomi et al., "Loop-mediated isothermal amplification (LAMP): principle, features, and future prospects." Journal of microbiology 53.1: 1-5 (2015).
Okello et al., "Quantitative assessment of the sensitivity of various commercial reverse transcriptases based on armored HIV RNA." PLoS one 5.11: e13931 (2010).
Poole et al., "Colorimetric tests for diagnosis of filarial infection and vector surveillance using non-instrumented nucleic acid loop-mediated isothermal amplification (NINA-LAMP)." PloS one 12.2: e0169011 (2017).
Tomita et al., "Loop-mediated isothermal amplification (LAMP) of gene sequences and simple visual detection of products." Nature protocols 3.5: 877-882 (2008).
Torres et al., "LAVA: an open-source approach to designing LAMP (loop-mediated isothermal amplification) DNA signatures." BMC bioinformatics 12: 240 (2011).
Yan et al., "Isothermal amplified detection of DNA and RNA." Molecular BioSystems 10.5: 970-1003 (2014).

(Continued)

*Primary Examiner* — Samuel C Woolwine
*Assistant Examiner* — Carolyn L Greene
(74) *Attorney, Agent, or Firm* — NIXON PEABODY LLP; David S. Resnick; Alissa R. Young

(57) ABSTRACT

Described herein are methods and compositions related to the diagnosis and treatment of COVID 19 and the detection of SARS-Cov-2.

20 Claims, 45 Drawing Sheets
Specification includes a Sequence Listing.

(56) References Cited

OTHER PUBLICATIONS

Zhang et al., "Rapid molecular detection of SARS-CoV-2 (COVID-19) virus RNA using colorimetric LAMP." MedRxiv: Feb. 29, 2020 (2020) (available on the world wide web at https://www.medrxiv.org/content/10.1101/2020.02.26.20028373v1).

* cited by examiner

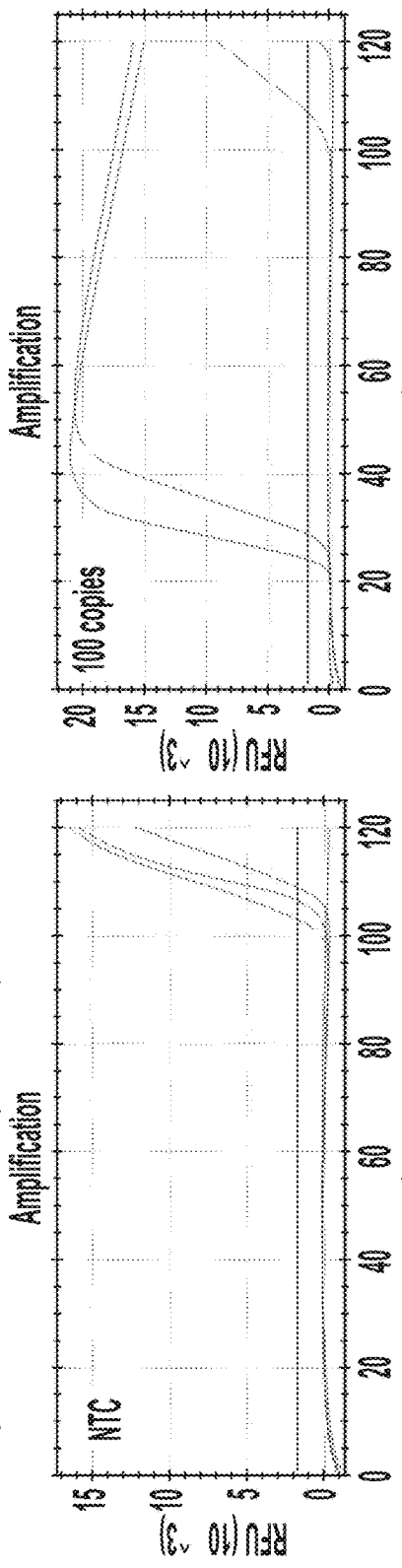
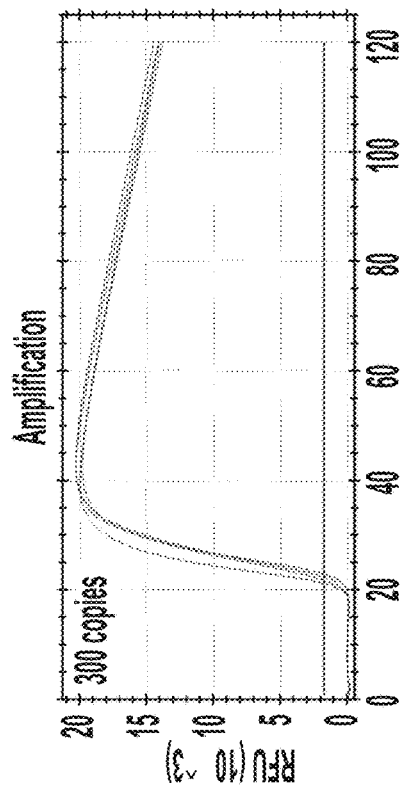
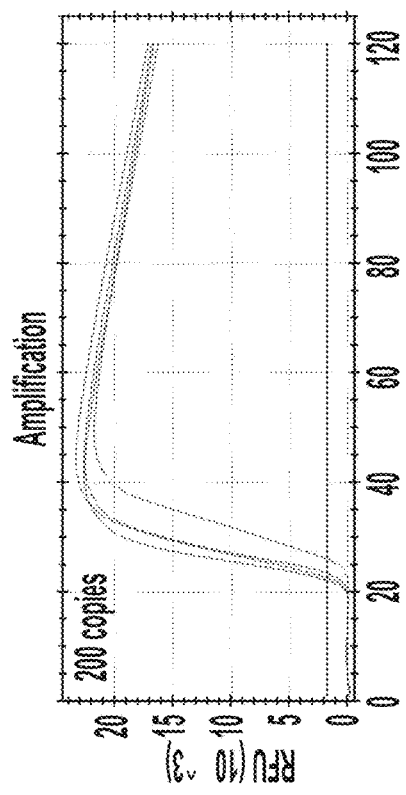
FIG. 3A  FIG. 3B  FIG. 3C  FIG. 3D

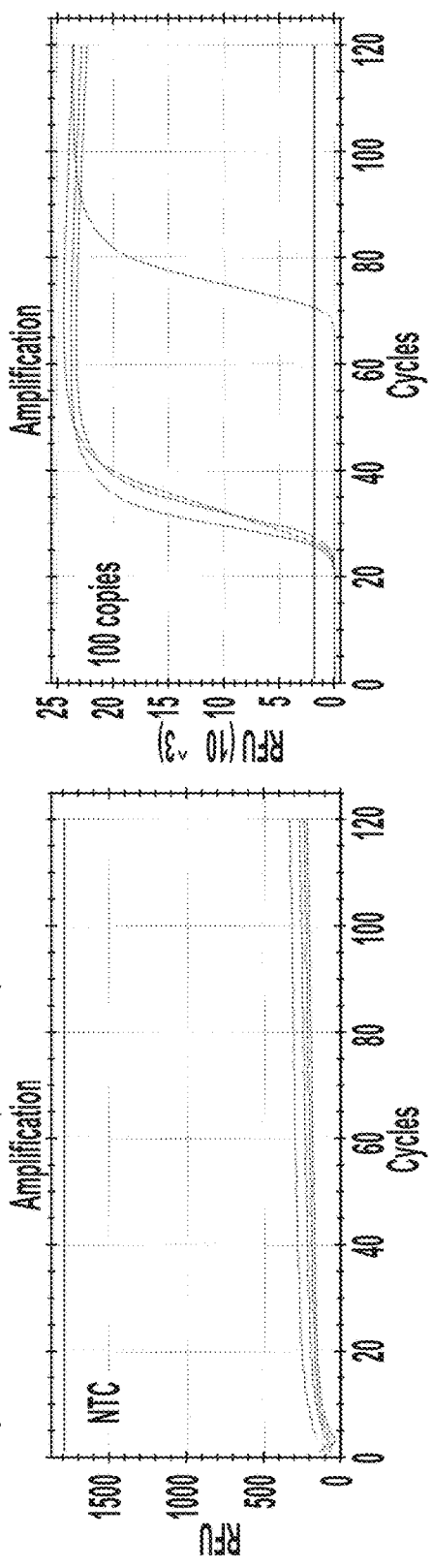
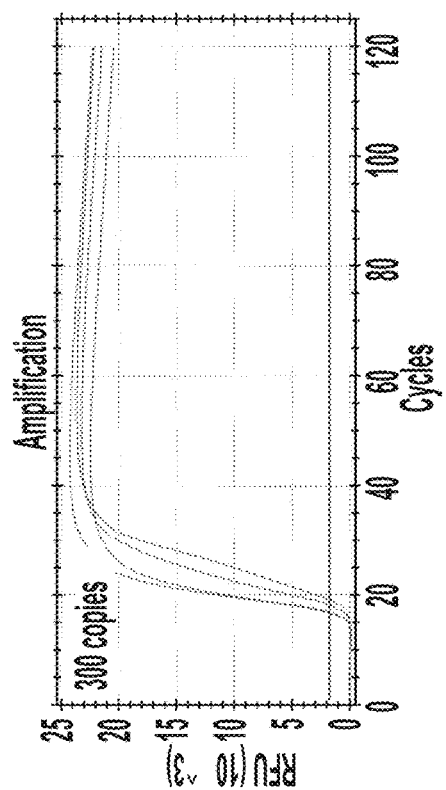
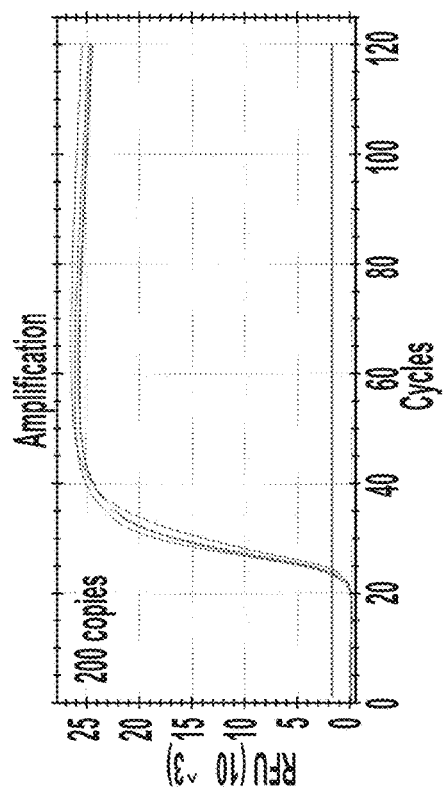
FIG. 4A  FIG. 4B  FIG. 4C  FIG. 4D

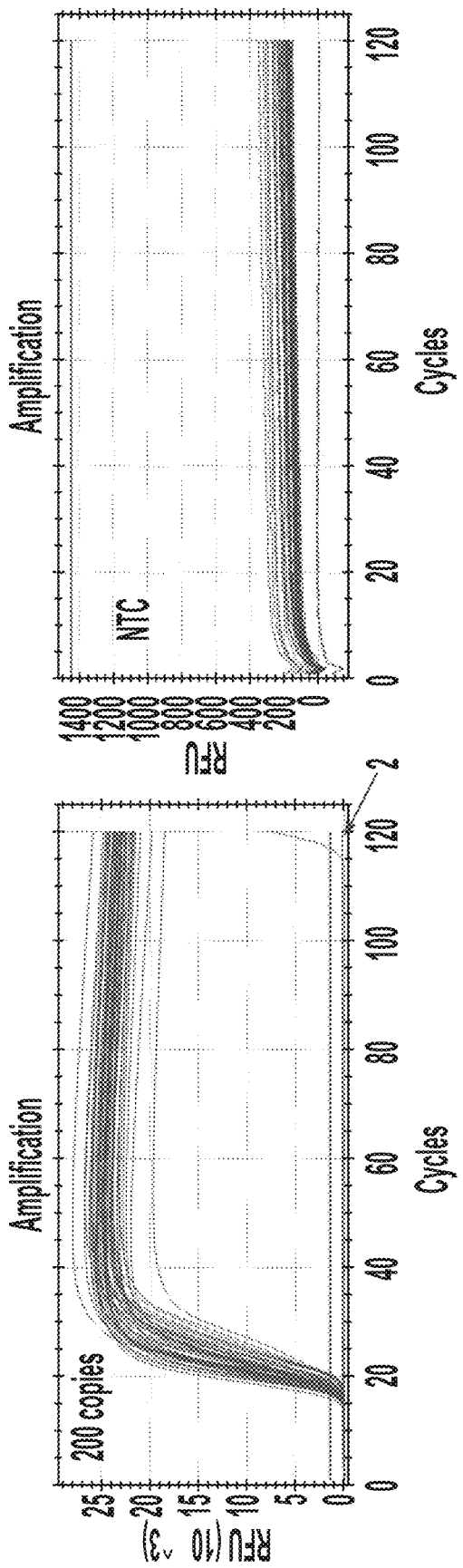

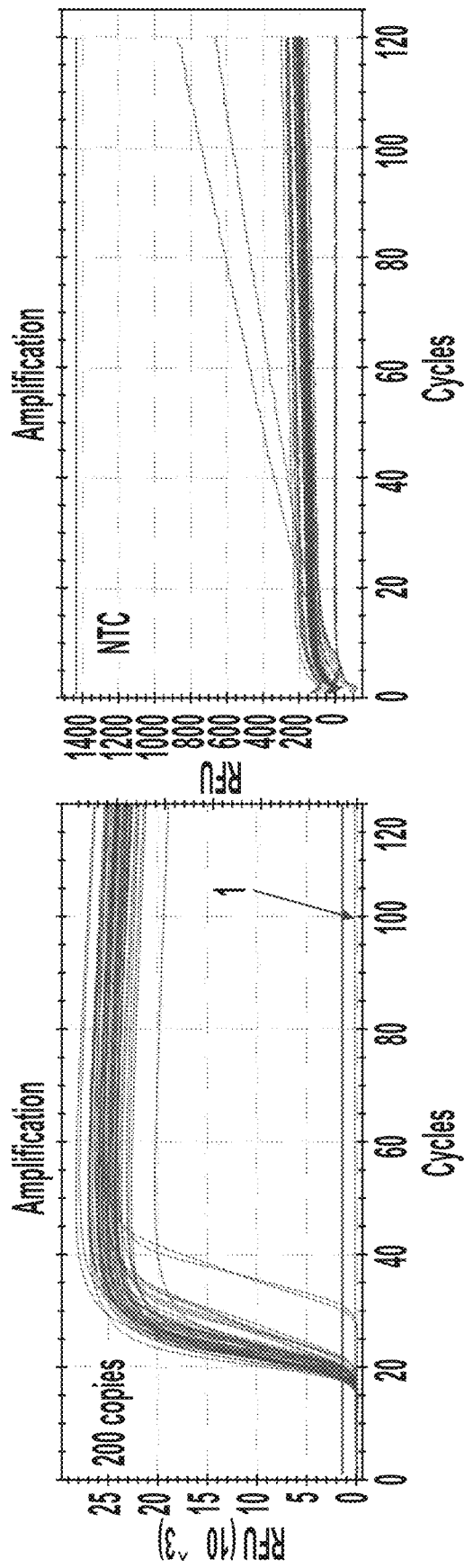

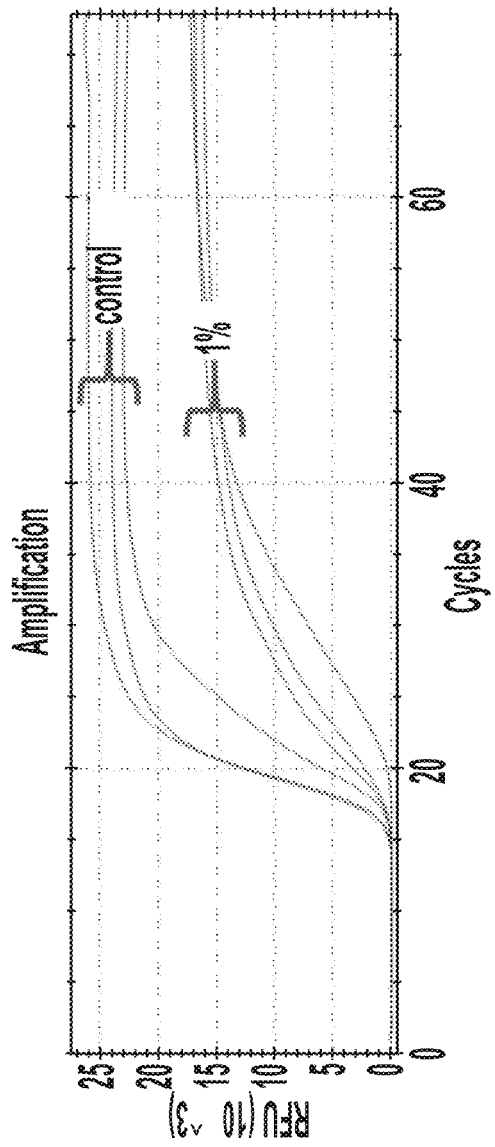

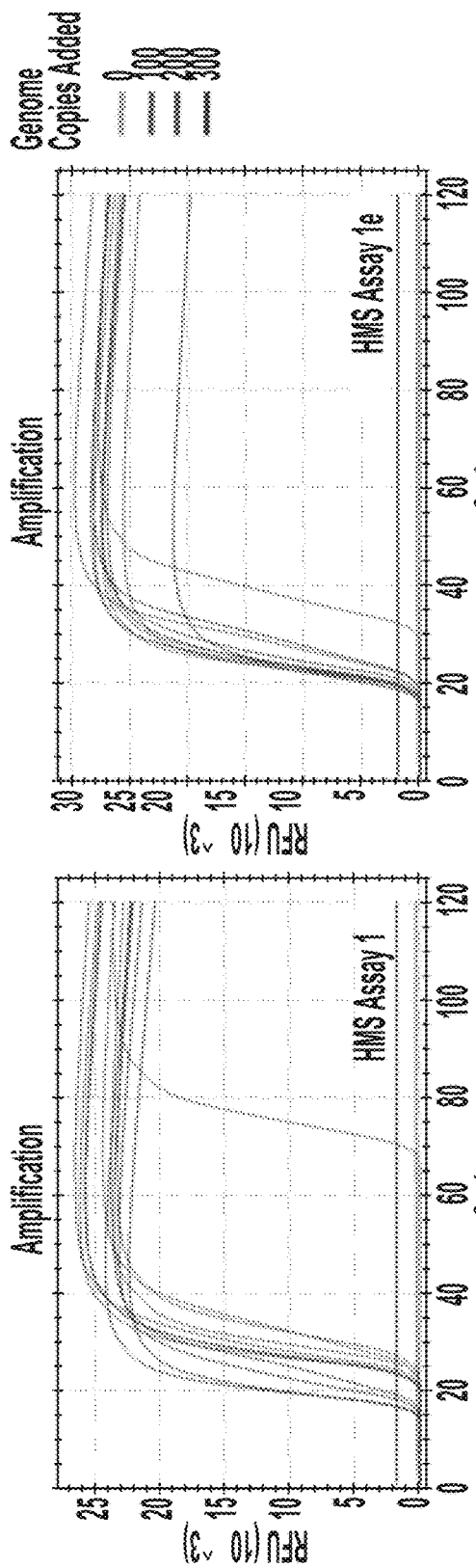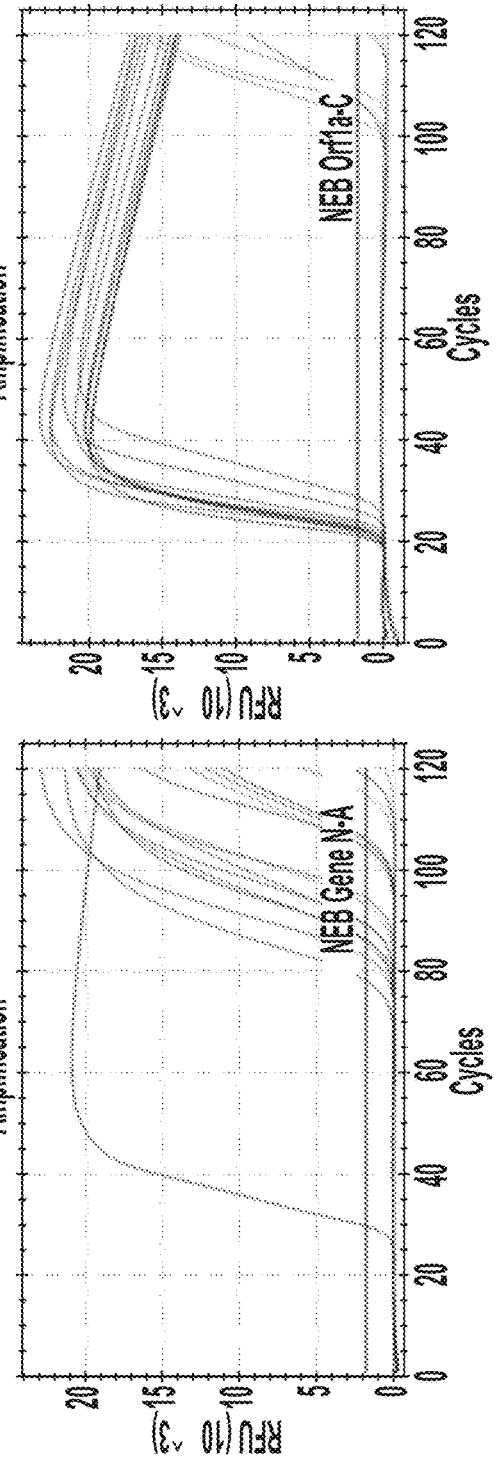
FIG. 15A  FIG. 15B  FIG. 15C  FIG. 15D

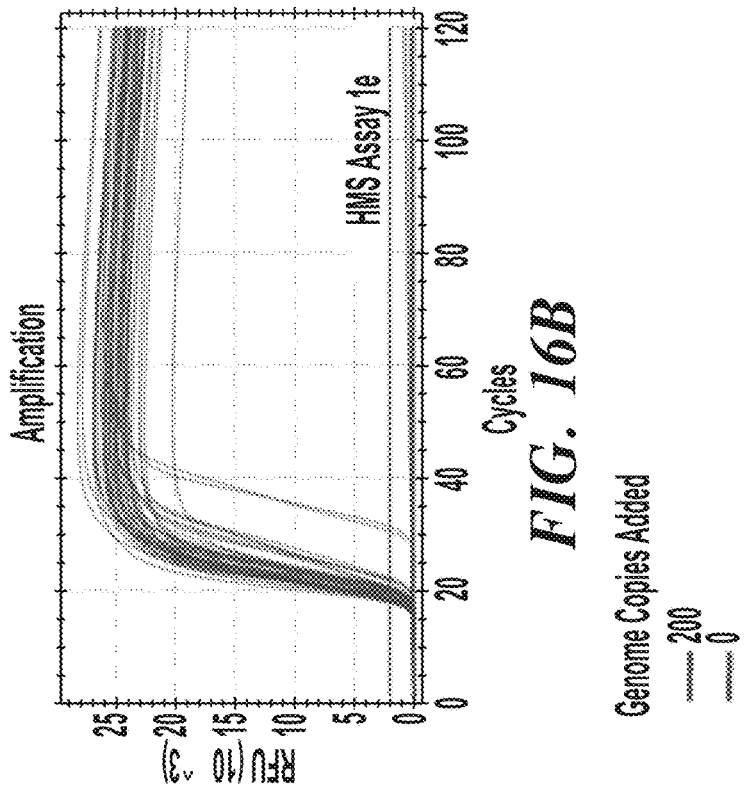
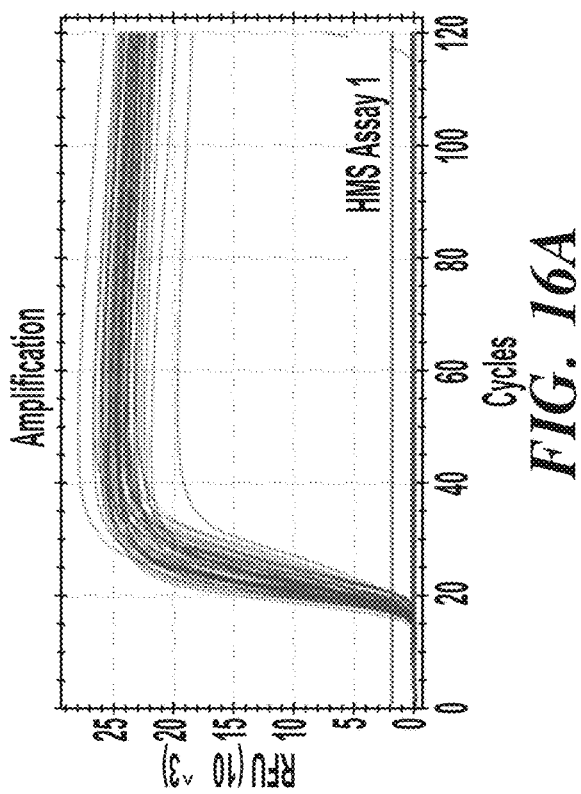
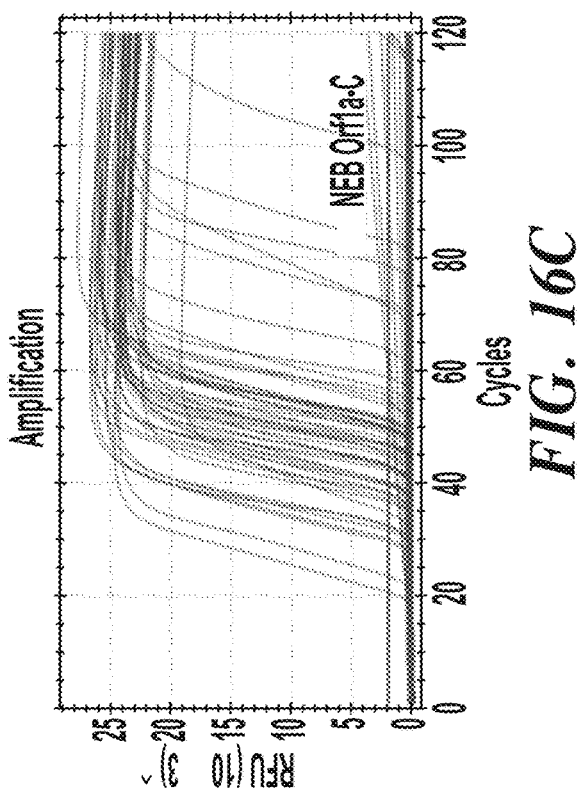
FIG. 16A
FIG. 16B
FIG. 16C

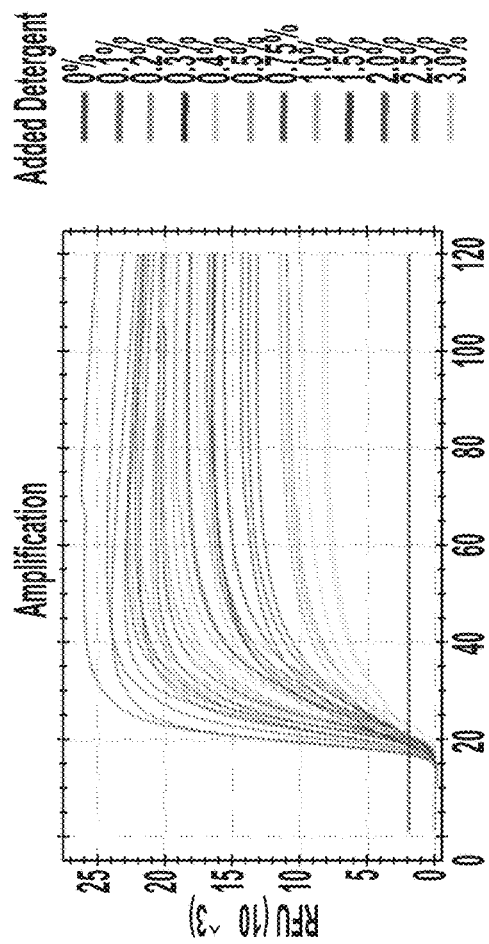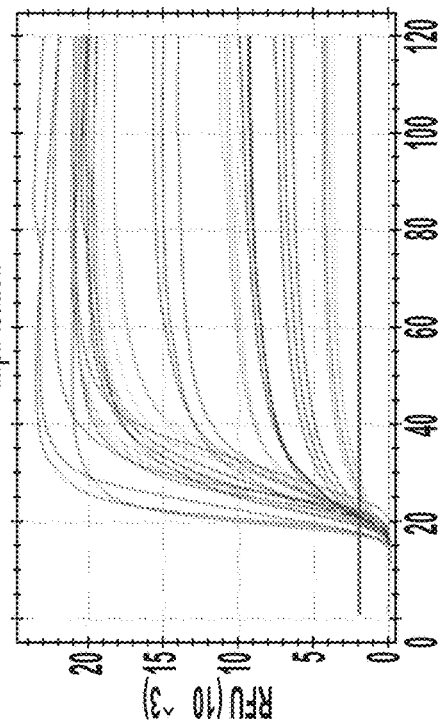
FIG. 17A
FIG. 17B

| Oligo Sequences used for HMS Assay 1 and HMS Assay 1e | |
|---|---|
| As1_F3 | CGGTGGACAAATTGTCAC |
| As1_B3 | CTTCTCTGGATTTAACACACTT |
| As1_LF | TTACAAGCTTAAAGAATGTCTGAACACT |
| As1_LB | TTGAATTTAGGTGAAACATTTGTCACG |
| As1_FIP | TCAGCACACAAAGCCAAAAATTTATCTGTGCAAAGGAAATTAAGGAG |
| As1_BIP | TATTGGTGGAGCTAAACTTAAAGCCCCTGTACAATCCCTTTGAGTG |
| As1e_FIP | TCAGCACACAAAGCCAAAAATTTATTTTTCTGTGCAAAGGAAATTAAGGAG |
| As1e_BIP | TATTGGTGGAGCTAAACTTAAAGCCTTTTCTGTACAATCCCTTTGAGTG |

FIG. 26

METHODS AND COMPOSITIONS FOR THE DIAGNOSIS AND TREATMENT OF COVID 19

CROSS-REFERENCE TO RELATED APPLICATIONS

This application claims benefit under 35 U.S.C. § 119(e) of U.S. Provisional Application No. 63/001,935 filed Mar. 30, 2020 and U.S. Provisional Application No. 62/993,423 filed Mar. 23, 2020, the contents of each which are incorporated herein by reference in their entireties.

SEQUENCE LISTING

The instant application contains a Sequence Listing which has been filed electronically in ASCII format and is hereby incorporated by reference in its entirety. Said ASCII copy, created on May 13, 2021, is named 002806-097200USPT_SL.txt and is 31,100 bytes in size.

TECHNICAL FIELD

The technology described herein relates to methods and compositions for the diagnosis and treatment of a viral infection and uses thereof.

BACKGROUND

COVID-19 is an infectious disease caused by the coronavirus, SARS-CoV-2. COVID 19 infection is characterized by mild to moderate respiratory illness in affected individuals. In some cases, the infection is lethal. As COVID 19 spreads rapidly throughout the world, there is a great need for simple, rapid, and low cost diagnostic tests and treatments to prevent the spread and severity of the coronavirus and future viral infections. Furthermore, there is currently a shortage of column-based kits to test and identify the growing numbers of people that have or may be at risk of having COVID 19. Currently available tests do not rapidly detect of the virus accurately or they require time-consuming nucleic acid purification steps, such as the widely used polymerase chain reaction (PCR) tests.

SUMMARY

The methods, compositions, assays, and kits provided herein are based, in part, on the discovery that SARS-COV-2 can be detected using a loop-mediated isothermal amplification (LAMP) assay comprising specific primers for the coronavirus, SARS-COV-2, and simplified reagents in the reaction mixture. The advantage of the methods, compositions, assays, and kits provided herein is that they do not require a nucleic acid purification step.

In one aspect, provided herein is a composition for loop-mediated isothermal amplification (LAMP) of a SARS-coronavirus-2 (COVID-19) nucleic acid, comprising:
(i) a first nucleic acid strand (first primer) comprising a nucleotide sequence CGGTGGACAAATTGTCAC (SEQ ID NO: 1);
(ii) a second nucleic acid strand (second primer) comprising a nucleotide sequence of CTTCTCTGGATTTAACACACTT (SEQ ID NO: 2);
(iii) a third nucleic acid strand (third primer) comprising a nucleotide sequence of TCAGCACACAAAGCC-AAAAATTTATCTGTGCAAAGGAAATTAAGG AG (SEQ ID NO: 3) or TCAGCACACAAAGCCAAA-AATTTATTTTTCTGTGCAAAGGAAATTA AGGAG (SEQ ID NO: 4);
(iv) a fourth nucleic acid strand (fourth primer) comprising a nucleotide sequence of TATTGGTGGAG-CTAAACTTAAAGCCCTGTACAATCCCTTTGAG-TG (SEQ ID NO: 5) or TATTGGTGGAGCTAAACT-TAAAGCCTTTTCTGTACAATCCCTTTGAGTG (SEQ ID NO: 6);
(v) a fifth nucleic acid strand (fifth primer) comprising a nucleotide sequence of TTACAAGCTTAAAGA-ATGTCTGAACACT (SEQ ID NO: 7); and
(vi) a sixth nucleic acid strand (sixth primer) comprising a nucleotide sequence of TTGAATTTAGGTGAAA-CATTTGTCACG (SEQ ID NO: 8).

In one embodiment of any of the aspects, the composition further comprises one or more reagents or buffers for loop-mediated isothermal amplification of a nucleic acid.

In another embodiment of any of the aspects, the composition further comprises a colorimetric reagent.

In another embodiment of any of the aspects, the composition further comprises dNTPs.

In another embodiment of any of the aspects, the composition further comprises a polymerase enzyme.

In another embodiment of any of the aspects, the composition further comprises a reverse transcriptase.

In another embodiment of any of the aspects, the composition further comprises a buffer solution for loop-mediated isothermal amplification of a nucleic acid.

In another embodiment of any of the aspects, the composition further comprises a detergent.

In another embodiment of any of the aspects, the composition further comprises a sample suspected of comprising SARS-coronavirus-2 (SARS-CoV2).

In another embodiment of any of the aspects, the composition further comprises silica particles, e.g., glass milk.

In another aspect, provided herein is a kit for detecting SARS-coronavirus-2, the kit comprises any of the compositions provided herein.

In one embodiment of any of the aspects, the kit comprises a nucleic acid strand comprising a nucleotide sequence substantially complementary to SEQ ID NO: 1, SEQ ID NO: 2, SEQ ID NO: 3, SEQ ID NO: 4, SEQ ID NO: 5, SEQ ID NO: 6, SEQ ID NO: 7, and/or SEQ ID NO: 8.

In another embodiment of any of the aspects, the kit comprises reagents and packaging materials thereof.

In another aspect, provided herein is an assay for detecting a SARS-coronavirus-2 nucleic acid in a sample, the method comprising:
(a) contacting a sample with a composition of any one of claims 1-8 to produce a reaction mixture, wherein the reaction mixture comprises one or more reagents or buffers for loop-mediated isothermal amplification of a nucleic acid; and
(b) heating the reaction mixture of step (a) to a temperature of about 65° C. for a period of time,
wherein a color change in the reaction mixture indicates the presence of a SARS-coronavirus-2 in the sample.

In one embodiment of any of the aspects, the assay further comprises obtaining the biological sample from a subject having or suspected of having a SARS-coronavirus-2 infection.

In another embodiment of any of the aspects, the assay further comprises cooling the reaction mixture from step (b) to room temperature.

In another embodiment of any of the aspects, the assay further comprises a lysis step prior to step (a). In another embodiment of any of the aspects, the assay further comprises a step of nucleic acid isolation or purification prior to step (a).

In another embodiment of any of the aspects, the assay further comprises a step of isolating or purifying the SARS-coronavirus-2 nucleic acid sample, where said isolating or purifying comprises contacting the sample with silica particles.

In another embodiment of any of the aspects, the reaction mixture further comprises a denaturing agent.

In another embodiment of any of the aspects, the reaction mixture further comprises guanidinium thiocyanate or guanidinium isothiocyanate.

BRIEF DESCRIPTION OF THE DRAWINGS

FIGS. 2A-8B demonstrates results of 5 assays tested with a fluorescent readout from NEB. FIG. 2A-2D depicts results for NEV N-A where: FIG. 2A is an amplification plot for No Template Control (NTC); FIG. 2B is an amplification plot for 100 copies; FIG. 2C is an amplification plot for 200 copies; and FIG. 2D is an amplification plot for 300 copies. FIG. 3A-3D depict results for NEB 1a-C where: FIG. 3A is an amplification plot for NTC; FIG. 3B is an amplification plot for 100 copies; FIG. 3C is an amplification plot for 200 copies; and FIG. 3D is an amplification plot for 300 copies. FIG. 4A-4D depict results for HMS Assay 1 where: FIG. 4A is an amplification plot for NTC; FIG. 4B is an amplification plot for 100 copies; FIG. 4C is an amplification plot for 200 copies; and FIG. 4D is an amplification plot for 300 copies. FIG. 5A is an amplification plot for NTC; FIG. 5B is an amplification plot for 100 copies; FIG. 5C is an amplification plot for 200 copies; and FIG. 5D is an amplification plot for 300 copies. FIG. 6A is an amplification plot for NTC; FIG. 6B is an amplification plot for 100 copies; FIG. 6C is an amplification plot for 200 copies; and FIG. 6D is an amplification plot for 300 copies. FIG. 7A is an amplification plot for 200 copies; and FIG. 7B is an amplification plot for NTC. FIG. 8A-8B depict results for NMS Assay 1 Repeated where: FIG. 8A is an amplification plot for 200 copies; and FIG. 8B is an amplification plot for NTC.

FIG. 9A-9B demonstrate the results of an HMS Assay 1e with "TTTT" inserted in the middle of the FIP and BIP primers. FIG. 9A is an amplification plot for 200 copies and FIG. 9B is an amplification plot for NTC.

FIG. 10A-10D demonstrates detergent tolerance in the assay with TWEEN 20. FIG. 10A is an amplification plot demonstrating 0.5% detergent; FIG. 10B is an amplification plot demonstrating 2% detergent; FIG. 10C is an amplification plot demonstrating 1% detergent; and FIG. 10D is an amplification plot demonstrating 3% detergent.

FIG. 11A is an amplification plot demonstrating 0.5% detergent; FIG. 11B is an amplification plot demonstrating 1% detergent; FIG. 11C is an amplification plot demonstrating 2% detergent; and FIG. 11D is an amplification plot demonstrating 3% detergent.

FIG. 12A is an amplification plot demonstrating 0.33×-0.04× dilution; FIG. 12B is an amplification plot demonstrating 0.021× dilution; and FIG. 12C is an amplification plot demonstrating 0.01× dilution.

FIG. 13A illustrates reactions with 500 Genomes, HMS Assay 1e with Qiagen RLT buffer at 1:25 tor 1:150 in the final reaction. FIG. 13B illustrates repeats of 500 genomes at 1:75 (top row of vials) and 1:100 (bottom row of vials) RLT, HMS assay 1e.

FIG. 15A-15D demonstrates initial sensitivity test of promising RT-LAMP assays. 10 µl RT-LAMP reactions are run with a fluorescent readout. 0 (blue), 100 (green), 200 (red), or 300 (purple) control genome RNAs included per reaction (n=4). Assays performed were: FIG. 15A—HMS Assay 1; FIG. 15B—HMS Assay 1e; FIG. 15C—NEB Gene N-A; and FIG. 15D—NEB Orf1a-C. Each cycle corresponds to 30 sec at 65 C, total time run is 60 minutes. RFU—Relative Fluorescence Units FIG. 16A-16C shows repetitions of low genome number reactions. 10 µl RT-LAMP reactions are run with a fluorescent readout. 200 (green) or zero (red) control genome RNAs included per reaction (n=48). Assays performed were: FIG. 16A—HMS Assay 1; FIG. 16B—HMS Assay 1e; and FIG. 16C—NEB Gene N-A; D—NEB Orf1a-C. Each cycle corresponds to 30 sec at 65 C, total time run is 60 minutes. RFU—Relative Fluorescence Units FIG. 17A-17B demonstrate the assessment of RT-LAMP detergent tolerance. 10 µl RT-LAMP reactions are run with a fluorescent readout. All reactions contain 500 control genomes, the HMS Assay 1 primer set and 0%-3% added detergent (see legend). Each cycle corresponds to 30 sec at 65 C, total time run is 60 minutes. RFU—Relative Fluorescence Units. FIG. 17A is a first amplification plot and FIG. 17B is a second amplification plot.

FIG. 18A—Initial GuSCN range test, contained indicated GuSCN concentration and 500 control genomes (+) or 0 control genome (−−). FIG. 18B—Repeats of reactions with 500 control genomes and 50 mM of 40 mM GuSCN.

FIG. 19A—NEB Orf1a-C assay, first run. FIG. 19B—NEB Orf1a-C assay, second run. Note 4 HMS Assay 1e reactions run with 200 genomes with (+) and without (−) additional GuSCN as a plate control. FIG. 19C—NEB Gene N-A assay. * indicates reactions that were noticeably orange, but not completely yellow.

FIG. 20A—HMS Assay 1. FIG. 20B—HMS Assay 1e.

FIG. 21A—Settled 50% silica particle suspension, i.e., glass milk, prepared easily in an afternoon. FIG. 21B—A basic schematic of the purification procedure depicting virion lysis, binding of viral RNAs to silica particles, washing away of impurities, and addition of silica-bound RNA directly to a colorimetric RT-LAMP reaction. FIG. 21C—An example of RT-LAMP reactions with silica particles after mixing. FIG. 21D—An example of RT-LAMP reactions with silica pelleted before running. FIG. 21E—1 μl of silica particle in holding buffer before being added to RT-LAMP reaction, with magnification. Arrow indicates silica particles already settling in the pipette tip.

FIG. 22C—Schematic of purification and reaction setup.

FIG. 23C—Schematic of purification and reaction setup.

FIG. 24C—Schematic of purification and reaction setup.

FIG. 25A—Brightfield image. FIG. 25B—Fluorescence, 488 nm channel.

FIG. 26 shows a table of Oligo Sequences used for HMS Assay 1 and HMS Assay 1e. Both HMS Assay 1 and HMS Assay 1e use the same F3, B3, LF, and LB oligos as shown. HMS Assay 1e uses its own FIP and BIP oligos which are identical to those used by HMS Assay 1 with the exception of 4 thymidine residues inserted in the middle (underlined and bold). In FIG. 26, SEQ ID NOS 1-2, 7-8, 3, 5, 4, and 6, respectively, are shown in order of appearance.

DETAILED DESCRIPTION

Figure 1:
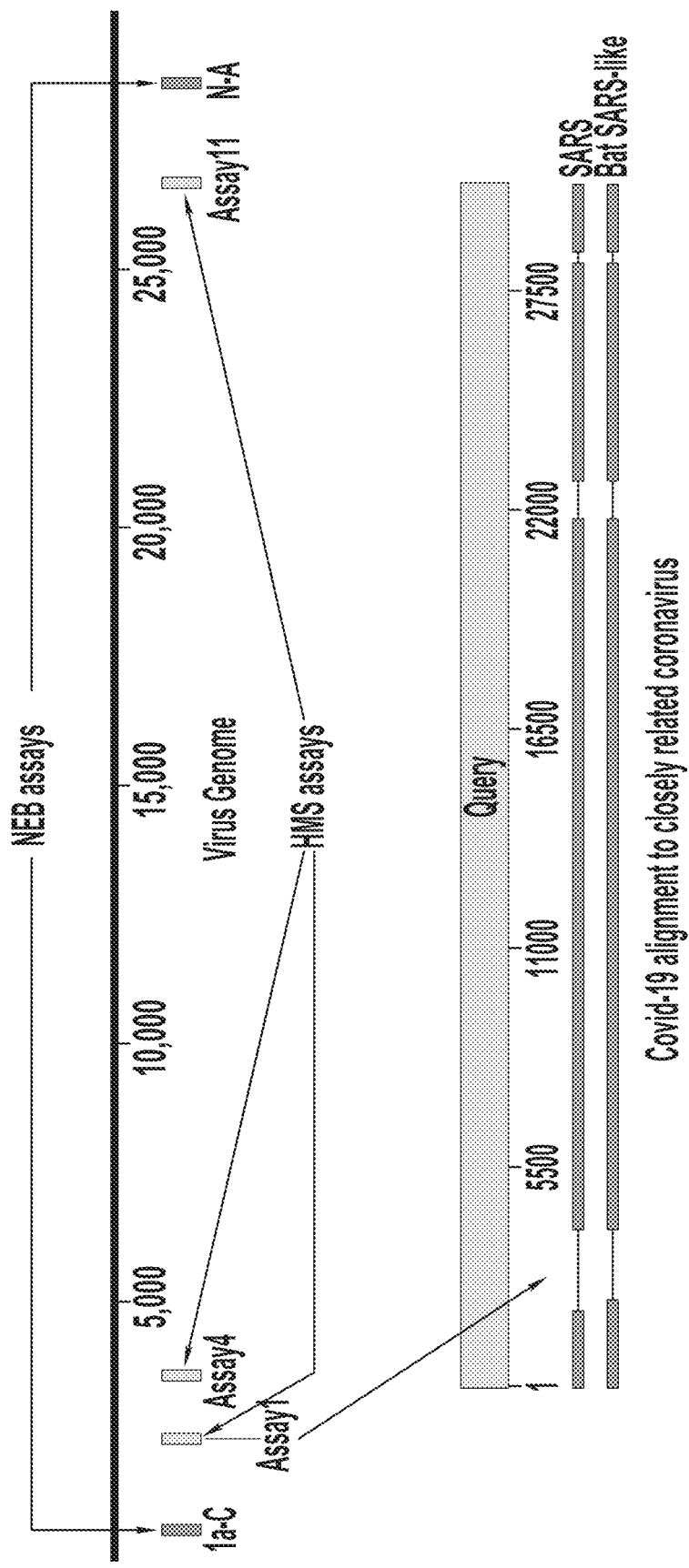
FIG. 1 demonstrates COVID 19 alignment to closely related coronavirus.
Figures 2A, 2B, 2C, 2D:
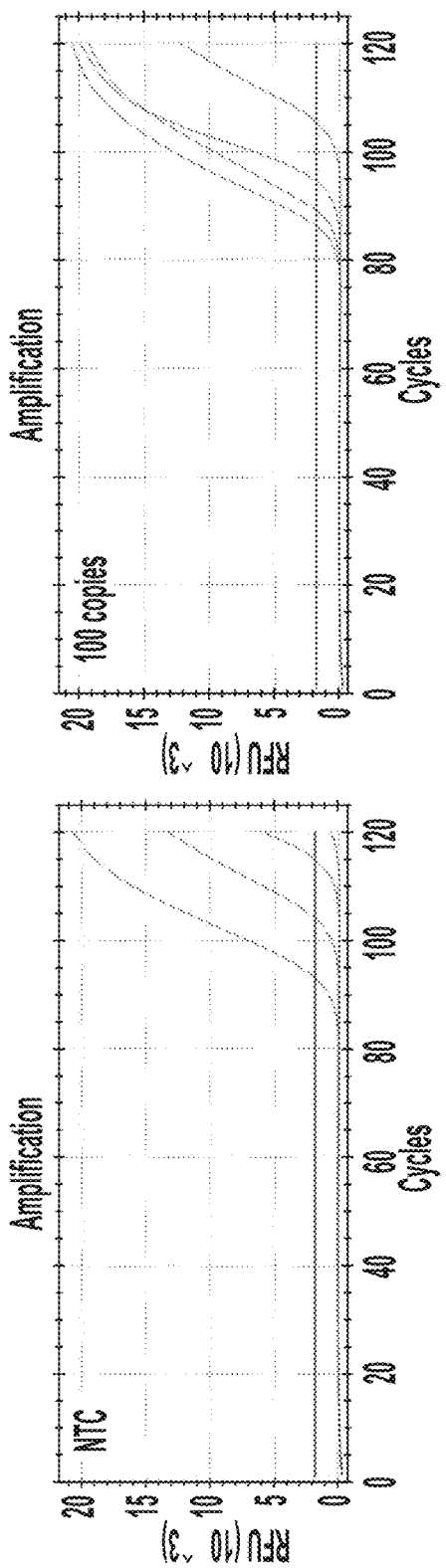
Figure 5A:
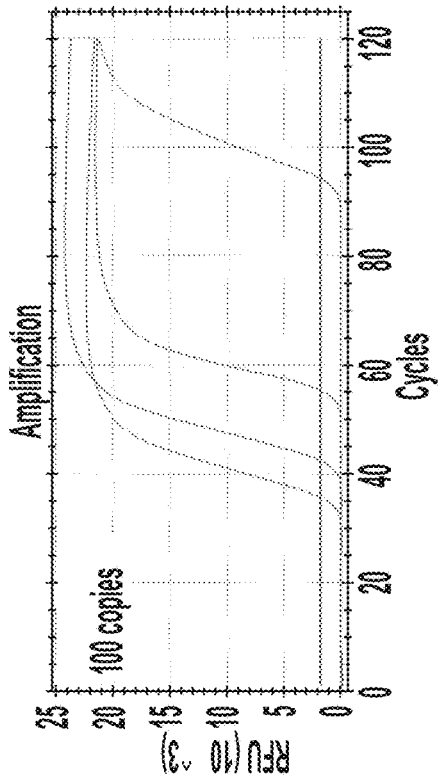
FIG. 5A-5D depict results for HMS Assay 4 where.
Figure 5B:
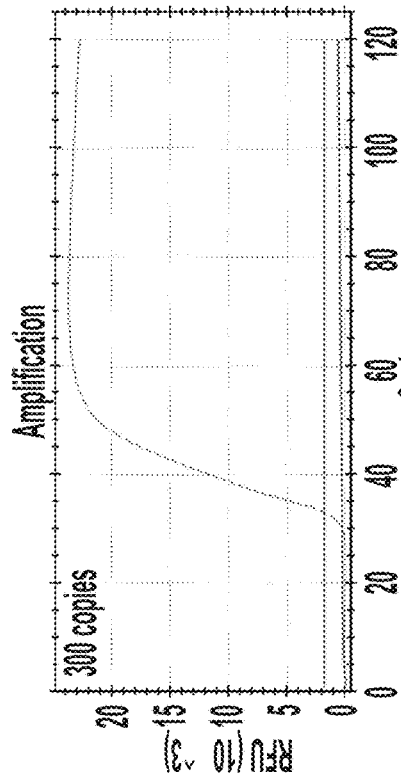
Figure 5C:
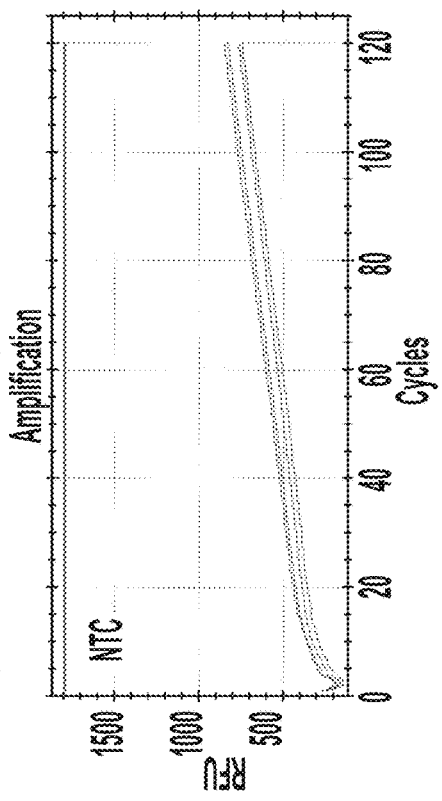
Figure 5D:
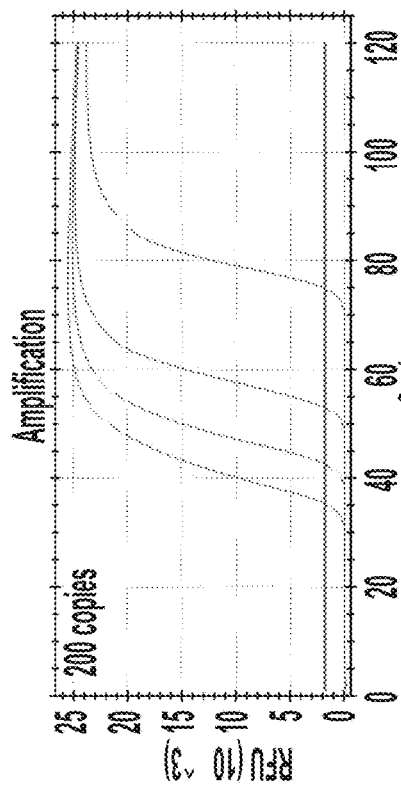
Figure 6B:
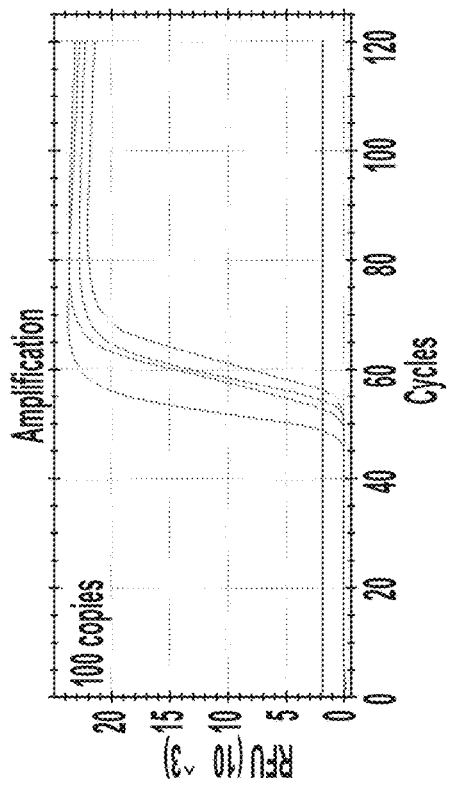
FIG. 6A-6D depict results for HMS Assay 11 where.
Figure 6D:
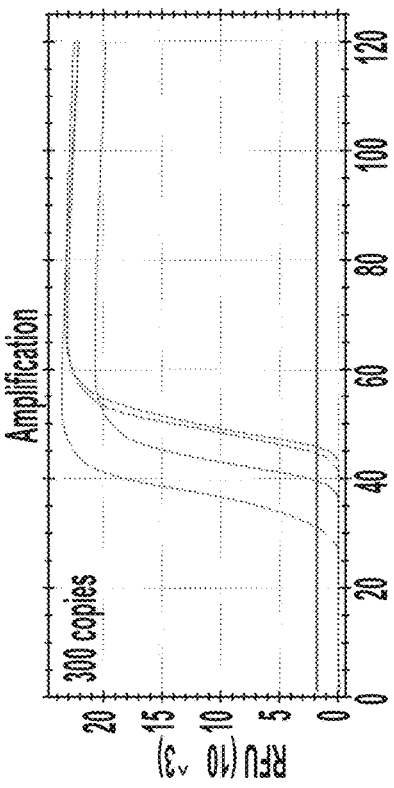
Figure 6A:
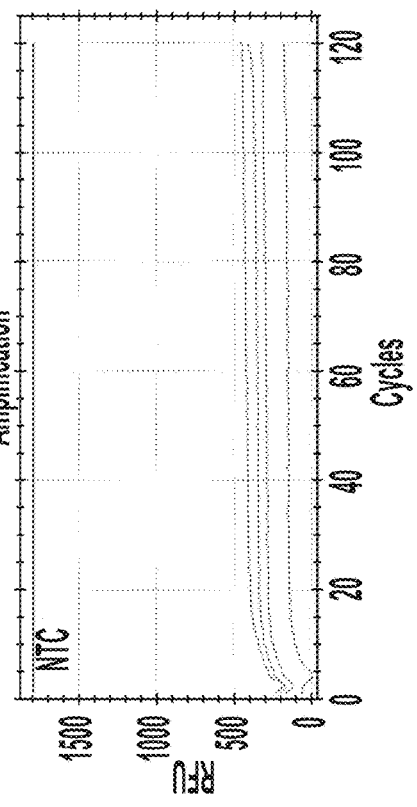
Figure 6C:
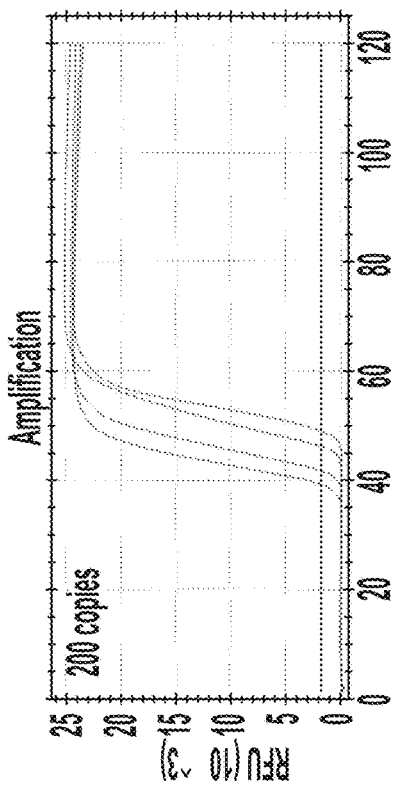
Figures 7A, 7B:
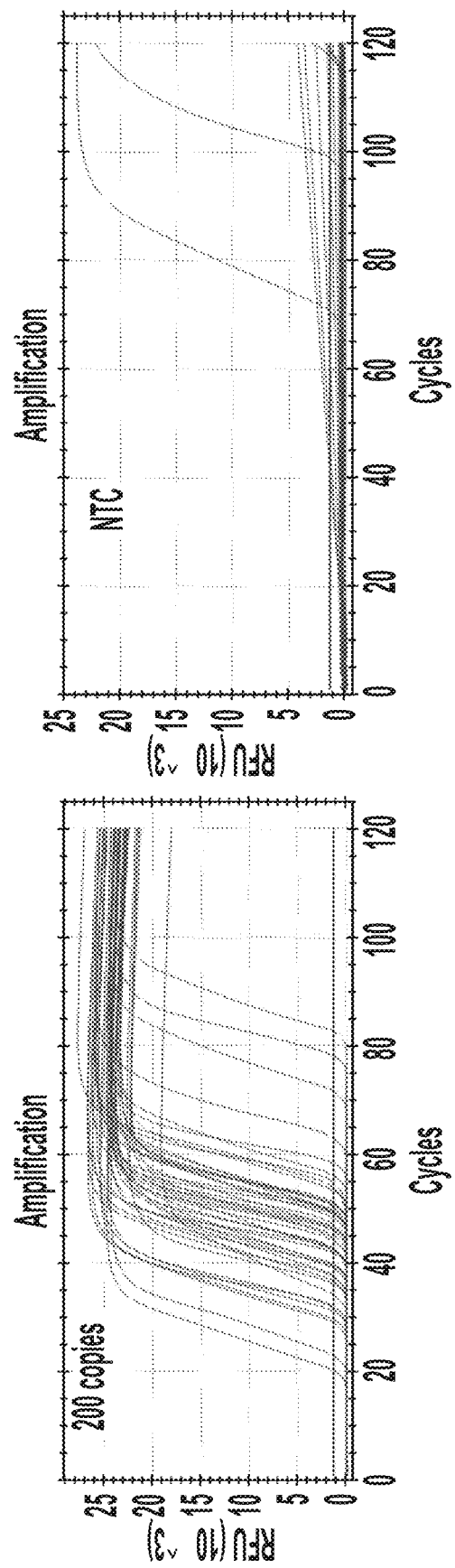
FIG. 7A-7B depict results for NEB 1a-C Repeated where.
Figure 10A:
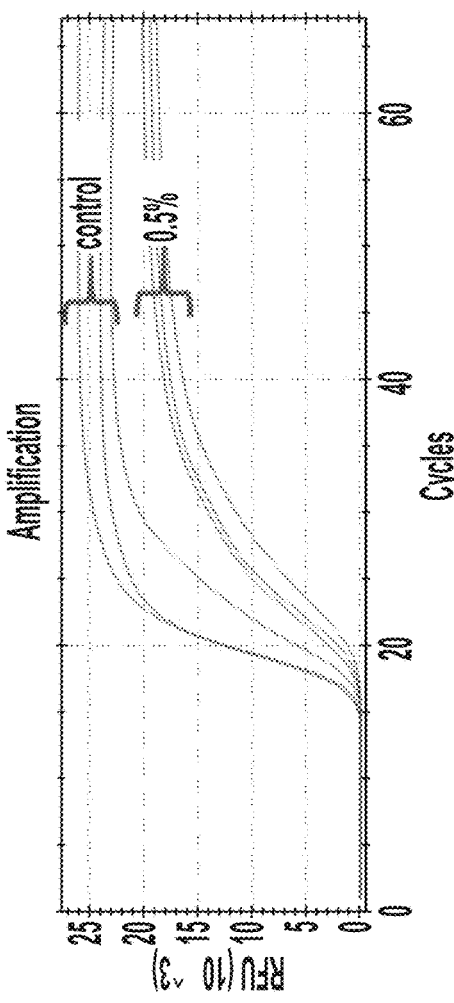
Figure 10B:
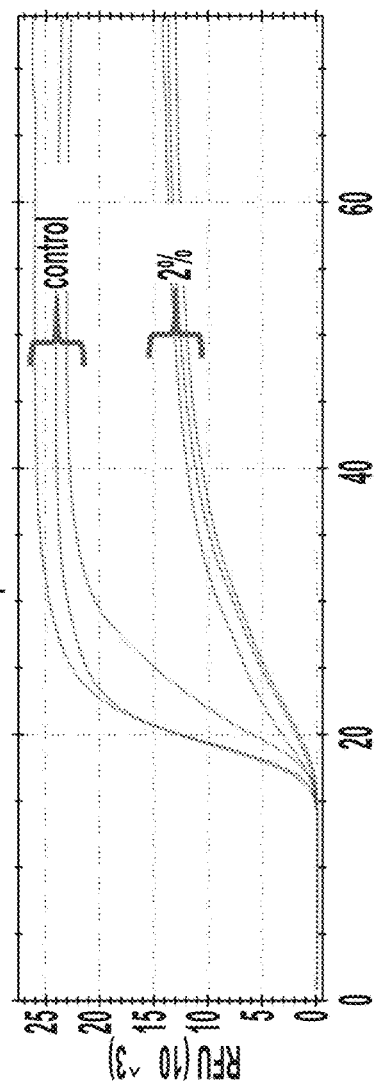
Figure 11A:
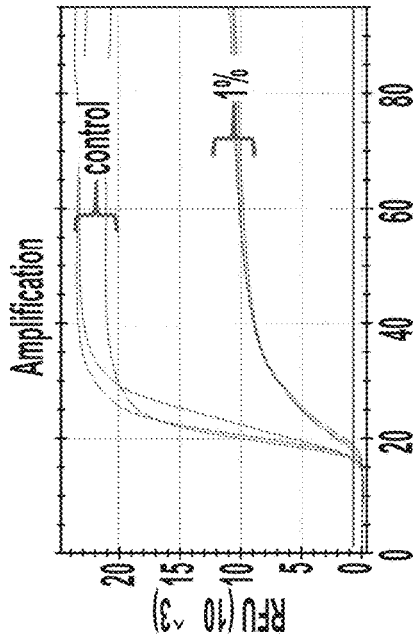
FIG. 11A-11D demonstrates detergent tolerance in the assay with varied amount of detergent.
Figure 11B:
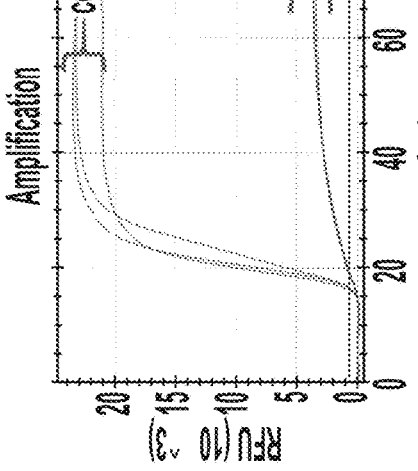
Figure 11C:
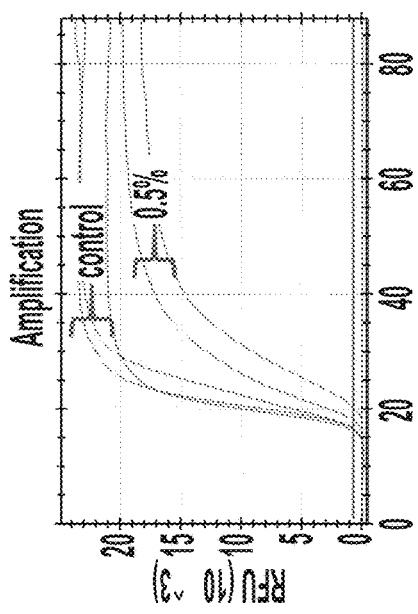
Figure 11D:
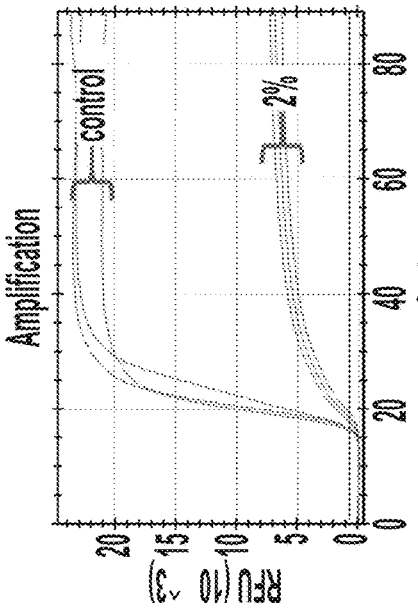
Figure 12A:
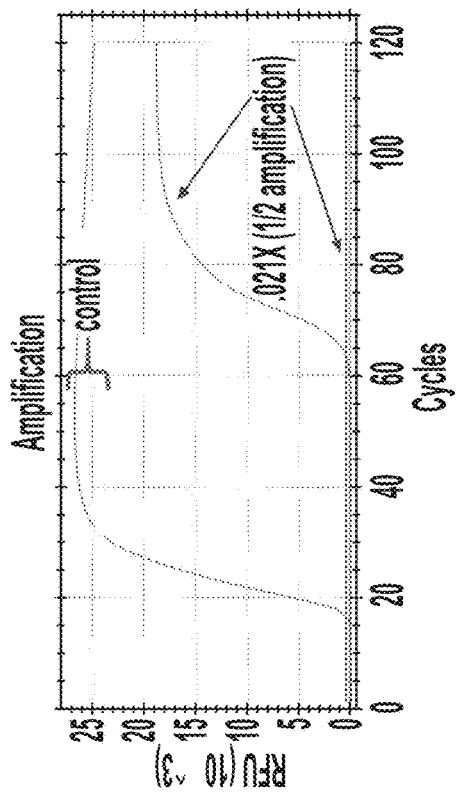
FIG. 12A-12C demonstrates guanidium lysis buffer tolerance with varying amounts of diluted lysis buffer.
Figure 12B:
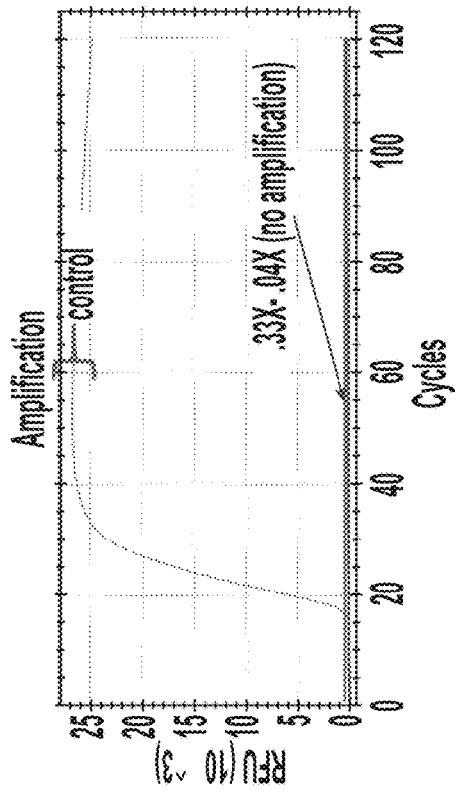
Figure 12C:
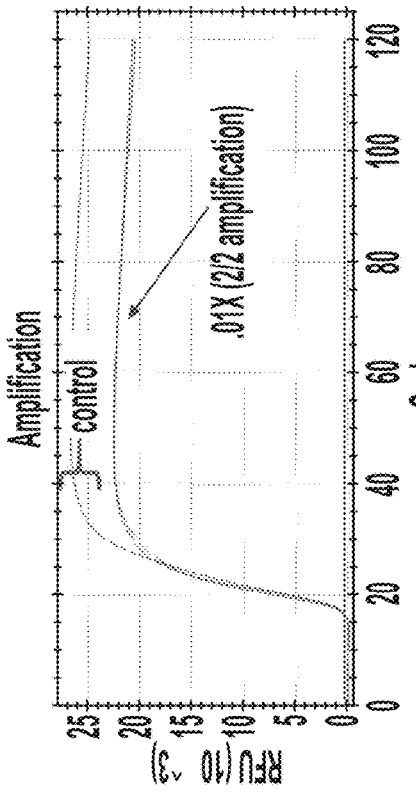
Figures 13A, 13B:
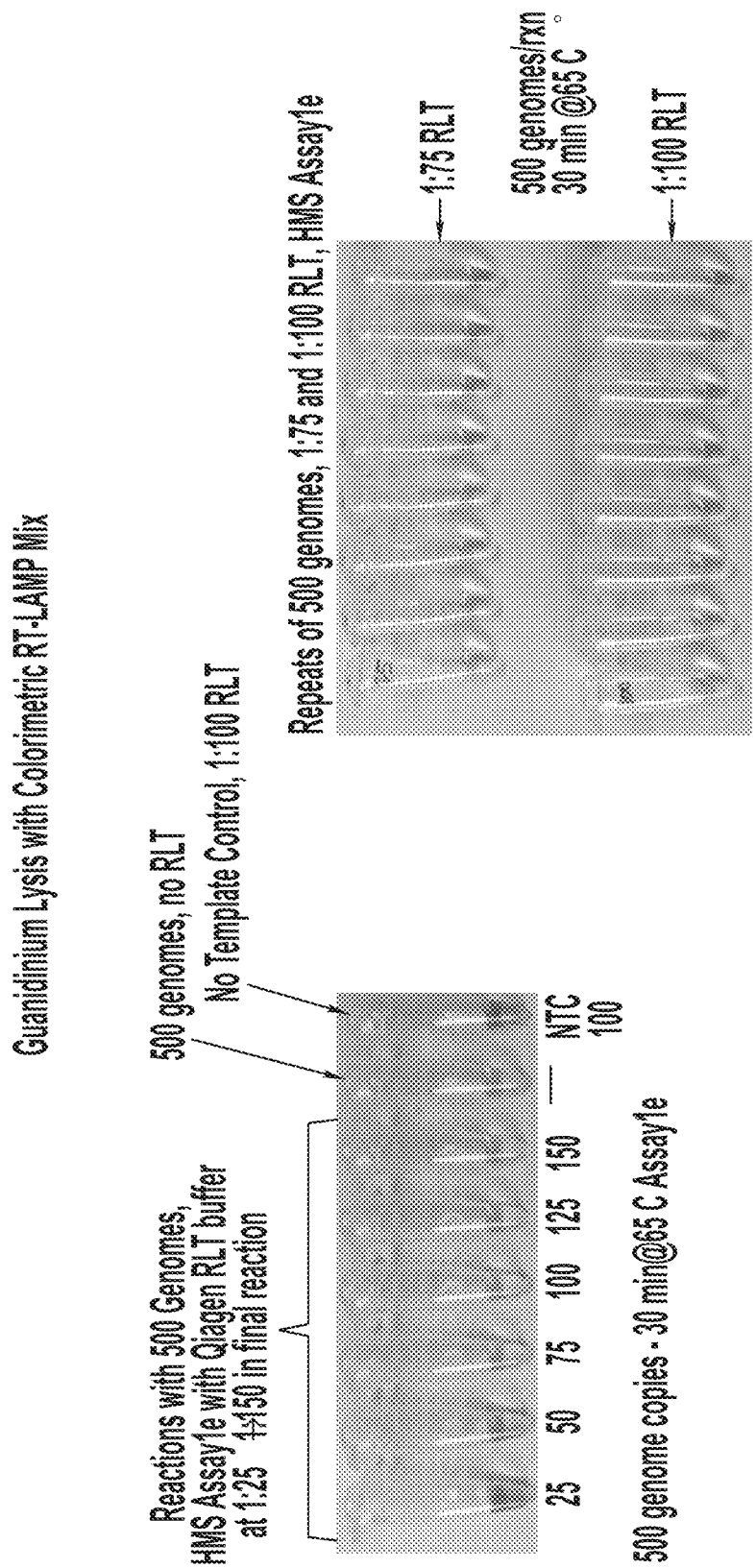
FIG. 13A-13B shows the reactions with varying concentrations of lysis buffer and the colorimetric results.

The compositions, methods, assays, and kits provided herein are based, in part, on the discovery of a fast and sensitive assay for Covid19, the viral infection caused by the SARS-coronavirus-2 virus (SARS-Cov-2). SARS-CoV2 is a highly infectious coronavirus that has spread rapidly throughout the world. Despite advances in vaccination and therapy, there is still a bottleneck for low-cost and widespread testing for infected individuals. This is due, in part, to the lack of sensitivity of rapid tests, and the alternatively more time consuming steps associated with the RT-PCR tests that have been widely used. An important limiting factor in the currently available tests for SARS-Cov-2 is the availability of kits to purify nucleic acids, currently using a column-based method. A second limitation is the need for thermocyclers, which are expensive and require trained practitioners to pre-process test samples and operate. The advantage of the compositions, methods, assays, and kits provided herein do not require a nucleic acid purification step and circumvent the more time-intensive steps associated with the widely used PCR tests. To overcome these limitations, provided herein is an assay based on the RT-LAMP technique using the nucleic acid compositions provided herein. The methods, compositions, assays, and kits provided herein also use PCR, but without the need for a thermocycler, as it is done at one temperature, 65° C.

The methods, compositions, and assays provided herein were tested on a cheek swab samples from a human subject and were easily able to detect a cellular RNA, without any purification. The test can be completed in under an hour, with minimal hands-on time, and has a simple colorimetric read out. The test provided herein entails the capacity to inoculate a reaction, keep it at 65° C., and read the color after about 30-45 minutes. For example, the reaction turns from red to yellow upon a positive result, even with as few as 120 genome copies. The reagents, compositions, and materials to rapidly test biological samples are provided herein along with the methods of using said reagents, primers, and materials for the detection, analysis, diagnostic, and treatments for COVID 19 (SARS-Cov-2). See also, e.g, Zhang et al., "Rapid Molecular Detection of SARS-CoV-2 (COVID-19) Virus RNA Using Colorimetric LAMP" *medRxiv* (2020), the contents of which is incorporated herein by reference in its entirety.

The primer sequences for the compositions and assays described herein are provided in Table 1, FIG. 26, and the working examples. The sequences are designed to a region of the SARS-Cov-2 virus that has the least similarity to the original SARS coronavirus as well as the closely related bat SARS coronavirus. This design is specific for nucleic acid sequences of SARS-CoV-2.

Finally, the methods, assays, and compositions provided herein can be used to diagnose and treat a subject at risk for or that has COVID 19. For example, the results of the assay can indicate that a subject is positive for the viral infection and an appropriate treatment can be administered.

Sample Preparation

The compositions, methods, assays, and kits provided herein can be used to test a sample for the presence or absence of a virus, e.g., a coronavirus, SARS-CoV2. The compositions, methods, assays, and kits provided herein can also be used to detect the level of viral load in a sample.

The term "sample" or "test sample" as used herein denotes a sample suspected of comprising the target nucleic acid that is to be detected. For example, a sample can be taken or isolated from a biological organism, e.g., a nasal swab or a saliva sample from a subject. In some embodiments, the sample or test sample can be a sample comprising the target nucleic acid isolated or extracted from a biological sample. In some embodiments, the sample or test sample can be a biological sample. In some embodiments of any of the aspects, the present invention encompasses several examples of a biological sample. In some embodiments of any of the aspects, the biological sample is a bodily fluid (e.g., saliva, nasal or throat swab), cells, tissue, or peripheral blood. Exemplary biological samples include, but are not limited to, a biofluid sample; mucosal secretion; saliva; mucus; nasal swab, throat swab, cheek swab; blood; serum; plasma; urine; sperm; tissue biopsy; organ biopsy; synovial fluid; bile fluid; cerebrospinal fluid; effusion; sweat; and/or tissue sample etc. The term biological sample also includes a mixture of the above-mentioned samples. The term "test sample" also includes untreated or pretreated (or pre-processed) samples. In some embodiments of any of the aspects, a test sample can comprise drinking water, sewage, food, environmental samples, etc. In some embodiments of any of the aspects, the test sample can be a nasal swab.

In some embodiments of any of the aspects, the methods and assays provided herein can further comprise a step of obtaining or having obtained a test sample from a subject. In some embodiments of any of the aspects, the subject can be a human subject. In some embodiments of any of the aspects, the subject can be a subject in need of treatment for a viral infection, e.g., COVID19 or a subject at risk of developing a viral infection (e.g., COVID19). In some embodiments of any of the aspects, the subject has or is suspected of having a SARS-CoV2 infection. In some embodiments of any of the aspects, the subject has at least one symptom of COVID19.

The test sample can be obtained by removing a sample from a subject, but can also be accomplished by using a previously isolated sample (e.g., isolated at a prior time point and isolated by the same or another person).

In some embodiments of any of the aspects, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects, the test sample is contained at room temperature (e.g., about 20° C.-25° C. or 68° F.-77° F.). In some embodiments of any of the aspects, the test sample is contained at about 4° C. or less. In some embodiments of any of the aspects, the test sample can be a frozen test sample, e.g., a frozen bodily fluid, e.g., contained at about 0° C. or less. The frozen sample can be thawed before employing the methods, assays, and kits described herein. After thawing, a frozen sample can be centrifuged before being subjected to the methods, compositions, assays and kits described herein.

In some embodiments of any of the aspects, the test sample is a clarified test sample, for example, by centrifugation and collection of a supernatant comprising the clarified test sample. In some embodiments of any of the aspects, the test sample is not a clarified test sample.

In some embodiments of any of the aspects, a test sample can be a pre-processed test sample, for example, supernatant or filtrate resulting from a treatment selected from the group consisting of centrifugation, filtration, thawing, purification, gravity or pulse-spinning, and any combinations thereof.

In some embodiments of any of the aspects, the test sample can be treated with a chemical and/or biological reagent. Chemical and/or biological reagents can be employed to protect and/or maintain the stability of the sample, including biomolecules (e.g., nucleic acids and proteins) therein, during processing.

In some embodiments of any of the aspects, a nucleic acid is isolated from the test sample. In some embodiments of any of the aspects, the methods and assays provided herein further comprise extracting, i.e., isolating/purifying the nucleic acid from the sample after a lysis step. In some embodiments of any of the aspects, the method does not comprise a nucleic acid extraction step. In other words, the sample can be used for detection after the lysis step without further isolating and/or purifying the nucleic acid. This can reduce the time for detecting the target nucleic acid.

In some embodiments of any of the aspects, the test sample can be contacted with a lysis or binding buffer. Viral and cell lysis buffers are known in the art and available to one of ordinary skill in the art. Accordingly, the compositions, methods, assays, and kits provided herein can be tested with varying concentrations of detergents, e.g., TritonX-100 or TWEEN-20, without compromising the reaction, as these are helpful for testing/lysing samples directly without requiring a separate lysis and purification step.

In some embodiments of any of the aspects, the test sample is contacted with at least about 1.5% (w/v) TWEEN-20 and/or at least about 1% (w/v) TritonX-100. In some embodiments of any of the aspects, the test sample is contacted with at least about 1.5% (w/v) or more, at least 2% (w/v) or more, at least 2.5% (w/v) or more, at least 3% (w/v) or more, at least 3.5% (w/v) or more, or at least 4% (w/v) TWEEN-20. In some embodiments of any of the aspects, the test sample is contacted with at least about 0.5% (w/v) or more, at least 1% (w/v) or more, at least 1.5% (w/v) or more, at least 2% (w/v) or more, at least 2.5% (w/v) or more, at least 3% (w/v) or more, at least 3.5% (w/v) or more, or at least 4% TritonX-100.

Generally, when working with test samples that may contain viruses, the lysis step comprises heating the sample to a high temperature to lyse the viral particles and to inactivate the virus. However, many viruses lyse at temperature much lower than the temperature needed to inactivate the virus. Furthermore, reagents such as guanidinium thiocyanate and guanidinium isothiocyanate can be used to deactivate a virus, so that it can be studied safely.

Thus, in some embodiments of any of the aspects, the sample or reaction buffer comprises a denaturing agent. In some embodiments of any of the aspects, the sample is contacted with or comprises guanidinium thiocyanate or guanidinium isothiocyanate.

The lysis step of the methods and assays provided herein can be performed at a temperature sufficient to inactivate viruses. For example, the sample can be lysed by heating the sample to a temperature from about 65° C. to about 95° C. In some embodiments of any of the aspects, the sample can be subjected to a temperature from about 65° C. to about 95° C., from about 70° C. to about 90° C., or from about 75° C. to about 85° C. As a non-limiting example, the sample can be heated to at least 65° C., at least 66° C., at least 67° C., at least 68° C., at least 69° C., at least 70° C., at least 71° C., at least 72° C., at least 73° C., at least 74° C., or at least 75° C., at least 76° C., at least 77° C., at least 79° C., at least 80° C., at least 81° C., at least 82° C., at least 83° C., at least 84° C., at least 85° C., at least 86° C., at least 87° C., at least 88° C., at least 89° C., at least 90° C., at least 91° C., at least 92° C., at least 93° C., at least 94° C., or at least 95° C. In some embodiments of any of the aspects, the sample can be subjected to a temperature of at least 65° C.

In some embodiments of any of the aspects, the lysis step is performed at, i.e., the sample is heated to, at most 65° C., at most 66° C., at most 67° C., at most 68° C., at most 69° C., at most 70° C., at most 71° C., at most 72° C., at most 73° C., at most 74° C., or at most 75° C., at most 76° C., at most 77° C., at most 79° C., at most 80° C., at most 81° C., at most 82° C., at most 83° C., at most 84° C., at most 85° C., at most 86° C., at most 87° C., at most 88° C., at most 89° C., at most 90° C., at most 91° C., at most 92° C., at most 93° C., at most 94° C., or at most 95° C. In some embodiments of any of the aspects, the sample is heated to a temperature of at most 65° C.

In some embodiments of any of the aspects, the lysis step is performed at, i.e., the sample is heated, at about 65° C., at about 66° C., at about 67° C., at about 68° C., at about 69° C., at about 70° C., at about 71° C., at about 72° C., at about 73° C., at about 74° C., or at about 75° C., at about 76° C., at about 77° C., at about 79° C., at about 80° C., at about 81° C., at about 82° C., at about 83° C., at about 84° C., at about 85° C., at about 86° C., at about 87° C., at about 88° C., at about 89° C., at about 90° C., at about 91° C., at about 92° C., at about 93° C., at about 94° C., or at about 95° C. In some embodiments of any of the aspects, the sample is heated to a temperature of about 65° C.

It is noted that lysis can also be carried out at room temperature by adding a viral lysis buffer to the sample. Thus, in some embodiments of the any of the aspects, a viral lysis buffer can be added to the sample and the sample can be incubated at room temperature, e.g., a temperature from about 15° C. to about 30° C.

For lysis, the sample can be subjected to lysis conditions for any desired amount of time to lyse the cells in a test sample and, optionally inactivate any viruses. Generally, the sample is subjected to lysis conditions, e.g., incubated at room temperature or heated, for a period of at most 30 second, at most 45 second, at most 1 minute, at most 2 minutes, at most 3 minutes, at most 4 minutes, at most 5 minutes, at most 6 minutes, at most 7 minutes, at most 8 minutes, at most 9 minutes, at most 10 minutes, at most 11 minutes, at most 12 minutes, at most 13 minutes, at most 14 minutes, or at most 15 minutes.

In some embodiments of the various aspect, the sample is subjected to lysis conditions, e.g., incubated at room temperature or heated, for a period of about 30 second, about 45 second, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, or about 15 minutes. In some preferred embodiments of any of the aspects, the sample is heated for about 4 minutes to about 6 minutes, preferably about 5 minutes.

In some embodiments of any of the aspects, a RNase inhibitor can be added along with the lysis buffer. Exemplary RNase inhibitors include, but are not limited to, guanidinium thiocyanate (GuSCN), mammalian ribonuclease inhibitor proteins such as porcine ribonuclease inhibitor and human ribonuclease inhibitor (e.g., human placenta ribonuclease inhibitor and recombinant human ribonuclease inhibitor), vanadyl ribonucleoside complexes, proteinase K, phenylglyoxal, p-hydroxyphenylglyoxal, polyamines, spermidine, 9-aminoacridine, iodoacetate, bentonite, poly[2'-O-(2,4-dinitrophenyl)]poly(adenyhlic acid), zinc sulfate, bromopyruvic acid, formamide, dimethylformamide, copper, zinc, aurintricarboxylic acid (ATA) and salts thereof such as triammonium aurintricarboxylate (aluminon), adenosine 5'-pyrophosphate, 2'-cytidine monophosphate free acid (2'-CMP), 5'-diphosphoadenosine 3'-phosphate (ppA-3'-p), 5'-diphosphoadenosine 2'-phosphate (ppA-2'-p), leucine, oligovinysulfonic acid, poly(aspartic acid), tyrosine-glutamic acid polymer, 5'-phospho-2'-deoxyuridine 3'-pyrophosphate P'→5'-ester with adenosine 3'-phosphate (pdUppAp), and analogs, derivatives and salts thereof.

In some embodiments of any of the aspects, a RNase inhibitor is not added to the lysis buffer.

The target nucleic acid can be isolated or extracted from the sample prior to detection. Accordingly, in some embodiments of any of the aspects, the methods and assays provided herein further comprise extracting, i.e., isolating/purifying the nucleic acid from the sample after the lysis step. Reagents and methods for isolating/extracting nucleic acids are well known in the art.

Inventors have discovered inter alia that nucleic acid extraction using glass milk can increase sensitivity. Accordingly, in some embodiments of any of the aspects, the test sample can be treated or contacted with silica particles or an aqueous solution thereof, a silica matrix (e.g., Glassmilk™, MP Biomedicals®) composition or solution, or a glass powder solution or suspension. The methods and assays provided herein in the working examples demonstrate that prior to the addition of a lysis/binding buffer to the test sample, the RNA in the test sample can bind to the silica particles in the solution and that the RNAse activity is minimal in the holding solution even with subsequent wash steps. This in turn increases the sensitivity of the assays and kits provided herein and reduces the processing time for the sample to detection of a virus or viral particle thereof. Thus, in some embodiments of any of the aspects, the compositions provided herein further comprise silica particles or solutions thereof.

In some embodiments of any of the aspects, the test sample is treated or contacted with at least about 40% (w/v) or more, at least 45% (w/v) or more, at least 50% (w/v) or more, at least 60% (w/v) or more, at least 70% (w/v) or more, at least 75% (w/v) glass milk.

In some embodiments of any of the aspects, the test sample is treated or contacted with silica particles or glass milk for at least about 30 seconds or more, 40 seconds or more, 50 seconds or more, 1 minute or more, 1 minute and 30 seconds or more, 2 minutes or more, 3 minutes or more, 4 minutes or more, 5 minutes or more, 6 minutes or more, 7 minutes or more, 8 minutes or more, 9 minutes or more or 10 minutes or more. In some embodiments of any of the aspects, the test sample is treated or contacted with silica particles or glass milk for no more than 2 minutes, no more than 3 minutes, no more than 4 minutes, no more than 5 minutes, no more than 6 minutes, no more than 7 minutes, no more than 8 minutes, no more than 9 minutes, no more than 10 minutes, no more than 11 minutes, no more than 12 minutes, no more than 13 minutes, no more than 14 minutes or no more than 15 minutes.

In some embodiments of any of the aspects, silica particles or glass milk can be added along with the lysis buffer.

In some embodiments of any of the aspects, a chaotropic agent, e.g., a chaotropic salt, such as GuSCN or NaI can be added along with the silica particles or glass milk. For example, NaI can be NaI can be added along with the silica particles or glass milk. If used, the NaI is added to a final concentration from about 1.5M to about 3.5M. Preferably, the NaI is added to a final concentration from about 2M to about 3M. In some embodiments, the NaI is added to a final concentration of about 2M. In some other embodiments, the NaI is added to a final concentration of about 3M.

In some embodiments of any of the aspects, the test sample is centrifuged to remove supernatant after being contacted with the silica particles or a solution thereof.

In some embodiments of any of the aspects, the test sample is washed or contacted with a wash buffer, e.g., guanidinium-based washes. The buffer can be available commercially, such as those distributed, for example by New England BioLabs (NEB)®.

In some embodiments of any of the aspects, the test sample and any added reagents are air dried. In some embodiments of any of the aspects, the test sample and any added reagents is contacted with an ethanol wash. In some embodiments of any of the aspects, the test sample and any added reagents are further centrifuged in the ethanol wash and the supernatant contains a nucleic acid or a plurality of nucleic acids. In some embodiments of any of the aspects, the nucleic acid is a viral RNA.

The nucleic acids, e.g., RNA in the sample can be maintained in a high ethanol solution or in a solution comprising guanidinium thiocyanate (GuSCN) to inhibit RNAse activity throughout. This can ensure that the samples will remain stable while testing for the presence/absence of a virus by the methods and assays provided herein.

The skilled artisan can determine which methods are appropriate for pre-processing the test sample provided herein depending on the type of sample.

Compositions and Methods for Nucleic Acid Amplification

The compositions, methods, assays, and kits provided herein can be used to detect a virus with high sensitivity (e.g., a coronavirus, SARS-CoV2) provided herein.

In another aspect, provided herein are methods, compositions, assays, and kits that can be used to detect a viral nucleic acid. In some embodiments, the viral nucleic acid is a SARS-CoV2 nucleic acid.

In another aspect, provided herein is a method of detecting a SARS-CoV2 nucleic acid, the method comprising:
  (a) contacting a sample with the compositions provided herein;
  (b) performing isothermal amplification of nucleic acids in the sample; and
  (c) monitoring the sample of a color change, wherein a change in the color of the sample indicates that the sample comprises a SARS-CoV2 nucleic acid.

In some embodiments of any of the aspects, the viral nucleic acid (e.g., SARS-CoV2 nucleic acid) is present a low starting amount, such that amplification is needed in order to detect the nucleic acid.

As used herein, "amplification" is defined as the production of additional copies of a nucleic acid sequence, i.e., for example, amplicons or amplification products. Methods of amplifying nucleic acid sequences are well known in the art. Such methods include, but are not limited to, isothermal amplification, polymerase chain reaction (PCR) and variants of PCR such as Rapid amplification of cDNA ends (RACE), ligase chain reaction (LCR), multiplex RT-PCR, immuno-PCR, SSIPA, Real Time RT-qPCR and nanofluidic digital PCR.

Accordingly, the methods described herein comprise a step of contacting the sample with a DNA polymerase and a set of nucleic acids called primers. In some embodiments of any of the aspects, a set of primers comprise one or more forward primers and one or more reverse primers that amplify a target nucleic acid (e.g., a SARS-CoV2 nucleic acid) of at least about 20 base pairs (bp) or more, unless indicated otherwise.

In some embodiments of any of the aspects, the amplification step(s) permits an amplification reaction, such a polymerase chain reaction (PCR), as described further herein.

In some embodiments of any of the aspects, the amplification step(s) permits an isothermal amplification reaction. As used herein, "isothermal amplification" refers to amplification that occurs at a single temperature. Isothermal amplification is an amplification process that is performed at a single temperature or where the major aspect of the amplification process is performed at a single temperature. Generally, isothermal amplification relies on the ability of a polymerase to copy the template strand being amplified to form a bound duplex. In the multi-step PCR process the product of the reaction is heated to separate the two strands such that a further primer can bind to the template repeating the process. Conversely, the isothermal amplification relies on a strand displacing polymerase in order to separate/displace the two strands of the duplex and re-copy the template. The key feature that differentiates the isothermal amplification is the method that is applied in order to initiate the reiterative process. Broadly, isothermal amplification can be subdivided into those methods that rely on the replacement of a primer to initiate the reiterative template copying and those that rely on continued re-use or de novo synthesis of a single primer molecule.

Isothermal amplification permits rapid and specific amplification of DNA at a constant temperature. In general, isothermal amplification is comprised of (i) sequence-specific hybridization of primers to specific genes or sequences within a nucleic acid sample or library, (ii) subsequent amplification involving multiple rounds of primer annealing, elongation, and strand displacement (as a non-limiting example, using a combination of recombinase, single-stranded binding proteins, and DNA polymerase), and (iii) detection of the product. In some embodiments of any of the aspects, the isothermal amplification produce can be detected through such methods as sequencing to confirm the identity of the amplified product or general assays such as turbidity. In some types of isothermal amplification, turbidity results from pyrophosphate byproducts produced during the reaction; these byproducts form a white precipitate that increases the turbidity of the solution. The primers used in isothermal amplification are oligonucleotides of sufficient length and appropriate sequence to provide initiation of polymerization, i.e., each primer is specifically designed to be complementary to a strand of the template (e.g., target cDNA) to be amplified. In contrast to the polymerase chain reaction (PCR) technology in which the reaction is carried out with a series of alternating temperature steps or cycles, isothermal amplification is carried out at one temperature, and does not require a thermal cycler or thermostable enzymes.

Non-limiting examples of isothermal amplification include: Recombinase Polymerase Amplification (RPA), Loop Mediated Isothermal Amplification (LAMP), Helicase-dependent isothermal DNA amplification (HDA), Rolling Circle Amplification (RCA), Nucleic acid sequence-based amplification (NASBA), strand displacement amplification (SDA), nicking enzyme amplification reaction (NEAR), and polymerase Spiral Reaction (PSR). See e.g., Yan et al., Isothermal amplified detection of DNA and RNA, March 2014, Molecular BioSystems 10(5), DOI: 10.1039/c3mb70304e, the content of which is incorporated herein by reference in its entirety.

In some embodiments of any of the aspects, the isothermal amplification is Loop Mediated Isothermal Amplification (LAMP). LAMP is a single tube technique for the amplification of DNA. LAMP uses 4-6 primers, which form loop structures to facilitate subsequent rounds of amplification. Accordingly, in some embodiments of any of the aspects provided herein, the amplification step(s) comprise(s) contacting the sample with a DNA polymerase and a set of primers, wherein the set of primers comprises 4, 5, or 6 loop-forming primers. The LAMP primers FIP and BIP (forward and backward inner primer), are designed to hybridize to the complementary and reverse complementary target sequences (e.g., a target viral nucleic acid). Displacement primers are referred to as F3 and B3. The addition to the reaction of Loop primers and STEM primers can accelerate the DNA amplification by hybridizing and extending from the hairpin loops or the region between loops, respectively.

LAMP amplification is typically achieved at 60 to 65 degrees C. for a time period dependent on the concentration of the template. Highly desirable characteristics of LAMP include high sensitivity and specificity with rapid reaction times. LAMP amplification can also proceed in the presence of PCR inhibitors permitting less stringent DNA extraction procedures. Methods of LAMP amplification are known in the art, e.g., Hardinge, P., Murray, J. A. H. Reduced False Positives and Improved Reporting of Loop-Mediated Isothermal Amplification using Quenched Fluorescent Primers. *Sci Rep* 9, 7400 (2019); and Nagamine, K., T. Hase, and T. Notomi, Accelerated reaction by loop-mediated isothermal amplification using loop primers. *Mol Cell Probes,* 2002. 16(3): p. 223-9, the contents of each of which are incorporated herein by reference in their entireties.

The compositions, methods, assays, and kits provided herein can be used with the New England Biolabs® (NEB) WarmStart™ LAMP reaction mixes (see EXAMPLE 1). The protocol for (NEB) WarmStart™ LAMP reaction can be found, e.g., on the world-wide web at https <neb.com/products/e1700-warmstart-lamp-kit-dna-rna>, the contents of which is incorporated herein by reference in its entirety and with purified RNA from Twist Biosciences®. The compositions, methods, kits, and assays provided herein in the working examples (EXAMPLE 2) can be used with NEB's colorimetric assay found on the world-wide web at https <neb.com/products/m1800-warmstart-colorimetric-lamp-2×-master-mix-dna-rna#Product%20Information, the contents of which is incorporated herein by reference in its entirety. However, these reaction mixtures are non-limiting. Additional reaction mixtures are discussed further below.

In some embodiments of any of the aspects, the DNA polymerase used in the amplification step(s) is a strand-displacing polymerase. In some embodiments of any of the aspects, the compositions provided herein further comprise a DNA polymerase.

The term "strand displacement" describes the ability to displace downstream DNA encountered during synthesis. In some embodiments of any of the aspects, at least one (e.g., 1, 2, 3, or 4) strand-displacing DNA polymerase is selected from the group consisting of: Polymerase I Klenow fragment, Bst polymerase, Phi-29 polymerase, and *Bacillus subtilis* Pol I (Bsu) polymerase. In some embodiments of any of the aspects, step (c) comprising contacting the sample (e.g., cDNA) with the strand-displacing DNA polymerases Polymerase I Klenow fragment, Bst polymerase, Phi-29 polymerase, and *Bacillus subtilis* Pol I (Bsu) polymerase.

In some embodiments of any of the aspects, the DNA polymerase is provided (i.e., added to the reaction mixture) at a sufficient concentration to promote polymerization, e.g., 0.1 U/µL to 100 U/µL. As used herein, one unit ("U") of DNA polymerase is defined as the amount of enzyme that will incorporate 10 nmol of dNTP into acid insoluble material in 30 minutes at a given temperature (e.g., 65° C.).

In some embodiments of any of the aspects, the sample is contacted with at least one set of primers. In some embodiments of any of the aspects, the set of primers is specific to a target viral nucleic acid. In some embodiments of any of the aspects, the set of primers is specific (i.e., binds specifically through complementarity) to cDNA; in other words, the DNA produced is complementary to a target viral RNA. The set of primers can be specific to any region of the target viral nucleic acid, e.g., SARS-CoV2. SEQ ID NOs: 1-8 are non-limiting examples of nucleic acids (e.g., primers, probes, etc.) that are specific for SARS-CoV-2. SEQ ID NOs: 1-8 are non-limiting examples of primers that can be included in any of the primer sets described herein. In some embodiments of any of the aspects, a set of primers as described herein are selected from the group consisting of: Table 1.

TABLE 1

Exemplary nucleic acid sequences for use in detecting SARS-CoV2

| Primer Sequence (SEQ ID NO:) | Description | Target |
|---|---|---|
| CGGTGGACAAATTGTCAC (SEQ ID NO: 1) | First Primer (F3) | SARS-CoV2 |
| CTTCTCTGGATTTAACACACTT (SEQ ID NO: 2) | Second Primer (B3) | SARS-CoV2 |
| TCAGCACACAAAGCCAAAAATTTATCT GTGCAAAGGAAATTAAGGAG (SEQ ID NO: 3) | Third Primer (FIP) | SARS-CoV2 |
| TCAGCACACAAAGCCAAAAATTTATTT TTCTGTGCAAAGGAAATTAAGGAG (SEQ ID NO: 4) | Third Primer (FIP) | SARS-CoV2 |
| TATTGGTGGAGCTAAACTTAAAGCCCT GTACAATCCCTTTGAGTG (SEQ ID NO: 5) | Fourth Primer (BIP) | SARS-CoV2 |
| TATTGGTGGAGCTAAACTTAAAGCCTTT TTCTGTACAATCCCTTTGAGTG (SEQ ID NO: 6) | Fourth Primer (BIP) | SARS-CoV2 |
| TTACAAGCTTAAAGAATGTCTGAACACT (SEQ ID NO: 7) | Fifth Primer (LOOP F) | SARS-CoV2 |
| TTGAATTTAGGTGAAACATTTGTCACG (SEQ ID NO: 8) | Sixth Primer (LOOP B) | SARS-CoV2 |

Thus, in one aspect, provided herein are compositions for loop-mediated isothermal amplification (LAMP) of a SARS-coronavirus-2 (COVID-19) nucleic acid, comprising:
(i) a first nucleic acid strand (first primer) comprising a nucleotide sequence CGGTGGACAAATTGTCAC (SEQ ID NO: 1);
(ii) a second nucleic acid strand (second primer) comprising a nucleotide sequence of CTTCTCTGGATTTAACACACTT (SEQ ID NO: 2);
(iii) a third nucleic acid strand (third primer) comprising a nucleotide sequence of TCAGCACACAAAGCCAAAAATTTATCTGTGCAAAGGAAATTAAGGAG (SEQ ID NO: 3) or TCAGCACACAAAGCCAAAAATTTATTTTTCTGTGCAAAGGAAATTAAGGAG (SEQ ID NO: 4);
(iv) a fourth nucleic acid strand (fourth primer) comprising a nucleotide sequence of TATTGGTGGAGCTAAACTTAAAGCCCTGTACAATCCCTTTGAGTG (SEQ ID NO: 5) or TATTGGTGGAGCTAAACTTAAAGCCTTTTCTGTACAATCCCTTTGAGTG (SEQ ID NO: 6);
(v) a fifth nucleic acid strand (fifth primer) comprising a nucleotide sequence of TTACAAGCTTAAAGAATGTCTGAACACT (SEQ ID NO: 7); and
(vi) a sixth nucleic acid strand (sixth primer) comprising a nucleotide sequence of TTGAATTTAGGTGAAACATTTGTCACG (SEQ ID NO: 8).

Exemplary combinations of primer sets that can be used in the compositions, methods, assays and kits provided herein include those provided in Table 2.

TABLE 2

Exemplary combinations of primer sets

| | Primer 1 (F3) | Primer 2 (B3) | Primer 3 (FIP) | Primer 4 (BIP) | Primer 5 (LoopF) | Primer 6 (LoopB) |
|---|---|---|---|---|---|---|
| Set 1 | SEQ ID NO: 1 | SEQ ID NO: 2 | SEQ ID NO: 3 | SEQ ID NO: 5 | SEQ ID NO: 7 | SEQ ID NO: 8 |
| Set 2 | SEQ ID NO: 1 | SEQ ID NO: 2 | SEQ ID NO: 3 | SEQ ID NO: 6 | SEQ ID NO: 7 | SEQ ID NO: 8 |
| Set 3 | SEQ ID NO: 1 | SEQ ID NO: 2 | SEQ ID NO: 4 | SEQ ID NO: 5 | SEQ ID NO: 7 | SEQ ID NO: 8 |
| Set 4 | SEQ ID NO: 1 | SEQ ID NO: 2 | SEQ ID NO: 4 | SEQ ID NO: 6 | SEQ ID NO: 7 | SEQ ID NO: 8 |

In some embodiments of any of the aspects, the compositions, methods, kits, and assays as provided herein comprise a nucleic acid sequence comprising at least one of SEQ ID NOs: 1-8 or a nucleic acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to one of SEQ ID NOs: 1-8 that maintains the same function (e.g., binding to a SARS-CoV-2 target). In some embodiments of any of the aspects, the compositions, methods, kits, and assays provided herein comprise a nucleic acid sequence comprising at least one of SEQ ID NOs: 1-8 or a nucleic acid sequence that is at least 95% identical to one of SEQ ID NOs: 1-8 that maintains the same function.

Modifications and Substitutions

It is contemplated herein that the compositions, nucleic acid, and primer sets provided herein can comprise modified nucleotides including modifications to nucleobase and/or sugar-phosphate backbone moieties, as long as the modified nucleotides permit hybridization of at least one nucleic acid strand (e.g., LAMP primers) to the opposing target viral nucleic acid.

Exemplary nucleic acid modifications include, but are not limited to, nucleobase modifications, sugar modifications, inter-sugar linkage modifications, conjugates (e.g., ligands), and combinations thereof. In one embodiment, a modification does not include replacement of a ribose sugar with a deoxyribose sugar as occurs in deoxyribonucleic acid. Nucleic acid modifications are known in the art, see, e.g., US20160367702A1; US20190060458A11; U.S. Pat. Nos. 8,710,200; and 7,423,142, which are incorporated herein by reference in their entireties.

Exemplary modified nucleobases include, but are not limited to, thymine (T), inosine, xanthine, hypoxanthine, nubularine, isoguanisine, tubercidine, and substituted or modified analogs of adenine, guanine, cytosine and uracil, such as 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, N4-acetyl cytosine, 2-thiocytosine, N6-methyladenine, N6-isopentyladenine, 2-methylthio-N6-isopentenyladenine, N-methylguanines, or O-alkylated bases. Further purines and pyrimidines include those disclosed in U.S. Pat. No. 3,687,808, those disclosed in the Concise Encyclopedia of Polymer Science and Engineering, pages 858-859, Kroschwitz, J. I., ed. John Wiley & Sons, 1990, and those disclosed by Englisch el al., Angewandte Chemie, International Edition, 1991, 30, 613.

Exemplary sugar modifications include, but are not limited to, 2'-Fluoro, 3'-Fluoro, 2'-OMe, 3'-OMe, and acyclic nucleotides, e.g., peptide nucleic acids (PNA), unlocked nucleic acids (UNA) or glycol nucleic acid (GNA).

In some embodiments, a nucleic acid modification can include replacement or modification of an inter-sugar linkage. Exemplary inter-sugar linkage modifications include, but are not limited to, phosphotriesters, methylphosphonates, phosphoramidate, phosphorothioates, methylenemethylimino, thiodiester, thionocarbamate, siloxane, N,N'-dimethylhydrazine (—CH2-N(CH3)-N(CH3)-), amide-3 (3'-CH2-C(=O)—N(H)-5') and amide-4 (3'-CH2-N(H)—C(=O)-5'), hydroxylamino, siloxane (dialkylsiloxxane), carboxamide, carbonate, carboxymethyl, carbamate, carboxylate ester, thioether, ethylene oxide linker, sulfide, sulfonate, sulfonamide, sulfonate ester, thioformacetal (3'-S—CH2-O-5'), formacetal (3'-O—CH2-O-5'), oxime, methyleneimino, methykenecarbonylamino, methylenemethylimino (MMI, 3'-CH2-N(CH3)-O-5'), methylenehydrazo, methylenedimethylhydrazo, methyleneoxymethylimino, ethers (C3'-O—C5'), thioethers (C3'-S—C5'), thioacetamido (C3'-N(H)—C(=O)—CH2-S—C5', C3'-O—P(O)—O—SS—C5', C3'-CH2-NH—NH—C5', 3'-NHP(O)(OCH3)-O-5' and 3'-NHP(O)(OCH3)-O-5'

In some embodiments, nucleic acid modifications can include peptide nucleic acids (PNA), bridged nucleic acids (BNA), morpholinos, locked nucleic acids (LNA), glycol nucleic acids (GNA), threose nucleic acids (TNA), or other xeno nucleic acids (XNA) described in the art.

Reaction Conditions

In some embodiments of any of the aspects, the compositions provided herein further comprise a buffer solution for loop-mediated isothermal amplification of a nucleic acid. In some embodiments of any of the aspects, the composition provided herein further comprises a colorimetric reagent. Properties of colorimetric reagents are provided elsewhere below.

In some embodiments of any of the aspects, the loop-mediated isothermal amplification (LAMP) of a SARS-coronavirus-2 (COVID-19) nucleic acid is performed at 65° C. As a non-limiting example, the isothermal amplification step(s) is performed at xenon least 50° C., at least 51° C., at least 52° C., at least 53° C., at least 54° C., at least 55° C., at least 56° C., at least 57° C., at least 58° C., at least 59° C., at least 60° C., at least 61° C., at least 62° C., at least 63° C., at least 64° C., at least 65° C., at least 66° C., at least 67° C., at least 68° C., at least 69° C., at least 70° C.

In some embodiments of any of the aspects, the isothermal amplification step(s) is performed at at most 50° C., at most 51° C., at most 52° C., at most 53° C., at most 54° C., at most 55° C., at most 56° C., at most 57° C., at most 58° C., at most 59° C., at most 60° C., at most 61° C., at most 62° C., at most 63° C., at most 64° C., at most 65° C., at most 66° C., at most 67° C., at most 68° C., at most 69° C., at most 70° C.

In some embodiments of any of the aspects, the isothermal amplification step(s) is performed at room temperature (e.g., 20° C.-22° C.). In some embodiments of any of the aspects, the isothermal amplification step(s) is performed at body temperature (e.g., 37° C.). In some embodiments of any of the aspects, the isothermal amplification step(s) is performed on a heat block set to approximately 65° C.

In some embodiments of any of the aspects, each isothermal amplification step is performed in at least 5 minutes. In some embodiments of any of the aspects, each isothermal amplification step is performed in at least 30 minutes. As a non-limiting example, the isothermal amplification step(s) is performed in at least 5 minutes, at least 10 minutes, at least 20 minutes, at least 30 minutes, at least 40 minutes, at least 50 minutes, at least 60 minutes, at least 70 minutes, at least 80 minutes, at least 90 minutes, or at least 100 minutes, or at least 12 hours, or at least 24 hours. The timing of the isothermal amplification step will depend on the temperature at which amplification is being performed. For example, if the reaction is performed at room temperature, the timing of amplification will be longer than a reaction performed at 65° C.

Reverse Transcription

In some embodiments of any of the aspects provided herein, where the target viral nucleic acid is an RNA, the target viral RNA is reverse transcribed to a complementary DNA (cDNA) that is thereafter amplified and detected. Accordingly, the methods provided herein can further comprise a step of contacting the sample with a reverse transcriptase and a set of primers. In some embodiments of any of the aspects, the compositions provided herein further comprise a reverse transcriptase.

In some embodiments of any of the aspects, the reverse transcription step and amplification step(s) are performed simultaneously in the same reaction, which can also be referred to as a "one-pot reaction".

The term "reverse transcriptase" (RT) refers to an RNA-dependent DNA polymerase used to generate complementary DNA (cDNA) from an RNA template. In some embodiments of any of the aspects, the cDNA is single-stranded DNA (ssDNA) or double-stranded DNA (dsDNA). Reverse transcriptases are used by retroviruses to replicate their genomes, by retrotransposon mobile genetic elements to proliferate within the host genome, by eukaryotic cells to extend the telomeres at the ends of their linear chromosomes.

In some embodiments of any of the aspects, the reverse transcriptase is a naturally occurring RT selected from the group consisting of: an M-MLV RT, an AMV RT, a retrotransposon RT, a telomerase reverse transcriptase, and an HIV-1 reverse transcriptase.

In some embodiments of any of the aspects, the reverse transcriptase is an engineered or recombinant version of an M-MuLV RT, AMV RT, or another naturally occurring RT as described herein. In some embodiments of any of the aspects, the reverse transcriptase is ProtoScript® II Reverse Transcriptase, which is also referred to herein as ProtoScript® II RT or Protoscriptase II. ProtoScript® II RT is a recombinant Moloney Murine Leukemia Virus (M-MuLV) reverse transcriptase, e.g., a fusion of the *Escherichia coli* trpE gene with the central region of the M-MuLV pol gene.

In some embodiments of any of the aspects, the reverse transcriptase is selected from the group consisting of: Maxima® RT (e.g., Maxima H Minus® RT), Omniscript® RT, PowerScript® RT, Sensiscript® RT (SES), SuperScript® II (SSII or SS2), SuperScript® III (SSIII or SS3), SuperScript® IV (SSIV), Accuscript® RT (ACC), a recombinant HIV RT, imProm-II@(IP2) RT, M-MLV RT (MML), Protoscript® RT (PRS), Smart MMLV (SML) RT, ThermoScript® (TSR) RT (see e.g., Levesque-Sergerie et al., BMC Molecular Biology volume 8, Article number: 93 (2007); Okello et al., PLoS One. 2010 Nov. 10; 5(11):e13931). Non limiting examples of RTs derived from MMLV include PowerScript®, ACC, MML, SML, SS2, and SS3. Non limiting examples of RTs derived from AMV include PRS and TSR. Non limiting examples of RTs derived proprietary sources include IP2, SES, Omniscript®. In some embodiments of any of the aspects, reverse transcriptase exhibits increased thermostability (e.g., up to 48° C.) compared to the wild type RT.

In some embodiments of any of the aspects, the reverse transcriptase is SuperScript® IV. In some embodiments of any of the aspects, the reverse transcriptase is Maxima H Minus® RT. In some embodiments of any of the aspects, the reverse transcriptase is SuperScript® III. In some embodiments of any of the aspects, the reverse transcriptase is MuLV. In some embodiments of any of the aspects, the reverse transcriptase is not Protoscript® II.

In some embodiments of any of the aspects, the reverse transcriptase exhibits reduced RNase H activity compared to the wild-type RT. For example, RT enzymes are often engineered with RNAse H minus point mutations to render them non-degrading to RNA.

As used herein, one unit ("U") of reverse transcriptase is defined as is defined as the amount of enzyme that will incorporate 1 nmol of dTTP into acid-insoluble material in a total reaction volume of 50 µl in 10 minutes at 37° C. using poly(rA)·oligo(dT)$_{18}$ as template ("(dT)$_{18}$" disclosed as SEQ ID NO: 11). In some embodiments of any of the aspects, the reverse transcriptase is provided at a concentration of at least 1 U/µL, at least 2 U/µL, at least 3 U/µL, at least 4 U/µL, at least 5 U/µL, at least 6 U/µL, at least 7 U/µL, at least 8 U/µL, at least 9 U/µL, at least 10 U/µL, at least 20 U/µL, at least 30 U/µL, at least 40 U/µL, at least 50 U/µL, at least 60 U/µL, at least 70 U/µL, at least 80 U/µL, at least 90 U/µL, at least 100 U/µL, at least 110 U/µL, at least 120 U/µL, at least 130 U/µL, at least 140 U/µL, at least 150 U/µL, at least 160 U/µL, at least 170 U/µL, at least 180 U/µL, at least 190 U/µL, at least 200 U/µL, at least 210 U/µL, at least 220 U/µL, at least 230 U/µL, at least 240 U/µL, at least 250 U/µL, at least 260 U/µL, at least 270 U/µL, at least 280 U/µL, at least 290 U/µL, at least 300 U/µL, at least 310 U/µL, at least 320 U/µL, at least 330 U/µL, at least 340 U/µL, at least 350 U/µL, at least 360 U/µL, at least 370 U/µL, at least 380 U/µL, at least 390 U/µL, at least 400 U/µL, at least 410 U/µL, at least 420 U/µL, at least 430 U/µL, at least 440 U/µL, at least 450 U/µL, at least 460 U/µL, at least 470 U/µL, at least 480 U/µL, at least 490 U/µL, or at least 500 U/µL. In some embodiments of any of the aspects, the reverse transcriptase is provided at a concentration of 20 U/µL. In some embodiments of any of the aspects, the reverse transcriptase is provided at a concentration of 200 U/µL.

In some embodiments of any of the aspects, the sample is contacted with a first set of primers. In some embodiments of any of the aspects, the first set of primers comprises primers that bind to target RNA and non-target RNA in the sample, i.e., "general" primers. In some embodiments of any of the aspects, the first set of primers comprises random hexamers, i.e., a mixture of oligonucleotides representing all possible hexamer sequences. In some embodiments of any of the aspects, the first set of primers comprises oligo(dT) primer, which bind to the polyA tails of mRNAs or viral transcripts.

In some embodiments of any of the aspects, the first set of primers is specific to the target RNA. In some embodiments of any of the aspects, the first set of primers comprises the reverse primer of the second set of primers (e.g., used in the amplification step). In embodiments comprising a one-pot reaction, the first set of primers can comprise the second set of primers, or the second set of primers can comprise the first set of primers. In some embodiments of any of the aspects, the RT step comprises one round of polymerization, wherein the target RNA is reverse-transcribed into a single-stranded cDNA.

In some embodiments of any of the aspects, the reverse transcription step comprises contacting the sample with a reverse transcriptase, a first set of primers, and at least one of the following: a reaction buffer, water, magnesium acetate (or another magnesium compound such as magnesium chloride) dNTPs, DTT, and/or an RNase inhibitor. In some embodiments of any of the aspects, the reaction buffer maintains the reaction at specific optimal pH (e.g., 8.1) and can include such components as Tris(pH8.1), KCl, MgCl2, and other buffers or salts. Magnesium ions (Mg2+) can function as a cofactor for polymerases, increasing their activity. Deoxynucleoside triphosphate (dNTPs) are free nucleoside triphosphates comprising deoxyribose as the sugar (e.g., dATP, dGTP, dCTP, and dTTP) that are used in the polymerization of the cDNA. Dithiothreitol (DTT) is a redox reagent used to stabilize proteins which possess free sulfhydryl groups (e.g., RT). In some embodiments of any of the aspects, the RNase inhibitor specifically inhibits RNases A, B and C, which specifically cleave ssRNA or dsRNA. RNase A and RNase B are an endoribonuclease that specifically degrades single-stranded RNA at C and U residues. RNase C recognizes dsRNA and cleaves it at specific targeted locations to transform them into mature RNAs. In some embodiments of any of the aspects, the RNase inhibitor does not specifically inhibit RNaseH. In some embodiments of any of the aspects, the RT reaction mixture does not comprise an RNaseH inhibitor.

In some embodiments of any of the aspects, the RT step is performed under that same conditions as the LAMP reaction at the same time. In some embodiments of any of the aspects, the RT step is performed under different conditions from the LAMP reaction. Methods of performing reverse transcription and LAMP are known in the art. See, e.g., Calvert, A. E., et al., Rapid colorimetric detection of Zika virus from serum and urine specimens by reverse transcription loop-mediated isothermal amplification (RT-LAMP). *PLoS One,* 2017, 12(9): p. e0185340, the contents of which is incorporated herein by reference in its entirety. Exemplary reaction mixtures are provided in the working examples in FIGS. 27-49.

If reaction products will be manipulated or analyzed after LAMP or RT-LAMP is complete, DNA polymerase activity and reverse transcription can be inactivated by heating the sample above 65° C. for at least 1 minute and/or by using a denaturing agent. In some embodiments of any of the aspects, the sample is heated to at least about 80° C. for at least about 5 minutes. In some embodiments of any of the aspects, the reaction mixture further comprises a denaturing agent. Exemplary denaturing agents include but are not limited to Sodium Dodecyl Sulfate (SDS), urea, and sodium sulfite. In some embodiments of any of the aspects, the denaturing agent is guanidinium thiocyanate or guanidinium isothiocyanate.

Non-limiting examples of analyzing the sample following amplification include sequencing, blotting techniques, and microarrays.

Detection of a Target Viral Nucleic Acid

In some embodiments of any of the aspects provided herein, the output product of the LAMP amplification is encoded or produced by a "reporter" or "reporter molecule." As used herein, a "reporter" refers to a molecule (e.g., protein, small molecule, or compound) that can be used to measure gene expression, e.g., detecting the presence of a SARs-CoV2 nucleic acid, and generally produce a signal such as fluorescence, luminescence, or color. The reporter can provide a quantitative readout or a qualitative readout. In most instances, the presence of a reporter in a sample can be readily observed. For example, fluorescent proteins (e.g., green fluorescent protein (GFP), red fluorescent protein such as mCherry) cause a sample to fluoresce when excited with light of a particular wavelength, luciferases cause a sample to catalyze a reaction that produces light, and enzymes such as p-galactosidase convert a substrate to a colored product. Reporters for use in accordance with the compositions, methods, assays, and kits provided herein include any reporter described herein or known to one of ordinary skill in the art and sequences encoding the same.

Thus, in some embodiments of any of the aspects, the compositions, methods, assays, and kits provided herein comprise a colorimetric reagent or a pH-sensitive reagent. A positive test result of the assay provided herein can be indicated by a color change visible to the naked eye. Stated another way, the colorimetric output will be visible when a SARS-CoV2 target nucleic acid is amplified in the sample provided herein, e.g., a nucleic acid that hybridizes to one or more of the primers provided herein. Methods of detecting amplification of target nucleic acids are described, e.g., in U.S. Pat. Nos. 9,580,748 B2; 9,074,249 B2; 10,253,357 B2; Notomi, Tsugunori, et al. "Loop-mediated isothermal amplification (LAMP): principle, features, and future prospects." *Journal of microbiology* 53.1 (2015): 1-5; and Tomita, et. al., *Nat. Protocols*, 3(5):877-82 (2008), the contents of each of which are incorporated herein by reference in their entireties.

Examples of sequences and genes encoding fluorescent proteins that can be used in accordance with the compositions, methods, assays, and kits provided herein include, without limitation, those proteins provided in U.S. Patent Application No. 2012/0003630 (see Table 59), incorporated herein by reference in its entirety.

Examples of UV fluorescent proteins useful as reporter proteins include, but are not limited to, Sirius. Examples of blue fluorescent proteins include, but are not limited to, Azurite, EBFP2, mKalama1, mTagBFP2, and tagBFP. Examples of cyan fluorescent proteins include, but are not limited to, ECFP, Cerulean, mCerulean3, SCFP3A, CyPet, mTurquoise, mTurquoise2, TagCFP, Mtfp1, monomeric Midoriishi-Cyan, and Aquamarine. Examples of green fluorescent proteins include, but are not limited to, TurboGFP, TagGFP2, mUKG, Superfolder GFP, Emerald, EGFP, Monomeric Azami Green, mWasabi, Clover, and mNeonGreen. Examples of yellow fluorescent proteins include, but are not limited to, TagYFP, EYFP, Topaz, Venus, SYFP2, Citrine, Ypet, IanRFP-ΔS83, and mPapaya1. Examples of orange fluorescent proteins include, but are not limited to, Monomeric Kusabira-Orange, mOrange, mOrange2, mKOx, and Mko2. Examples of red fluorescent proteins include, but are not limited to, TagRFP, TagRFP-T, mRuby, mRuby2, mTangerine, mApple, mStrawberry, FusionRed, mCherry, and mNectarine. Examples of far red fluorescent proteins include, but are not limited to, mKate2, HcRed-Tandem, mPlum, mRaspberry, mNeptune, NirFP, TagRFP657, TagRFP675, and mCardinal. Examples of near IR fluorescent proteins include, but are not limited to, iFP1.4, iRFP713 (iRFP), iRFP670, iRFP682, iRFP702, iRFP720, and iFP2.0. Examples of sapphire-type fluorescent proteins include, but are not limited to, Sapphire, T-Sapphire, and mAmetrine. Examples of long Stokes shift fluorescent proteins include, but are not limited to, mKeima Red, mBeRFP, LSS-mKate2, LSS-mKate1, and LSSmOrange.

Luciferases can also be used as reporter molecules, as cells in a test sample tend to have little to no background luminescence in the absence of a luciferase. Luminescence can be readily quantified using a plate reader or luminescence counter. Examples of genes encoding luciferases that can be used in the systems described herein include, without limitation, dmMyD88-linker-Rluc, dmMyD88-linker-Rluc-linker-PEST191, *Renilla* luciferase, and firefly luciferase (from *Pholinus pyralis*).

Enzymes that produce colored substrates ("colorimetric enzymes") can also be used as reporter molecules. Enzymatic products can be quantified using spectrophotometers or other instruments that can take absorbance measurements including plate readers. Like luciferases, enzymes such as β-galactosidase can be used for measuring low levels of gene expression because they tend to amplify low signals. Examples of genes encoding colorimetric enzymes that can be used in accordance with the systems described herein include, without limitation, chitinase and fragments thereof, lacZ alpha fragment, lacZ (encoding β-galactosidase, full-length), and xylE.

LAMP reactions can be readily monitored by measuring pH change using visible and fluorescent dyes. For example, by initiating the isothermal amplification reaction in alkaline conditions (pH 8-10) in the presence of a neutral pH range transition indicator, an initial high pH color can typically be observed. As amplification proceeds in the presence of the target viral nucleic acid provided herein, the solution pH drops substantially to a second, acidic pH (~pH 5-7) in as little as 10 minutes resulting in a detectable color change visible by eye.

Suitable visible dyes that can be used in the compositions, methods, assays, and kits provided herein can include but are not limited to: Neutral Red, which has a clear-yellow color when pH is higher than 8 and a red color when pH is less than 6.8; Phenol Red, which has a red color when pH is higher than 8 and a yellow color when pH is less than 6.4; Cresol Red, which has a reddish-purple color when pH is higher than 8.8 and a yellow color when pH is less than 7.2; Thymol Blue, which has a blue color when pH is higher than 9.6 and a yellow color when pH is less than 8.0; Phenolphthalein, which has a fuchsia color when pH is higher than 10 and colorless when pH is less than 8.3; and Naphtholphthalein, which has a greenish color when pH is higher than 8.7 and a pale-reddish color when pH is less than 7.3. Other examples of pH indicators include but are not limited to, 5-(and-6)carboxy SNARF-1, methyl yellow, bromocresol violet, methyl orange, bromophenol blue, naphthyl red, bromocresol green, methyl red, azolitmin, nile blue, thymolphthalein, alizarin yellow, salicyl yellow, nitramine. These indicators may transition outside the range of traditional DNA polymerase tolerances, but the principle of amplification detection may be applied to alternate detection methods with an indicator appropriate for desired pH range. Visual and fluorescent dyes including those mentioned above can be chemically modified to have altered colorimetric properties in response to pH changes.

Additional examples of LAMP amplification can be monitored by measuring concomitant pH changes that are detectable visually using chemical or fluorescent dyes, e.g., see Gill, et al., Nucleos. Nucleot. Nucleic Acids, 27:224-43 (2008); Kim, et al., Bioanalysis, 3:227-39 (2011); Nagamine et al., Mol. Cel. Probes, 16:223-9 (2002); Notomi et al., Nucleic Acids Res., 28:E63 (2000); and Nagamine et al., Clin. Chem., 47:1742-3 (2001), the contents of each of which are incorporated herein by reference in their entireties.

In some embodiments of any of the aspects, the reporter is comprised in the reaction mixture. In some embodiments of any of the aspects, a positive test result is indicated by a color change of the sample from red to yellow.

Target Viral Nucleic Acids

Provided herein are compositions, methods, assays, and kits that can be used to detect a target viral nucleic acid. In some embodiments of any of the aspects, the target viral nucleic acid is a target viral DNA or RNA, which can also be referred to as a "gene of interest." In some embodiments of any of the aspects, the target viral DNA or RNA can be any DNA or RNA sequence or any gene.

Provided herein are compositions, methods, kits, and assays that can be used to detect a target nucleic acid. In some embodiments of any of the aspects, the target nucleic acid is a target viral DNA, which can also be referred to as "an DNA of interest" or a "gene of interest." In some embodiments of any of the aspects, the target DNA can be any DNA sequence or any gene.

In some embodiments of any of the aspects, the target nucleic acid is a target viral RNA, which can also be referred to as "an RNA of interest." Ribonucleic acid (RNA) is a polymeric nucleic acid molecule essential in various biological roles in coding, decoding, regulation and expression of genes. Each nucleotide in RNA contains a ribose sugar, with carbons numbered 1' through 5'. A base is attached to the 1' position, in general, adenine (A), cytosine (C), guanine (G), or uracil (U). A phosphate group is attached to the 3' position of one ribose and the 5' position of the next. The phosphate groups have a negative charge each, making RNA a charged molecule (polyanion). An important structural component of RNA that distinguishes it from DNA is the presence of a hydroxyl group at the 2' position of the ribose sugar. In some embodiments of any of the aspects, the target RNA can be any known type of RNA. In some embodiments of any of the aspects, the target viral RNA comprises an RNA selected from Table 3.

As used herein, the term "RNA virus" refers to a virus comprising an RNA genome. In some embodiments of any of the aspects, the RNA virus is a double-stranded RNA virus, a positive-sense RNA virus, a negative-sense RNA virus, or a reverse transcribing virus (e.g., retrovirus). Non-limiting examples of RNA viruses include Arteriviridae, Coronaviridae (e.g., Coronavirus, SARS-CoV), Mesoniviridae, Roniviridae, Dicistroviridae, Iflaviridae, Marnaviridae, Picornaviridae (e.g., Poliovirus, Rhinovirus (a common cold virus), Hepatitis A virus), Secoviridae (e.g., sub Comovirinae), Alphaflexiviridae, Betaflexiviridae, Gammaflexiviridae, Tymoviridae, Alphatetraviridae, Alvernaviridae, Astroviridae, Barnaviridae, Benyviridae, Bromoviridae, Caliciviridae (e.g., Norwalk virus), Carmotetraviridae, Closteroviridae, Flaviviridae (e.g., Yellow fever virus, West Nile virus, Hepatitis C virus, Dengue fever virus, Zika virus), Fusariviridae, Hepeviridae, Hypoviridae, Leviviridae, Luteoviridae (e.g., Barley yellow dwarf virus), Polycipiviridae, Narnaviridae, Nodaviridae, Permutotetraviridae, Potyviridae, Sarthroviridae, Statovirus, Togaviridae (e.g., Rubella virus, Ross River virus, Sindbis virus, Chikungunya virus), Tombusviridae, and Virgaviridae.

In some embodiments of any of the aspects, the RNA virus is severe acute respiratory syndrome (SARS) coronavirus. In some embodiments of any of the aspects, the RNA virus is severe acute respiratory syndrome coronavirus 2 (SARS-CoV-2), which causes coronavirus disease of 2019 (COVID19 or simply COVID). In some embodiments of any of the aspects, the RNA virus is any known RNA virus.

In some embodiments of any of the aspects, the target viral nucleic acid provided herein is from a coronavirus. The scientific name for coronavirus is Orthocoronavirinae or Coronavirinae. Coronaviruses belong to the family of Coro-

TABLE 3

Non-limiting Examples of Target Viral RNAs

| Type | Abbr. | Function | Distribution |
|---|---|---|---|
| RNAs involved in protein synthesis | | | |
| Messenger RNA | mRNA | Codes for protein | All organisms |
| Ribosomal RNA | rRNA | Translation | All organisms |
| Signal recognition particle RNA | 7SL RNA or SRP RNA | Membrane integration | All organisms |
| Transfer RNA | tRNA | Translation | All organisms |
| RNAs involved in post-transcriptional modification or DNA replication | | | |
| Ribonuclease P | RNase P | tRNA maturation | All organisms |
| Regulatory RNAs | | | |
| Antisense RNA | aRNA, asRNA | Transcriptional attenuation/mRNA degradation/mRNA stabilization/Translation block | All organisms |
| Viral genome | | Information carrier | Double-stranded RNA viruses, positive-sense RNA viruses, negative-sense RNA viruses, many satellite viruses and reverse transcribing viruses |
| Viroid | | Self-propagating | Infected plants |
| Satellite RNA | | Self-propagating | Infected cells |

Accordingly, in one aspect described herein is a method of detecting an RNA virus in a sample from a subject, the method comprising: (a) obtaining a test sample from a subject suspected of having a viral infection; and (b) performing the methods or assay as provided herein.

naviridae, order Nidovirales, and realm Riboviria. They are divided into alphacoronaviruses and betacoronaviruses which infect mammals—and gammacoronaviruses and deltacoronaviruses which primarily infect birds. Non limiting examples of alphacoronaviruses include: Human coronavirus 229E, Human coronavirus NL63, Miniopterus bat coronavirus 1, Miniopterus bat coronavirus HKU8, Porcine epidemic diarrhea virus, Rhinolophus bat coronavirus HKU2, Scotophilus bat coronavirus 512, and Feline Infectious Peritonitis Virus (FIPV, also referred to as Feline Infectious Hepatitis Virus). Non limiting examples of betacoronaviruses include: Betacoronavirus 1 (e.g., Bovine Coronavirus, Human coronavirus OC43), Human coronavirus HKU1, Murine coronavirus (also known as Mouse hepatitis virus (MHV)), *Pipistrellus* bat coronavirus HKU5, Rousettus bat coronavirus HKU9, Severe acute respiratory syndrome-related coronavirus (e.g., SARS-CoV, SARS-CoV-2), *Tylonycteris* bat coronavirus HKU4, Middle East respiratory syndrome (MERS)-related coronavirus, and Hedgehog coronavirus 1 (EriCoV). Non limiting examples of gammacoronaviruses include: Beluga whale coronavirus SW1, and Infectious bronchitis virus. Non limiting examples of deltacoronaviruses include: Bulbul coronavirus HKU11, and Porcine coronavirus HKU15.

In some embodiments of any of the aspects, the target viral nucleic acid comprises at least a portion of severe acute respiratory syndrome coronavirus 2 isolate SARS-CoV-2, (see e.g., complete genome, SARS-CoV-2-January 2020/NCBI Ref: NC_045512.2 Assembly (wuhCor1)). In some embodiments of any of the aspects, the target viral nucleic acid comprises SEQ ID NO: 9 (N nucleocapsid phosphoprotein-Severe acute respiratory syndrome coronavirus 2 isolate SARS-CoV-2-A). In some embodiments of any of the aspects, the target viral nucleic acid comprises SEQ ID NO: 10 (ORFlab polyprotein). In some embodiments of any of the aspects, the target viral nucleic acid comprises one of SEQ ID NOs: 9-10, or a nucleic acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to one of SEQ ID NOs: 9-10 that maintains the same function or a codon-optimized version of SEQ ID NOs: 9-10. In some embodiments of any of the aspects, the target viral nucleic acid comprises one of SEQ ID NOs: 9-10, or a nucleic acid sequence that is at least 95% identical to one of SEQ ID NOs: 9-10 that maintains the same function.

SEQ ID NO: 9 Severe acute respiratory syndrome coronavirus 2 isolate Wuhan-Hu-1, N nucleocapsid phosphoprotein, Gene ID: 43740575, 1260 bp ss-RNA, NC_045512 REGION: 28274-29533 ATGTCTGATAATGGACCCCAA AATCAGCGAAATGCACCCCGCATTACGTTTGGTG GACCCTCAGATTCAACTGGCAGTAACCAGAATG- GAGAACGCAGTGGGGCGCGATCAAAACAACGT CGGCCCCAAGGTTTACCCAATAATACTGCGTCTTG GTTCACCGCTCTCACTCAACATGGCAAGGAAGAC CTTAAATTCCCTCGAGGACAAGGCGTTCCAATTAA CACCAATAGCAGTCCAGATGACCAAATTGGCTAC- TACCGAAGAGCTACCAGACGAATTCGTGGTGGTGA CGGTAAAATGAAAGATCTCAGTCCAAGATGGTAT- TTCTACTACCTAGGAACTGGGCCAGAAGCTGGAC TTCCCTATGGTGCTAACAAAGACGGCATCATATGG GTTGCAACTGAGGGAGCCTTGAATACACCAAAA- GATCACATTGGCACCCGCAATCCTGCTAACAATGC TGC AATCGTGCTACAACTTCCTCAAG GAACAACA TTGCCAAAAGGCTTCTACGCAGAAGGGAGCAGAG GCGGCAGTCAAGCCTCTTCTCGTTCCTC ATCACGT AGTCGCAACAGTTCAAGAAATTCAACTCCAGGCA GCAGTAGGGGAACTTCTCCTGCTAGAATG GCTGG CAATGGCGGTGATGCTGCTCTTGCTTTGCT GCTGC TTGACAGATTGAACCAGCTTGAGAGCAAAA TGTC TGGTAAAGGCCAACAACAACAAGGCCAAACTGT- CACTAAGAAATCTGCTGCTGAGGCTTCTAAGAA GCCTCGGCAAAAACGTACTGCCACTAAAGCATAC A ATGTAACACAAGCTTTCGGCAGACGTGGTCCAGAA CAAACCCAAGGAAATTTTGGGGACCAGGAACTA ATCAGACAAGGAACTGATTACAAACATTGGCCGC AAA TTGCACAATTTGCCCCCAGCGCTTCAG CGTTC TTCGGAATGTCGCGCATTGGCATGGAAGTCACAC CTTC GGGAACGTGGTTGACCTACACAGGTGCCAT- CAAATTGGATGACAAAGATCCAAATTTCAAAGAT- CAAGTC ATTTTGCTGAATAAGCATATTGACGCATA- CAAAACATTCCCACCAACAGAGCCTAAAAAGGA- CAAAAAGA AGAAGGCTGATGAAACTCAAGCCTTA CCGCAGAGACAGAAGAAACAGCAAACTGTGACT CTTCTTCCTGC TGCAGATTTGGATGATTTCTCCAA ACAATTGCAACAATCCATGAGCAGTGCTGACT- CAACTCAGGCCTAA SEQ ID NO: 10, Severe acute respiratory syndrome coronavirus 2 isolate Wuhan-Hu-1 ORFlab polyprotein Gene ID: 43740578, updated on 6 Mar. 2021, NCBI Reference Sequence: NC_045512.2: REGION 266-21555 ATG- GAGAGCCTTGTCCCTGGTTTCAACGAGAAAACA CAC GTCCAACTCAGTTTGCCTGTTTTACAGGTTC G CGACGTGCTCGTACGTGGCTTTGGAGACTCCGTG- GAGGAGGTCTTATCAGAGGCACGTCAACATCTTAA AGATGGCACTTGTGGCTTAGTAGAAGTTGAAA AA GGCGTTTTGCCTCAACTTGAACAGCCCTATGTGTTC ATCAAACGTTCGGATGCTCGAACTGCACCTCATG GTCATGTTATGGTTGAGCTGGTAGCAGAACTCGA AGGCATTCAGTACGGTCGTAGTGGTGAGACACTT GGTGTCCTTGTCCCTCATGTGGGCGA ATACCAG T G GC TTACCGCAAGGTTCTTCTTCGTAAGAACGGTA ATAAAGGAGCTGGTGGCCATAGTTACGGCGCCGA TCTA AAGTCATTTGACTTAGGCGACGAGCTTGGC A CTGATCCTTATGAAGATTTTCAAGAAAACTGGAA CACTA AACATAGCAGTGGTGTTACCCGTGAACTC ATGCGTGAGCTTAACGGAGGGGCATACACTCGC- TATGTCGA TAACAACTTCTGTGGCCCTGATGGCTA CCCTCTTGAGTGCATTAAAGACCTTCTAGCACGT GCTGGTAAA GCTTCATGCACTTTGTCCGAACAACT GGACTTTATTGACACTAAGAGGGGTGTATACT GC T GCCGTGAAC ATGAGCATGAAATTGCTTGGTACAC GGAACGTTCTGAAAAGAGCTATGAATTGCAGAC ACCTTTTGAAAT TAAATTGGCAAAGAAATTTGAC A CCTTCAATGGGGAATGTCCAAATTTTGTATTTCCCT- TAAATTCCATA ATCAAGACTATTCAACCAAGGGTT- GAAAAGAAAAAGCTTGATGGCTTTATGGGTAGAAT- TCGATCTGTCT ATCCAGTTGCGTCACCAAATGAATG CAACCAAATGTGCCTTTCAACTCTCATGAAGTGT- GATCATTGTGG TGAAACTTCATGGCAGACGGGCG ATTTTGTTAAAGCCACTTGCGAATTTTGTGGCACT- GAGAATTTGACT AAAGAAGGTGCCACTACTTGT G GTTACTTACCCCAAAATGCTGTTGTTAAAATTTATT GTCCAGCATGTC ACAATTCAGAAGTAGGACCTG A GCATAGTCTTGCCGAATACCATAATGAATCTGGCTT- GAAAACCATTCT TCGTAAGGGTGGTCGCACTAT- TGCCTTTGGAGGCTGTGTGTTCTCTTATGTTGG TT G CCATAACAAGTGT GCCTATTGGGTTCCACGTG CT AGCGCTAACATAGGTTGTAACCATACAGGTGTTG TTGGAGAAGGTTCCG AAGGTCTTAATGACA ACC TTCTTGAAATACTCCAAAAAGAGAAAGTCAACAT- CAATATTGTTGGTGACTT TAAACTTAATGAAG AGA TCGCCATTATTTGGCATCTTTTCTGCTTCCACA AGTGCTTTTGTGGAAACT GTGAAAGGTTTGGAT- TATAAAGCATTCAAACAAATTGTTGAATCCTG TGG TAATTTTAAAGTTACAAAAG GAAAAGCTA AAAAA GGTGCCTGGAATATTGGTGAACAGAAATCAATACT- GAGTCCTCTTTATGCATTTGC ATCAGAGGCTGC TCGTGTTGTACGATCAATTTTCTCCCGCACTCTT- GAAACTGCTCAAAATTCTGTGCGT GTTTTACAGAA
GGCCGCTATAACAATACTAGATGGAATTTCACAGT-
ATTCACTGAGACTCATTGATGCTA TGATGTTCACA T
CTGATTTGGCTACTAACAATCTAGTTGTAATGGCC-
TACATTACAGGTGGTGTTGTTCAGTTGACTTCGCA
GTGGCTAACTAACATCTTTGGCACTGTTTATGAAA
AACTCAAACCCGTCCTTGATTGGCTTGAAGAGA AG
TTTAAGGAAGGTGTAGAGTTTCTTAGAGACGG TTG
GGAAATTGTTAAATTTATCTCAA CCTGTGCTTGTGA
AATTGTCGGTGGACAAATTGTCACCTGTGCAAAG G
AAATTAAGGAGAGTGTTCAGACATTCTTTAAGCTT
GTAAATAAATTTTTGGCTTTGTGTGCTGACTCTAT-
CATTATTGGTGGAGCTAAACTT AAAGCCTTGAATT-
TAGGTGAAACATTTGTCACGCACTCAAAGGGATTG-
TACAGAAAGTGTGTTAAATCCA GAGAAGAAACTG-
GCCTACTCATGCCTCTAAAAGCCCCAAAAGAAAT-
TATCTTCTTAGAGGGAGAAACACT TCCCACAGAA-
GTGTTAACAGAGGAAGTTGTCTTGAAAACTGGTG-
ATTTACAACCATTAGAACAACCTACTAGTGAAGCT-
GTTGAAGCTCCATTGGTTGGTACACCAGTTTGTAT-
TAACGGGCTTATGTTGCTCGAAATCAAAGACACA-
GAAAAGTACTGTGCCCTTGCACCTAATATGATGGT-
AACAACAATACCTTCACACTCAAAGGCGGTG- C
ACCAACAAAGGTTACTTTTGGTGATGACACTGTGA-
TAGAAGTGCAAGGTTACAAGAGTGTGAAT ATCAC
TTTTGAACTTGATGAAAGGATTGATAAAGTACTTA
ATGAGAAGTGCTCTGCCTATACAGTTGAAC TCGG T
ACAGAAGTAAATGAGTTCGCCTGTGTTGTGGCAG
ATGCTGTCATAAAAACTTTGCAACCAGTATC TGA A
TTACTTACACCACTGGGCATTGATTTAGATGAGTG-
GAGTATGGCTACATACTACTTATTTGATGAG TCTGG
TGAGTTTAAATTGGCTTCACATATGTATTGTTCTTT
CTACCCTCCAGATGAGGATGAAGAAGAAG GTGAT-
TGTGAAGAAGAAGAGTTTGAGCCATCAACTCAAT
ATGAGTATGGTACTGAAGATGATTACCAAGG TAAA
CCTTTGGAATTTGGTGCCACTTCTGCTGCTCTTCA
ACCTGAAGAAGAGCAAGAAGAAGATTGGTTA GAT-
GATGATAGTCAACAAACTGTTGGTCAACAAGACG
GCAGTGAGGACAATCAGACAACTACTATTCAAAC
AATTGTTGAGGTTCAACCTCAATTAGAGATGGAAC-
TTACACCAGTTGTTCAGACTATTGAAGTGAATAG
TTTTAGTGGTTATTTAAAACTTACTGACAATGTATA-
CATTAAAAATGCAGACATTGTGGAAGAAGCTAAA
AAGGTAAAACCAACAGTGGTTGTTAATGCAGC-
CAATGTTTACCTTAAACATGGAGGAGGTGTTGCAG-
GAG CCTTAAATAAGGCTACTAACAATGCCATGCAA
GTTGAATCTGATGATTACATAGCTACTAATGGAC-
CACT TAAAGTGGGTGGTAGTTGTGTTTTAAGCG GA
CACAATCTTGCTAAACACTGTCTTCATGTTGTCG G
CCCA AATGTTAACAAAGGTGAAGACATTCAACTT
CTTAAGAGTGCTTATGAAAATTTTAATCAGCACG A
AGTTCTACTTGCACCATTATTATCAGCTGGTATTT TT
GGTGCTGACCCTATACATTCTTTAAGAGTTTGT GT
AGA TACTGTTCGCACAAATGTCTACTTAGCTGT CT
TTGATAAAAATCTCTATGACAAACTTGTTTCAA GCT
TTTTGGAAATGAAGAGTGAAAAGCAAG TTGAACA
AAAGATCGCTGAGATTCCTAAAGAGGA AGTTAA
GCCAT TTATAACTGAAAGTAA ACCTT CAGTT-
GAACAGAGAAAACAAGATGATAAGAAAATCAAA
GCTTGTGTTGA AGAAGTTACAACAACTCTGGAA G
A AACTAAGTTCCTCACAGAAAACTTGTTACTTTAT-
ATTGACATTAAT GGCAATCTTCATCCAGATTCTGCC
ACTCTTGTTAGTAGCATTGACATCACTTTCTTAAA
GAAAGATGCTC CATATATAGTGGGTGATGTTGTTCA
AGAGGGTGTTTTAACTGCTGTGGTTATACCTACTA
AAAAGGCTGG TGGCACTACTGAAATGCTAGCGA A
AGCTTTGAGAAAAGTGCCAACAGACAATTATA TA
ACCACTTACCCG GGTCAGGGTTTAAATGGTTACA
CTGTAGAGGAGGCAAAGACAGTGCTTAAAAAG TG
TAAAAGTGCCTTTT ACATTCTACCATCTATTATCTCT
AATGAGAAGCAAGAAATTCTTGGAACTGTTTCTTG-
GAATTTGCGAGA AATGCTTGCACATGCAGAAGA A
ACACGCAAATTAATGCCTGTCTGTGTGGAAAC TA
AAGCCATAGTTTCA ACTATACAGCGTAAATATA AG
GGTATTAAAATACAAGAGGGTGTGGTTGATATG
GTGCTAGATTTTACT TTTACACCAGTAAA ACAACT
GTAGCGTCACTTATCAACACACTTAACGATCTAAAT-
GAAACTCTTGTTAC AATGCCACTTGGCTATGTAA C
A CATGGCTTAAATTTGGAAGAAGCTGCTC GGTATA
TGAGATCTCTCAAA GTGCCAGCTACAGTTTCT GTT-
TCTTCACCTGATGCTGTTACAGCGTATAATGGTTAT
CTTACTTCTTCTT CTAAAACACCTGAAGAACATTT-
TATTGAAACCATCTCACTTGCTGGTTCCTATAAA-
GATTGGTCCTATTC TGGACAATCTACACAACTA GG
TATAGAATTTCTTAAGAGAGGTGATAAAAGTGTAT-
ATTACACTAGTAAT CCTACCACATTCCACCTAGAT
GGTGAAGTTATCACCTTTGACAATCTTAAGACACT
TCTTTCTTTGAGAG AAGTGAGGACTATTAAGGT G
TTACAACAGTAGACAACATTAACCTCCACACG CA
AGTTGTGGACATGTC AATGACATATGGACAAC AGT
TTGGTCCAACTTATTTGGATGGAGCTGATGTTACT
AAAAATAAAACCTCAT AATTCACATGAAGGTAAAA-
CATTTTATGTTTTACCTAATGATGACACTCTACGT
GTTGAGGCTTTTGAGT ACTACCACACAACTGATC
CTAGTTTTCTGGGTAGGTACATGTCAGCATTAAAT-
CACACTAAAAAGTGGAA ATACCCACAAGTTAAT G
GTTTAACTTCTATTAAATGGGCAGATAACAACTGT-
TATCTTGCCACTGCATTG TTAACACTCCAACAA ATA
GAGTTGAAGTTTAATCCACCTGCTCTACAAGATG
CTTATTACAGAGCAAGGG CTGGTGAAGCTGC TA
ACTTTTGTGCACTTATCTTAGCCTACTGTAATAAG
ACAGTAGGTGAGTTAGGTGA TGTTAGAGAAA CAA
TGAGTTACTTGTTTCAACATGCCAATTTAGATTCT
TGCAAAAGAGTCTTGAACGTG GTGTGTAAAACTT
GTGGACAACAGCAGACAACCCTTAAGGGTGTA GA
AGCTGTTATGTACATGGGCACACTTTCTTATGAA CA
ATTTAAGAAAGGTGTTCAGATACCTTGTACGTGT-
GGTAAACAAGCTACAAAATATCT AGTACAACAG-
GAGTCACCTTTTGTTATGATGTCAGCACCACCTGC-
TCAGTATGAACTTAAGCATGGTACA TTTACTTGTG
CTAGTGAGTACACTGGTAATTACCAGTGTGGTCAC
TATAAACATATAACTTCTAAAGAAA CTTTGTATTG-
CATAGACGGTGCTTTACTTACAAAGTCCTCAGAA-
TACAAAGGTCCTATTACGGATGTTTTCTACAAA GA-
AAACAGTTACACAACAACCATAAAACCAGTTACT-
TATAAATTGGATGGTGTTGTTTGTACA GAAATTGA-
CCCTAAGTTGGACAATTATTATAAGAAAGACAAT-
TCTTATTTCACAGAGCAACCAATTGATC TTGTACC-
AAACCAACCATATCCAAACGCAAGCTTCGATAAT-
TTTAAGTTTGTATGTGATAATATCAAATT TGCTGAT-
GATTTAAACCAGTTAACTGGTTATAAGAAACC TGC-
TTCAAGAGAGCTTAAAGTTACATTTTTC CCTGACT-
TAAATGGTGATGTGGTGGCTATTGATTATAAACAC-
TACACACCCTCTTTTAAGAAAGGAGCTAAATTGT-
TACATAAACCTATTGTTTGGCATGTTAACAATGCA-
ACTAATAAAGCCACGTATAAACCAAATACCTGGT G-
TATACGTTGTCTTTGGAGCACAAAACCAGTTGAAA-
CATCAAATTCGTTTGATGTACTGAAGTCAGAGGA-
CGCGCAGGGAATGGATAATTTGCCTGCGAAGAT-
CTAAAACCAGTCTCTGAAGAAGTAGTGGAAAAT-
CCTACCATACAGAAAGACGTTCTTGAGTGTAATGT-
GAAAACTACCGAAGTTGTAGGAGACATTATACT
TAAACCAGCAAATAATAGTTTAAAAATTACAGA-
AGAGGTTGGCCACACAGATCTAATGGCTGCT- TATGTA GACAATTCTAGTCTTACTATTAAGAAACC
TAATGAATTATCTAGAGTATTAGGTTTGAAAACC
CTTGCTA CTCATGGTTTAGCTGCTGTTAATAGTGT
CCCTTGGGATACTATAGCTAATTATGCTAAGCC
TTTTCTTAAA CAAAGTTGTTAGTACAACTACTAACAT-
AGTTACACGGTGTTTAAACCGTGTTTGTACTAAT-
TATATGCCTTATTTCTTTACTTTATTGCTACAATTG
TG TACTTTTACTAGAAGTACAAATTCTAGAATTAA
AG CATCTA TGCCGACTACTATAGCAAA GAATAC T
GTTAAGAGTGTCGGTAAATTTTGTCTAGAGGCTT-
CATTTAATTA TTTGAAGTCACCTAATTTTTCTAAA
CTGATAAATATTATAATTTGGTTTTTACTATTAAGT
GTTTGCCTA GGTTCTTTAATCTACTCAACCG CTGCT
TTAGGTGTTTTAATGTCTAATTTAGGCATGCCTTCT-
TACTGTA CTGGTTACAGAGAAGGCTATTTGAACTC-
TACTAATGTCACTATTGCAACCTACTGTACTGGTTC-
TATACC TTGTAGTGTTTGTCTTAGTGGTTTA GATTC
TTTAGACACCTATCCTTCTTTAGAAACTATACAAAT-
TACC ATTTCATCTTTTAAATGGGATTTAACTGCT TT
TGGCTTAGTTGCAGAGTGGTTTTTGGCATATATTCT
TTTCACTAGGTTTTTCTATGTACTTGGATTGGCTG
CAATCATGCAATTGTTTTTCAGCTATTTTGCAGTA C
A TTTTATTAGTAATTCTTGGCTTATGTGGTTAATAAT-
TAATCTTGTACAAATGGCCCCGATTTCAGCTATG GT
TAGAATGTACATCTTCTTTGCATCATTTTATTATG
TATGGAAAAGTTATGTGCATGTTGTAGACGGTT
GTAATTCATCAACTTGTATGATGTGTTACAAACG-
TAATAGAGCAACAAGAGTCGAATGTACAACTAT-
TGT TAATGGTGTTAGAAGGTCCTTTTATGTCTATGC-
TAATGGAGGTAAAGGCTTTTGCAAACTACACAAT-
TGG AATTGTGTTAATTGTGATACATTCTGTGCTGG-
TAGTACATTTATTAGTGATGAAGTTGCGAGAGAC-
TTGT CACTACAGTTTAAAAGACCAATAAATCCTA-
CTGACCAGTCTTCTTACATCGTTGATAGTGTTACA-
GTGAA GAATGGTTCCATCCATCTTTACTTTGATAA-
AGCTGGTCAAAAGACTTATGAAAGACATTCTCTCT-
CTCAT TTTGTTAACTTAGACAACCTGAGAGCTAA-
TAACACTAAAGGTTCATTGCCTATTAATGTTATAGT-
TTTTG ATGGTAAATCAAAATGTGAAGAATCATCTG-
CAAAATCAGCGTCTGTTTACTACAGTCAGCTTATG-
TGTCA ACCTATACTGTTACTAGATCAGGCATTAGT-
GTCTGATGTTGGTAGTGCGGAAGTTGCAGT-
TAAAATG TTTGATGCTTACGTTAATACGTTTTCATC
AACTTTTAACGTACCAATGGAAAAACTCAAAA-
CACTAGTTG CAACTGCAGAAGCTGAACTTGCAAA-
GAATGTGTCCTTAGACAATGTCTTATCTACTTTTAT-
TCAGCAGC TCGGCAAGGGTTTGTTGATTCAGAT-
GTAGAAACTAAAGATGTTGTTGAATGTCTTAAAT-
TGTCACATCAA TCTGACATAGAAGTTACTGGCGA-
TAGTTGTAATAACTATATGCTCACCTATAACAAAG-
TTGAAAACATGA CACCCCGTGACCTTGGTGCTTGT-
ATTGACTGTAGTGCGCGTCATATTAATGCGCAGGT-
AGCAAAAAGTCA CAACATTGCTTTGATATGGAAC-
GTTAAAGATTTCATGTCATTGTCTGAACAACTACG-
AAAACAAATACGT AGTGCTGCTAAAAAGAATAA-
CTTACCTTTTAAGTTGACATGTGCAACTACTAGAC-
AAGTTGTTAATGTTG TAACAACAAAGATAGCACT-
TAAGGGTGGTAAAATTGTTAATAATTGGTTGAAGC-
AGTTAATTAAAGTTAC ACTTGTGTTCCTTTTGTT-
GCTGCTATTTTCTATTTAATAACACCTGTTCATGT-
CATGTCTAAACATACT GACTTTTCAAGTGAAAT-
CATAGGATACAAGGCTATTGATGGTGGTGTCACTC-
GTGACATAGCATCTCACAG ATACTTGTTTTGCTAA-
CAAACATGCTGATTTTGACACATGGTTTAGCCAG-
CGTGGTGGTAGTTATACTAA TGACAAAGCTTGCCC-
ATTGATTGCTGCAGTCATAACAAGAGAAGTGGGT-
TTTGTCGTGCCTGGTTTGCCTGGCACGATATTACG- CACAACTAATGGTGACTTTTTGCATTTCTTACCT-
AGAGTTTTAGTGCAGTTGGTA ACATCTGTTACAC-
ACCATCAAAACTTATAGAGTACACTGACTTTGCAA-
CATCAGCTTGTGTTTTGGCTGCTGAATGTACAAT TT-
TTAAAGATGCTTCTGGTAAGCCAGTACCATATTGT-
TATGATACCAATGTACTAGAA GGTTCTGTTGCTTAT-
GAAAGTTTACGCCCTGACACACGTTATGTGCTCAT-
GGATGGCTCTATTATTCAAT TTCCTAACACCTACCT
TGAAGGTTCTGTTAGAGTGGTAACAACTTTTGAT-
TCTGAGTACTGTAGGCACGG CACTTGTGAAAGAT
CAGAAGCTGGTGTTTGTGTATCTACTAGTGGTAGA
TGGGTACTTAACAATGATTAT TACAGATCTTTAC C
AGGAGTTTTCTGTGGTGTAGATGCTGTAAATTTACT-
TACTAATATGTTACACCAC TAATTCAACCTATTG
GTGCTTTGGACATATCAGCATCTATAGTAGCT GGTG
GTATTGTAGCTATCGTAGT AACATGCCTTGCCTACT-
ATTTTATGAGGTTTAGAAGAGCTTTTGGTGAATAC
AGTCATGTAGTTGCCTTT AATACTTTACTATTCCTT
ATGTCATTCACTGTACTCTGTTTAACACCAGTTTA
CTCATTCTTACCTGGTG TTTATTCTGTTATTTACT TG
TACTTGACATTTTATCTTACTAATGATGTTTCTTTTT-
TAGCACATATTCA GTGGATGGTTATGTTCACACCTT-
TAGTACCTTTCTGGGATAACAATTGCTTATATCATTT
GTATTTCCACA AAGCATTTCTATTGGTTCTTTAGT
AATTACCTAAAGAGACGTGTAGTCTTTAATGGTGT
TTCCTTTAGTA CTTTTGAAGAAGCTGCGCTGTG CA
CCTTTTTGTTAAATAAAGAAATGTATCTAAAGTTG C
G TAGTGATGT GCTATTACCTCTTACGCAATATAATA-
GATACTTAGCTCTTTATAATAAGTACAAGTATTTTA G
TGGAGCA ATGGATACAACTAGCTACAGAGAA GC
TG CTTGTTGTCATCTCGCAAAGGCTCTCAATGA CT
TCAGTAACT CAGGTTCTGATGTTCTTACCAACCA
CCACAAACCTCTATCACCTCAGCTGTTTTGCAG AG
TGGTTTTAG AAAAATGGCATTCCCATCTGGT AAA
GTTGAGGGTTGTATGGTACAAGTAACTTGTGGTA-
CAACTACACTT AACGGTCTTTGGCTTGATGACGT A
GTTTACTGTCCAAGACATGTGATCTGCACCTCTG A
AGACATGCTTA ACCCTAATTATGAAGATTACTCAT-
TCGTAAG TCTAATCATAATTTCTTGGTACAGGCT G
GTAATGTTCA ACTCAGGGTTATTGGACATTCTAT G
CAAAATTGTGTACTTAAGCTTAAGGTTGATACAGC-
CAATCCTAAG ACACCTAAGTATAAGTTTGTTCGC
ATTCAACCAGGACAGACTTTTTCAGTGTTAGCT
TGTTACAATGGTT CACCATCTGGTGTTTACCAAT GT
GCTATGAGGCCCAATTTCACTATTAAGGGGTTCAT-
TCCTTAATGGTTC ATGTGGTAGTGTTGGTTTTAAC
ATAGATTATGACTGTGTCTCTTTTTGTTACATGCAC-
CATATGGAATTA CCAACTGGAGTTCATGCTG GC
ACAGACTTAGAAGGTAACTTTTATGGACCTT TTGT
TGACAGGCAAACAG CACAAGCAGCTGGTACGG A
CACAACTATTACAGTTAATGTTTTAGCTTGG TTGTA
CGCTGCTGTTATAAA TGGAGACAGGTGGTTTCTCA
ATCGATTTACCACAACTCTTAATGACTTTAACCTTG
TGGCTATGAAGTACAATTATGAACCTCTAACACA
AGACCATGTTGACATACTAGGACCTCTTTCTGCT-
CAAACTGGAATTGCCG TTTTAGATATGTGTGCTTC
ATTAAAAGAATTACTGCAAAATGGTATGAATGGA
CGTACCATATTGGGTAG TGCTTTATTAGAAGATGA
ATTTACACCTTTTGATGTTGTTAGACAATGCTC A G
GTGTTACTTTCCAAAGT GCAGTGAAAAGAACAAT-
CAAGGGTACACCACCACTGGTTGTTACTCACAATTT
TGACTTCACTTTTAGTTT TAGTCCAGAGTACTCAA
TGGTCTTTGTTCTTTTTTTGTATGAAAATGCCTTTT-
TACCTTTTGCTATGGG TATTATTGCTATGTCTGCTT
TTGCAATGATGTTTGTCAAACATAAGCATGCATTT
CTCTGTTTGTTTTTG TTACCTTCTCTTGCCACTG TAG CTTATTTTAATATGGTCTATATGCCTGCTAGTT-
GGGTGATGCGTATTA TGACATGGTTGGATATGGTT-
GATACTAGTTTGTCTGGTTTTAAGCTAAAAGAC TG-
T GTTATGTATGCATC AGCTGTAGTGTTACTAATCCT-
TATGACAGCAAGAACTGTGTATGATGATGGTGCT-
AGGAGAGTGTGGACA CTTATGAATGTCTTGA-CAC-
TCGTTTATAAAGTTTATTATGGTAATGCTTTAGAT-
CAAGCCATTTCCATGT GGGCTCTTATAATCTCTGTT-
ACTTCTAACTACTCAGGTGTAGTTACAACTGTCAT-
GTTTTTGGCCAGAGG TATTGTTTTTATGTGTGTTG-
AGTATTGCCCTATTTTCTTCATAACTGGTAATACAC-
TTCAGTGTATAATG CTAGTTTATTGTTTCTTAGGCT-
ATTTTTGTACTTGTTACTTTGGCCTCTTTTGTTTACT-
CAACCGCTACTTTAGACTGACTCTTGGTGTTTA TG-
ATTACTTAGTTTCTACACAGGAGTTTAGATATATGA-
ATTCACAGGG ACTACTCCCACCCAAGAATAGCATA-
GATGCCTTCAAACTCAACATTAAATTGTTGGGTGT-
TGGTGGCAAA CCTTGTATCAAAGTAGCCACTGTA-
CAGTCTAAAATGTCAGATGTAAAGTGCACATCAG-
TAGTCTTACTCT CAGTTTTGCAACAACTCAGAGTA-
GAATCATCATCTAAATTGTGGGCTCAATGTGT- CCA-
GTTACACAATGA CATTCTCTTAGCTAAAGATACTA-
CTGAAGCCTTTGAAAAAATGGTTTCACTACTTTC-
TGTTTTGCTTTCC ATGCAGGGTGCTGTAGACATAA-
ACAAGCTTTGTGAAGAAATGCTGGACAACAGGG-
CAACCTTACAAGCTA TAGCCTCAGAGTTTAGTTC-
CCTTCCATCATATGCAGCTTTTGCTACTGCTCAAGA-
AGCTTATGAGCAGGC TGTTGCTAATGGTGATTCT-
GAAGTTGTTCTTAAAAAGTTGAAGAAGTCTTT-
GAATGTGGCTAAATCTGAA TTTGACCGTGATGCA-
GCCATGCAACGTAAGTTGGAAAAGATGGCTGAT-
CAAGCTATGACCCAAATGTATA AACAGGCTAGAT-
CTGAGGACAAGAGGGCAAAAGTTACTAGTGCTAT-
GCAGACAATGCTTTTCACTATGCT TAGAAAGTTG-
GATAATGATGCACTCAACAACATTATCAACAATG-
CAAGAGATGGTTGTGTTCCCTTGAACATAATACCT-
CTTACAACAGCAGCCAAACTAATGGTTGTCATAC-
CAGACTATAACACATATAAAAATACGT GTGATGGT-
ACAACATTTACTTATGCATCAGCATTGTGGGAAAT-
CCAACAGGTTGTAGATGCAGATAGTAA AATTGTT-
CAACTTAGTGAAATTAGTATGGACAATTCACCTAAT-
TTAGCATGGCCTCTTATTGTAACAGCT TTAAGGGC-
CAATTCTGCTGTCAAATTACAGAATAATGAGCTT-
AGTCCTGTTGCACTACGACAGATGTCTTGTGCT GC-
CGGTACTACACAAACTGCTTGCACTGATGACAAT-
GCGTTAGCTTACTACAACACAACAAAGGG AGGTA-
GGTTTGTACTTGCACTGTTATCCGATTTACAGGAT-
TTGAAATGGGCTAGATTCCCTAAGAGTGAT GGAA-
CTGGTACTATCTATACAGAACTGGAACCACCTTGT-
AGGTTTGTTACAGACACACCTAAAGGTCCTA AAGT-
GAAGTATTTATACTTTATTAAAGGATTAAACAAC-
CTAAATAGAGGTATGGTACTTGGTAGTTTAGCTG-
CCACAGTACGTCTACAAGCTGGTAATGCAACAG-
AAGTGCCTGCCAATTCAACTGTATTATCTTTCTGT
GCTTTTGCTGTAGATGCTGCTAAAGCTTACAAA-
GATTATCTAGCTAGTGGGGACAACCAATCACTAA-
TT GTGTTAAGATGTTGTGTACACACACTGGTACT-
GGTCAGGCAATAACAGTTACACCGGAAGCCAATA-
TGGA TCAAGAATCCTTTGGTGGTGCATCGTGTTGT-
CTGTACTGCCGTTGCCACATAGATCATCCAAATCC-
TAAA GGATTTTGTGACTTAAAAGGTAAGTATGTA-
CAAATACCTACAACTTGTCTAATGACCCTGTG-
GGTTTTACACTTAAAAACACAGTCTGTACCGTC-
TGCGGTATGTGGAAAGGTTATGGCTGTAGTTGT-
GATCAACTCCG CGAACCCATGCTTCAGTCAGCTG-
ATGCACAATCGTTTTTAAACGGGTTTGCGGTGTAA-
GTGCAGCCCGTCTTACACCGTGCGGCAC AGGCAC- TAGTACTGATGTCGTATACAGGGCTTTTGACATCTA-
CAATGATAAAGT AGCTGGTTTTGCTAAATTCCTAA-
AAACTAATTGTTGTCGCTTCCAAGAAAAGGAC-
GAAGATGACAATTTA ATTGATTCTTACTTTGTAGT-
TAAGAGACACACTTTCTCTAACTACCAACATGAA-
GAAACAATTTATAATT TACTTAAGGATTGTCCAGC-
TGTTGCTAAACATGACTTCTTTAAGTTTAGAATA-
GACGGTGACATGGTACCACATATATCACGTCAA-
CGTCTTACTAAATACACAATGGCAGACCTCGTC-
TATGCTTTAAGGCATTTTGAT GAAGGTAATTGTGA-
CACATTAAAAGAAATACTTGTCACATACAATTGTT-
GTGATGATGATTATTTCAATA AAAAGGACTGGTAT-
GATTTTGTAGAAAACCCAGATATATTACGCGTATA-
CGCCAACTTAGGTGAACGTGT ACGCCAAGCTTT-
GTTAAAAACAGTACAATTCTGTGATGCCATGCG-
AAATGCTGGTATTGTTGGTGTACTG ACATTAGATA-
ATCAAGATCTCAATGGTAACTGGTATGATTTCGGT-
GATTTCATACAAACCACGCCAGGTA GTGGAGTTC-
CTGTTGTAGATTCTTATTATTCATTGTTAATGCCTAT-
ATTAACCTTGACCAGGGCTTTAAC TGCAGAGTCA-
CATGTTGACACTGACTTAACAAAGCCTTACATTA-
AGTGGGATTTGTTAAAATATGACTTC ACGGAAGA-
GAGGTTAAAACTCTTTGACCGTTATTTTAAATAT-
TGGGATCAGACATACCACCCAAATTGTG TTAACT-
GTTTGGATGACAGATGCATTCTGCATTGTGCAAA-
CTTTAATGTTTTATTCTCTACAGTGTTCCCACCTA-
CAAGTTTTGGACCACTAGTGAGAAAAATATTTGTT-
GATGGTGTTCCATTTGTAGTTTCAACTGGATACCA-
CTTCAGAGAGCTAGGTGTTGTACATAATCAGGAT-
GTAAACTTACATAGCTCTAGACTTAGTTTTAAGG-
AATTACTTGTGTATGCTGCTGACCCTGCTATGCAC-
GCTGCTTCTGGTAATCTATTACTAGATAAACGCAC-
TACGTGCTTTTCAGTAGCTGCACTTACTAACAATG
TTGCTTTTCAAACTGTCAAACCCGGTAATTTT AAC-
AAAGACTTCTATGACTTTGCTGTGTCTAAGGGTT-
TCTTTAAGGAAGGAAGTTCTGTTGAATTAAAAC
ACTTCTTCTTTGCTCAGGATGGTAATGCTGCTA-
TCAGCGATTATGACTACTATCGTTATAATCTACCAAC
AATGTGTGATATCAGACAACTACTATTTGTAGTT-
GAAGTTGTTGATAAGTACTTTGATTGTTACGATGGT-
GGCTGTATTAATGCTAACCAAGTCATCGTCAACAA-
CCTAGACAAATCAGCTGGTTTTCCATTTAATAAAT
GGGGTAAGGCTAGACTTTATTATGATTCAATGAGT-
TATGAGGATCAAGATGCACTTTTCGCATATACAAA
ACGTAATGTCATCCCTACTATAACTCAAATGAATCT-
TAAGTATGCCATTAGTGCAAAGAATAGAGCTCGC
ACCGTAGCTGGTGTCTCTATCTGTAGTACTATGAC-
CAATAGACAGTTTCATCAAAAATTATTGAAATCAA
TAGCCGCCACTAGAGGAGCTACTGTAGTAATTG-
GAACAAGCAAATTCTATGGTGGTTGGCACAACA-
TGTT AAAAACTGTTTATAGTGATGTAGAAAACCCT-
CACCTTATGGGTTGGGATTATCCTAAATGTGATAG-
AGCC ATGCCTAACATGCTTAGAATTATGGCCTCAC-
TTGTTCTTGCTCGCAAACATACAACGTGTTGTAG-
CTTGTCACACCGTTTCTATAGATTAGCTAATGAG-
TGTGCTCAAGTATTGAGTGAAATGGTCATGTGT-
GGCGGTTC ACTATATGTTAAACCAGGTGGAACCTC-
ATCAGGAGATGCCACAACTGCTTATGCTAATAGT-
GTTTTTAACATTTGTCAAGCTGTCACGGCCAATGT-
TAATGCACTTTTATCTACTGATGGTAACAAAAT-
TGCCGATAAGTATGTCCGCAATTTACAACACAGA-
TTTATGAGTGTCTCTATAGAAATAGAGATGTTGACA-
CAGACTTTGT GAATGAGTTTTACGCATATTTGCGT-
AAACATTTCTCAATGATGATACTCTCTGACGATGC-
TGTTGTGTGTTTCAATAGCACTTATGCATCTCAAG-
GTCTAGTGGCTAGCATAAAGAACTTTAAGTCAGT- TCTTTATTATCAAAACAATGTTTTTATGTCTGAAG-
AAAATGTTGGACTGAGACTGACCTTACTAAAG-
CCTCATGAATT TTGCTCTCAACATACAATGCTAGT-
TAAACAGGGTGATGATTATGTGTACCTTCCTTAC
CCAGATCCATCA AGAATCCTAGGGGCCGGC TGTTT
TGTAGATGATATCGTAAAAACAGATGGTACACTTAT-
GATTGAACGGT TCGTGTCTTTAGCTATAGATGCT-
TACCCACTTACTAAACATCCTAATCAGGAGTATGCT-
GATGTCTTTCATTTGTACTTACAATACATAAGAAA
GCTACATGATGAGTTAACAGGACACATGTTAGA-
CATGTATTCTGTTATGCTTACTAATGATAACACTTC
AAGGTATTGGGAACCTGAGTTTATGAGGCTATG-
TACACACCGCATA CAGTCTTACAGGCTGTTGGGG-
CTTGTGTTCTTTGCAATTCACAGACTTCATTAAGA-
TGTGGTGCTTGCATACGTAGACCATTCTTATGT TGT-
AAATGCTGTTACGACCATGTCATATCAACATCACAT-
AAATTAGTCTTG TCTGTTAATCCGTATGTTTGCAAT-
GCTCCAGGTTGTGATGTCACAGATGTGACTCAACT-
TTACTTAGGAG GTATGAGCTATTATTGTAAATCAC-
ATAAACCACCCATTAGTTTTCCATTGTGTGCTAAT-
GGACAAGTTTT TGGTTTATATAAAAATACATGTGT
TGGTAGCGATAATGTTACTGACTTTAATGCAATTGC
AACATGTGAC TGGACAAATGCTGGTGATTACATTT-
TAGCTAACACCTGTACTGAAAGACTCAAGCTTTT
GCAGCAGAAA CGCTCAAAGCTACTGAGGAGACAT-
TTAAACTGTCTTATGGTATTGCTACTGTACGTGAA
GTGCTGTCTGA CAGAGAATTACATCTTTCATGGGA
AGTTGGTAAACCTAGACCACCACTTAACCGAAAT-
TATGTCTTTACT GGTTATCGTGTAACTAAAAA CAG
TAAAGTACAAATAGGAGAGTACACCTTTGAAAA AG
GTGACTATGGTG ATGCTGTTGTTTACCGAGGTACA
ACAACTTACAAATTAAATGTTGGTGATTATTTTGTG
CTGACATCACA TACAGTAATGCCATTAAGTGCACC-
TACACTAGTGCCACAAGAGCACTATGTTAGAATTA
CTGGCTTATAC CCAACACTCAATATCTCAGATGAGT
TTTCTAGCAATGTTGCAAATTATCAAAAGGTTGGTA
TGCAAAAGT ATTCTACACTCCAGGGACCACCTGGT
ACTGGTAAGAGTCATTTTGCTATTGGCCTAGCTCTC-
TACTACCC TTCTGCTCGCATAGTGTATACAGCTTG
CT CTCATGCCGCTGTTGATGCACTATGTGAGAAGG-
CATTAAAA TATTTGCCTATAGATAAATGTAGT AGAA
TTATACCTGCACGTGCTCGTGTAGAGTGTTTTGA-
TAAATTCAAAGTGAATTCAACATTAGAACAGTATG
TCTTTTGTACTGTAAATGCATTGCCTGAGACGAC
AGCAGATATAGTTGTCTTTGATGAAATTTCAAT GGC
CACAAATTATGATTTGAGTGTTGTCAATGCCAGAT-
TACGTGCT AAGCACTATGTGTACATTGGCGACCCT
GCTCAATTACCTGCACCACGCACATTGCTAACTA
AGGGCACAC TAGAACCAGAATATTTCAATTCAGTG
TGTAGACTTATGAAAACTATAGGTCCAGACATGTT
CCTCGGAAC TTGTCGGCGTTGTCCTGCTGAAATTG
TTGACACTGTGAGTGCTTTGGTTTATGATAATAAGC
TTAAAGCA CATAAAGACAAATCAGCTCAATGCTT-
TAAAATGTTTTATAAGGGTGTTATCACGCATGATGT
TTCATCTGCAATTAACAGGCCACAAATAGGCG TG
GT AAGAGAATTCCTTACACGTAACCCTGCTTGGAG
AAAAGCTGT CTTTATTTCACCTTATAATTCACA GA
ATGCTGTAGCCTCAAAGATTTTGGGACTACCAACT-
CAAACTGTT GATTCATCACAGGGCTCAGAATATGA
CTATGTCATATTCACTCAAACCACTGAAACAGCT-
CACTCTTGTA ATGTAAACAGATTTAATGTTGCTAT-
TACCACAGCAAAAGTAGGCATACTTTGCATAATGTC
TGATAGAGA CCTTTATGACAAGTTGCAATTTACAA
GTCTTGAAATTCCACGTAGGAATGTGGCAACTTTA-
CAAGCTGAA AATGTAACAGGACTCTTTAAAGATTG
TAGTAAGGTAATCACTGGGTTACATCCTACACAGG
CACCTACAC ACCTCAGTGTTGACACTAAATTCAA A ACTGAAGGTTTATGTGTTGACATACCTGGCATACC
TAAGGACAT GACCTATAGAAGACTCATCTCTATGA
TGGGTTTTAAAATGAATTATCAAGTTAATGGTTAC
CCTAACATG TTTATCACCCGCGAAGAAGCTATAA-
GACATGTACGTGCATGGATTGGCTTCGATGTC GAG
GGGTGTCATG CTACTAGAGAAGCTGTTGGTAC-
CAATTTACCTTTACAGCTAGGTTTTTCTACAGGTGT-
TAACCTAGTTGC TGTACCTACAGGTTATGTTGATA-
CACCTAATAATACAGATTTTTCCAGAGTTAGTGCT-
AAACCACCGCCT GGAGATCAATTTAAACACCTCAT-
ACCACTTATGTACAAAGGACTTCCTTGGAATGTA
GTGCGTATAAAGA TTGTACAAATGTTAAGTGA CAC
ACTTAAAAATCTCTCTGACAGAGTCGTATTTGTCT-
TATGGGCACATGG CTTTGAGTTGACATCTATGAA
GTATTTTGTGAAAATAGGACCTGAGCGCACCTGT
TGTCTATGTGATAGA CGTGCCACATGCTTTTCCAC
TGCTTCAGACACTTATGCCTGTTGGCATCATTCTAT-
TGGATTTGATTACG TCTATAATCCGTTTATGATTGA
TGTTCAACAATGGGGTTTTACAGGTAACCTACAAA
GCAACCATGATCT GTATTGTCAAGTCCATGGT AAT
GCACATGTAGCTAGTTGTGATGCAATCATGACTA
GGTGTCTAGCTGTC CACGAGTGCTTTGTTAAGCGT
GTTGACTGGACTATTGAATATCCTATAATTGGTGAT-
GAACTGAAGATTA ATGCGGCTTGTAGAAAGGTTCA
ACACATGGTTGTTAAAGCTGCATTATTAGCAGACAA
ATTCCCAGTTCT TCACGACATTGGTAACCCTAAA
GCTATTAAGTGTGTACCTCAAGCTGATGTAGAATG-
GAAGTTCTATGAT GCACAGCCTTGTAGTGAC AAA
GCTTATAAAATAGAAGAATTATTCTATTCTTATGCC
ACACATTCTGACA AATTCACAGATGGTGTATGCCT-
ATTTTGGAATTGCAATGTCGATAGATATCCTGCTAA
TTCCATTGTTTG TAGATTTGACACTAGAGTGCTATC
TAACCTTAACTTGCCTGGTTGTGATGGTGGCAGTT
TGTATGTAAAT AAACATGCATTCCACACACCAGC
TTT TGATAAAAGTGCTTTTGTTAATTTAAAACAAT-
TACCATTTTTCT ATTACTCTGACAGTCCATGTGAGT
CTCATGGAAAACAAGTAGTGTCAGATATAGATTAT
GTACCACTAAA GTCTGCTACGTGTATAAC ACGT
TGC AATTTAGGTGGTGCTGTCTGTAGACATCATGC
TA ATGAGTACAGA TTGTATCTCGATGCTTATAACAT-
GATGATCTCAGCTGGCTTTAGCTTGTGGGTTTACA
AACAATTTGATA CTTATAACCTCTGGAACACTTTTA-
CAAGACTTCAGAGTTTAGAAAATGTGGCTTTTAA
TGTTGTAAATAA GGGACACTTTGATGGACAAC AGG
GTGAAGTACCAGTTTCTATCATTAATAACACTGTT-
TACACAAAAGTT GATGGTGTTGATGTAGAATTGT
TTGAAAATAAAACAACATTACCTGTTAATGTAGCAT-
TTGAGCTTTGGG CTAAGCGCAACATTAAA CCAGT
ACCAGAGGTGAAAATACTCAATAATTTGGGTGT
GGACATTGCTGCTAA TACTGTGATCTGGGACTACA
AAAGAGATGCTCCAGCACATATATCTACTATTGGTG
TTTGTTCTATGACT GACATAGCCAAGAAACCAACT-
GAAACGATTTGTGCACCACTCACTGTCTTTTTTGA
TGGTAGAGTTGATG GTCAAGTAGACTTATTTAGAA
ATGCCCGTAATGGTGTTCTTATTACAGAAGGTA GT
GTTAAAGGTTTACA ACCATCTGTAGGTCCCAAA
CAAGCTAGTCTTAATGGAGTCACATTAATTGGAGA
AGCCGTAAAAACACAG TTCAATTATTATAAGA AA
GTTGATGGTGTTGTCCAACAATTACCTGAAACTTAC
TTTACTCAGAGTAGAA ATTTACAAGAATTTAAA CC
CAGGAGTCAAATGGAAATTGATTTCTTAGAATTAG
CTATGGATGAATTCAT TGAACGGTATAAATTAGA
AGGCTATGCCTTCGAACATATCGTTTATGGAGATTT-
TAGTCATAGTCAGTTA GGTGGTTTACATCTACTGAT-
TGGACTAGCTAAACGTTTTAAGGAATCACCTTTT- GAATTAGAAGATTTTA TTCCTATGGACAGTACAGT-
TAAAAACTATTTCATAACAGATGCGCAAACAGGTT-
CATCTAAGTGTGTGTG TTCTGTTATTGATTTATTAC
TTGATGATTTTGTTGAAATAATAAAATCCCAAGATT-
TATCTGTAGTTTCT AAGGTTGTCAAAGTGACTATTG
ACTATACAGAAATTTCATTTATGCTTTGGTGTAAA-
GATGGCCATGTAG AAACATTTTACCCAAAATTACA
ATCTAGTCAAGCGTGGCAACCGGGTGTTGCTATGC
CTAATCTTTACAA AATGCAAAGAATGCTATTAGAAA
AGTGTGACCTTCAAAATTATGGTGATAGTGCAA-
CATTACCTAAAGGC ATAATGATGAATGTCGCA AAA
TATACTCAACTGTGTCAATATTTAAACACATTAA-
CATTAGCTGTACCCT ATAATATGAGAGTTATACATTT
TGGTGCTGGTTCTGATAAAGGAGTTGCACCAGGTA-
CAGCTGTTTTAAGACAGTGGTTGCCTACGGGTAC-
GCTGCTTGTCGATTCAGATCTTAATGACTTTGTCT-
CTGATGCAGATTCA ACTTTGATTGGTGATTGTG CA
ACTGTACATACAGCTAATAAATGGGATCTCATTATT-
AGTGATATGTACG ACCCTAAGACTAAAAATGTTA-
CAAAAGAAAATGACTCTAAAGAGGGTTTTTTCACT-
TACATTTGTGGGTT TATACAACAAAAGCTAGCTC
TTGGAGGTTCCGTGGCTATAAAGATAACAGAACAT-
TCTTGGAATGCTGAT CTTTATAAGCTCATGGGA CAC
TTCGCATGGTGGACAGCCTTTGTTACTAATGTGAA
TGCGTCATCATCTG AAGCATTTTTAATTGGATGTAA
TTATCTTGGCAAACCACGCGAACAAATAGATGGT-
TATGTCATGCATGC AAATTACATATTTTGGAGGAA
TACAAATCCAATTCAGTTGTCTTCCTATTCTTTAT-
TTGACATGAGTAAA TTTCCCCTTAAATTAAGGG
GTACTGCTGTTATGTCTTTAAAAGAAGGTCAAAT-
CAATGATATGATTTTAT CTCTTCTTAGTAAAGGTA-
GACTTATAATTAGAGAAAACAACAGAGTTGTTAT-
TTCTAGTGATGTTCTTGT TAACAACTAA Assays and Kits Another aspect of the technology described herein relates to kits for detecting SARS-coronavirus-2. Provided herein are kit components that can be included in one or more of the kits described herein.

In some embodiments of any of the aspects, the kit comprises at least one set of primers for LAMP. In some embodiments of any of the aspects, the set of LAMP primers is specific to the target viral RNA. In some embodiments of any of the aspects, the set of amplification primers is specific (i.e., binds specifically through complementarity) to cDNA, in other words, the DNA produced in the RT step that is complementary to the target viral RNA. The set of primers can be specific to any region of the target viral RNA. SEQ ID NOs: 1-8 include non-limiting examples of primers that are specific for SARS-CoV-2.

In another aspect, the kit provided herein is a kit for detecting a SARS-CoV viral nucleic acid in a sample, the kit comprising:
(i) a first nucleic acid strand (first primer) comprising a nucleotide sequence CGGTGGACAAATTGTCAC (SEQ ID NO: 1);
(ii) a second nucleic acid strand (second primer) comprising a nucleotide sequence of CTTCTCTGGATT-TAACACACTT (SEQ ID NO: 2)
(iii) a third nucleic acid strand (third primer) comprising a nucleotide sequence of TCAGCACACAAAGC-CAAAAATTTATCTGTGCAAAGGAAATTAAGG AG (SEQ ID NO: 3) or TCAGCACACAAAGC-CAAAAATTTATTTTTCTGTGCAAAGGAAATTA AGGAG (SEQ ID NO: 4);
(iv) a fourth nucleic acid strand (fourth primer) comprising a nucleotide sequence of TATTGGTG-GAGCTAAACTTAAAGCCCTGTACAATCCCTTT-GAGTG (SEQ ID NO: 5) or TATTGGT-GGAGCTAAACTTAAAGCCTTTTCTGTACAATC-CCTTTGA GTG (SEQ ID NO: 6);
(v) a fifth nucleic acid strand (fifth primer) comprising a nucleotide sequence of TTACAAGCTTAAA-GAATGTCTGAACACT (SEQ ID NO: 7); and
(vi) a sixth nucleic acid strand (sixth primer) comprising a nucleotide sequence of TTGAATTAGGTGAAA-CATTTGTCACG (SEQ ID NO: 8).

In some embodiments of any of the aspects, the kit further comprises one or more nucleic acid strands comprising a nucleotide sequence substantially complementary to SEQ ID NO: 1, SEQ ID NO: 2, SEQ ID NO: 3, SEQ ID NO: 4, SEQ ID NO: 5, SEQ ID NO: 6, SEQ ID NO: 7, and/or SEQ ID NO: 8.

In some embodiments of any of the aspects, the primers are provided at a sufficient concentration, e.g., 1 µM to 20 µM to be added to the reaction mixture. As a non-limiting example, the primers are provided at a concentration of at least 1 µM, at least 2 µM, at least 3 µM, at least 4 µM, at least 5 µM, at least 6 µM, at least 7 µM, at least 8 µM, at least 9 µM, at least 10 µM, at least 11 µM, at least 12 µM, at least 13 µM, at least 14 µM, at least 15 µM, at least 16 µM, at least 17 µM, at least 18 µM, at least 19 µM, at least 20 µM, at least 21 µM, at least 22 µM, at least 23 µM, at least 24 µM, at least 25 µM, at least 26 µM, at least 27 µM, at least 28 µM, at least 29 µM, at least 30 µM, at least 35 µM, at least 40 µM, at least 45 µM, at least or at least 50 µM. In some embodiments of any of the aspects, the primers comprise any combination of the primers listed in Table 1 (e.g., SEQ ID NOs: 1-8) or any combination of primers that are at least 95% identical to one of SEQ ID NO: 1-8 that maintains the same function. In some embodiments of any of the aspects, the primers are provided as a stock solution, e.g., the reaction mixture of Table 4 (see EXAMPLE 1).

In some embodiments of any of the aspects, the kit comprises a detergent or a lysis buffer.

In some embodiments of any of the aspects, the kit comprises one or more reagents or buffers for loop-mediated isothermal amplification of a nucleic acid. In some embodiments of any of the aspects, the kit comprises a buffer solution for loop-mediated isothermal amplification of a nucleic acid.

In some embodiments of any of the aspects, the kit comprises a polymerase enzyme.

In some embodiments of any of the aspects, the kit comprises dNTPs.

In some embodiments of any of the aspects, the kit comprises a reverse transcriptase. In some embodiments of any of the aspects, the kit further comprises a set of reverse transcription (RT) primers. In some embodiments of any of the aspects, the set of RT primers comprises primers that bind to target RNA and non-target RNA in the sample, i.e., "general" primers. In some embodiments of any of the aspects, the set of RT primers comprises random hexamers, i.e., a mixture of oligonucleotides representing all possible hexamer sequences. In some embodiments of any of the aspects, the set of RT primers comprises oligo(dT) primer, which bind to the polyA tails of mRNAs or viral transcripts. In some embodiments of any of the aspects, the set of RT primers is specific to the target viral RNA.

In some embodiments of any of the aspects, the kit comprises a colorimetric reagent.

In some embodiments of any of the aspects, the kit comprises a reference sample. In some embodiments of any of the aspects, the kit comprises a positive control. In some embodiments of any of the aspects, the positive control is a target viral nucleic acid sequence provided herein. In some embodiments of any of the aspects, the positive control nucleic acid sequence comprises a portion of any one of SEQ ID NOs: 9-10. In some embodiments of any of the aspects, the kit comprises a negative control.

In some embodiments of any of the aspects, the kit comprises a reaction vessel or test tube. In some embodiments of any of the aspects, the kit comprises a nasal swab or a throat swab. In some embodiments of any of the aspects, the kit comprises packaging and materials.

In another aspect, provided herein is an assay for detecting a SARS-coronavirus-2 nucleic acid in a sample, the assay comprising:
  (a) contacting a sample with a composition or kit provided herein to produce a reaction mixture, wherein the reaction mixture comprises one or more reagents or buffers for loop-mediated isothermal amplification of a nucleic acid; and
  (b) heating the reaction mixture of step (a) to a temperature of about 65° C. for a period of time,
wherein a color change in the reaction mixture indicates the presence of a SARS-coronavirus-2 in the sample.

In some embodiments of any of the aspects, the assay further comprises cooling the reaction mixture from step (b) to room temperature.

In some embodiments of any of the aspects, the assay further comprises obtaining the biological sample from a subject having or suspected of having a SARS-coronavirus-2 infection.

Diagnosing and Treating a Viral Infection

Provided herein are compositions, methods, assays, and kit for the diagnosis and treatment of a viral infection. In one aspect, provided herein is a method of treating a viral infection, the method comprising:
  (a) obtaining a sample from a subject;
  (b) contacting the sample from (a) with any one of the compositions provided herein, wherein when a sample has a color change output, the color change output indicates that the sample is positive for a viral nucleic acid; and
  (c) when step (b) indicates that the sample is positive for a viral nucleic acid, administering to the subject a treatment for a viral infection.

In some embodiments of any of the aspects, the methods and assays provided herein are performed repeatedly on one sample. In some embodiments of any of the aspects, the methods and assays provided herein are performed repeatedly on different samples from the same subject. For example, at different time points.

In another aspect, the compositions, assays, and kits provided herein are used to determine whether a subject has a viral infection. In another aspect, the compositions, assays, and kits provided herein are used to determine whether a subject has a severe acute respiratory infection. In another aspect, the compositions, assays, and kits provided herein are used to determine whether a subject has COVID 19.

In some embodiments of any of the aspects, the viral infection is an infection of a tissue selected from the group consisting of: central nervous system tissue, eye tissue, upper respiratory system tissue, lower respiratory system tissue, lung tissue, kidney tissue, bladder tissue, spleen tissue, cardiac tissue, gastrointestinal tissue, epidermal tissue, reproductive tissue, nasal cavity tissue, larynx tissue, trachea tissue, bronchi tissue, oral cavity tissue, blood tissue, and muscle tissue.

Non-limiting examples of viral infections include respiratory infections of the nose, throat, upper airways, and lungs such as influenza, pneumonia, coronavirus, SARS, COVID 19, bronchoiolitis, and laryngotracheobronchitis; gastrointestinal infections such as gastroenteritis, rotavirus, norovirus; liver infections such as hepatitis; nervous system infections such as rabies, West Nile virus, encephalitis, meningitis, and polio; skin infections such as warts, blemishes, and chickenpox; placental and fetal viral infections such as Zika virus, Rubella virus, and cytomegalovirus; enteroviruses, conoxsackieviruses; echoviruses, chikungunya virus, Crimean-Congo hemorrhagic fever virus, Japanese encephalitis virus, Rift Valley Fever virus, Ross River virus, louping ill virus, John Cunningham virus, measles virus, lymphocytic choriomeningitis virus, arbovirus, rhinovirus, parainfluenza virus, respiratory syncytial virus, herpes simplex virus, herpes simplex type 1, herpes simplex type 2, human herpesvirus 6, adenovirus, cytomegalovirus, Epstein-Barr virus, mumps virus, influenza virus type A, influenza virus type B, coronavirus, SARS coronavirus, SARS-CoV-2 virus, coxsackie A virus, coxsackie B virus, poliovirus, HTLV-1, hepatitis virus types A, B, C, D, and E, varicella zoster virus, smallpox virus, molluscum contagiosum, human papillomavirus, parvovirus B19, rubella virus, human immunodeficiency virus, rotavirus, norovirus, and astrovirus.

Risk factors for having or developing a viral infection include exposure to the virus, exposure to aerosols comprising the virus or viral particles, exposure or contact with a subject infected with a virus, exposure to contaminated surfaces contacted with a virus, contact with a biological sample or bodily fluid from a subject infected by a virus, sexual intercourse with a subject infected by a virus, needle sharing, blood transfusions, drug use, and any other risk factor known in the art to transmit a virus from one subject to another. Risk factors for a subject can be evaluated, e.g., by a skilled clinician or by the subject.

The symptoms associated with a viral infection vary depending on the type of virus. For example, for an upper respiratory viral infection symptoms include but are not limited to coughing; shortness of breath; fever; and malaise. In severe cases of upper respiratory infections, the subject may not be able to breathe on their own and may require ventilation or intubation procedures. A skilled clinician will be able to identify symptoms of an upper respiratory infection.

For infections that occur in epidemics (e.g., COVID 19), the presence of other similar cases may help doctors and clinicians identify a particular infection. Laboratory diagnosis is important for distinguishing between different viruses that cause similar symptoms, such as COVID-19 (SARS-CoV2) and influenza.

A number of medications for the treatment of a viral infection have been developed. Treatments for infections can include, for example, antiviral medications administered following infection.

The term "therapeutic agent" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians' Desk Reference, and The Pharmacological Basis of Therapeutics, and they include, without limitation, medications, vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject.

Exemplary therapeutic agents and vaccines for the prevention and treatment of infections include but are not limited to penicillin, ceftriaxone, azithromycin, amoxicillin, doxycycline, cephalexin, ciprofloxacin, clindamycin, metronidazole, azithromycin, sulfamethoxazole, trimethoprim, COVID19 vaccine, meningococcal polysaccharide vaccine, tetanus toxoid, cholera vaccine, typhoid vaccine, pneumococcal 7-valent vaccine, pneumococcal 13-valent vaccine, pneumococcal 23-valent vaccine, *haemophilus* b conjugate, anthrax vaccine, imunovir, indinavir, inosine, lopinavir, lovaride, maravirox, nevirapine, nucleoside analogues, oseltamivir, penciclovir, rimantidine, pyrimidine, saquinavir, stavudine, tenofovir, trizivir, tromantadine, truvada, valaciclovir, ciramidine, zanamivir, zidovudine, MMR vaccine, DTaP vaccine, hepatitis vaccines, Hib vaccine, IHPV vaccine, influenza vaccine, polio vaccine, rotavirus vaccine, shingles vaccine, Tdap vaccine, tetanus vaccine, fluconazole, ketoconazole, amphotericin B, and sulfadoxine/pyrimethamine. Additional non-limiting examples include Abacavir, Acyclovir (Aciclovir), Adefovir, Amantadine, Ampligen, Amprenavir (Agenerase), Arbidol, Atazanavir, Atripla, Balavir, Baloxavir marboxil (Xofluza®), Biktarvy Boceprevir (Victrelis®), Cidofovir, Cobicistat (Tybost®), Combivir (fixed dose drug), Daclatasvir (Daklinza®), Darunavir, Delavirdine, Descovy, Didanosine, Docosanol, Dolutegravir, Doravirine (Pifeltro®), Ecoliever, Edoxudine, Efavirenz, Elvitegravir, Emtricitabine, Enfuvirtide, Entecavir, Etravirine (Intelence®), Famciclovir, Fomivirsen, Fosamprenavir, Foscarnet, Fosfonet, Fusion inhibitor, Ganciclovir (Cytovene®), Ibacitabine, Ibalizumab (Trogarzo®), Idoxuridine, Imiquimod, Imunovir, Indinavir, Inosine, Integrase inhibitor, Interferon type I, Interferon type II, Interferon type III, Interferon, Lamivudine, Letermovir (Prevymis®), Lopinavir, Loviride, Maraviroc, Methisazone, Moroxydine, Nelfinavir, Nevirapine, Nexavir®, Nitazoxanide, Norvir, Nucleoside analogues, Oseltamivir (Tamiflu®), Peginterferon alfa-2a, Peginterferon alfa-2b, Penciclovir, Peramivir (Rapivab®), Pleconaril, Podophyllotoxin, Protease inhibitor (pharmacology), Pyramidine, Raltegravir, Remdesivir, Reverse transcriptase inhibitor, Ribavirin, Rilpivirine (Edurant®), Rimantadine, Ritonavir, Saquinavir, Simeprevir (Olysio®), Sofosbuvir, Stavudine, Synergistic enhancer (antiretroviral), Telaprevir, Telbivudine (Tyzeka®), Tenofovir alafenamide, Tenofovir disoproxil, Tenofovir, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza®), and Zidovudine.

Non-limiting examples of treatments for COVID 19 include but are not limited to an anti-viral agent, antibody therapies, an anti-inflammatory drug, an anti-malarial drug, bronchodilators, oxygen supplementation therapy, or ventilation.

In some embodiments of any of the aspects, the therapeutic agent is administered in an amount needed to alleviate or prevent at least one or more symptom of a viral infection. The term "effective amount" as used herein refers to the amount of a therapeutic agent needed to alleviate or prevent at least one or more symptom of an infection, disease or disorder, and relates to a sufficient amount of pharmacological composition to provide the desired effect, e.g., reduce the level of pathogenic virus, reduce pathology, or any symptom associated with or caused by the virus (e.g., SARS-CoV2). An effective amount as used herein would also include an amount sufficient to delay the development of a symptom of the disease, alter the course of a symptom disease (for example, but not limited to, slow the progression of a symptom of the disease), or reverse a symptom of the disease. Thus, it is not possible to specify the exact "effective amount." However, for any given case, an appropriate "effective amount" can be determined by one of ordinary skill in the art using only routine experimentation.

Some Selected Definitions

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

As used herein, "nucleic acid" refers to DNA, RNA, single-stranded, double-stranded, or more highly aggregated hybridization motifs, and any chemical modifications thereof.

As used herein, "viral nucleic acid" refers to nucleic acids that are derived from a virus or fragment thereof.

The term "nucleic acid sequence" or "oligonucleotide" or "polynucleotide" are used interchangeably herein and refers to at least two nucleotides covalently linked together. The term "nucleic acid sequence" is also used inter-changeably herein with "gene", "cDNA", and "mRNA". As will be appreciated by those in the art, the depiction of a single nucleic acid sequence also defines the sequence of the complementary nucleic acid sequence. Thus, a nucleic acid sequence also encompasses the complementary strand of a depicted single strand. Unless otherwise indicated, a particular nucleic acid sequence also implicitly encompasses conservatively modified variants thereof (e.g., degenerate codon substitutions) and complementary sequences, as well as the sequence explicitly indicated. As will also be appreciated by those in the art, a single nucleic acid sequence provides a probe that can hybridize to the target sequence under stringent hybridization conditions. Thus, a nucleic acid sequence also encompasses a probe that hybridizes under stringent hybridization conditions. The term "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. Nucleic acid sequences can be single stranded or double stranded, or can contain portions of both double stranded and single stranded sequence. The nucleic acid sequence can be DNA, both genomic and cDNA, RNA, or a hybrid, where the nucleic acid sequence can contain combinations of deoxyribo- and ribo-nucleotides, and combinations of bases including uracil, adenine, thymine, cytosine, guanine, inosine, xanthine hypoxanthine, isocytosine and isoguanine. Nucleic acid sequences can be obtained by chemical synthesis methods or by recombinant methods. A nucleic acid sequence will generally contain phosphodiester bonds, although nucleic acid analogs can be included that can have at least one different linkage, e.g., phosphoramidate, phosphorothioate, phosphorodithioate, or O-methylphosphoroamidite linkages and peptide nucleic acid backbones and linkages in the nucleic acid sequence. Other analog nucleic acids include those with positive backbones; non-ionic backbones, and non-ribose backbones, including those described in U.S. Pat. Nos. 5,235,033 and 5,034,506, which are incorporated by reference. Nucleic acid sequences containing one or more non-naturally occurring or modified nucleotides are also included within one definition of nucleic acid sequences. The modified nucleotide analog can be located for example at the 5'-end and/or the 3-end of the nucleic acid sequence. Representative examples of nucleotide analogs can be selected from sugar- or backbone-modified ribonucleotides. It should be noted, however, that also nucleobase-modified ribonucleotides, i.e. ribonucleotides, containing a non naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e. g. 7 deaza-adenosine; O— and N— alkylated nucleotides, e.g. N6-methyl adenosine are suitable. The 2' OH— group can be replaced by a group selected from H. OR, R. halo, SH, SR, NH2, NHR, NR2 or CN, wherein R is C—C6 alkyl, alkenyl or alkynyl and halo is F. Cl, Br or I. Modifications of the ribose-phosphate backbone can be done for a variety of reasons, e.g., to increase the stability and half-life of such molecules in physiological environments or as probes on a solid support. Mixtures of naturally occurring nucleic acids and analogs can be used; alternatively, mixtures of different nucleic acid analogs, and mixtures of naturally occurring nucleic acids and analogs can be used. Nucleic acid sequences include but are not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc.

As used herein, the term "oligonucleotide" is intended to include, but is not limited to, a single-stranded DNA or RNA molecule, typically prepared by synthetic means. Nucleotides of the present invention will typically be the naturally-occurring nucleotides such as nucleotides derived from adenosine, guanosine, uridine, cytidine and thymidine. When oligonucleotides are referred to as "double-stranded," it is understood by those of skill in the art that a pair of oligonucleotides exists in a hydrogen-bonded, helical array typically associated with, for example, DNA. In addition to the 100% complementary form of double-stranded oligonucleotides, the term "double-stranded" as used herein is also meant to include those form which include such structural features as bulges and loops (see Stryer, Biochemistry, Third Ed. (1988), incorporated herein by reference in its entirety for all purposes).

As used herein, the term "RNA" refers to ribonucleic acid, which as typically transcribed in nature comprises the purine nucleobases adenine and guanine and the pyrimidine nucleobases cytosine and uracil. RNA oligonucleotides described herein can include modified nucleobases or modifications to the ribose-phosphate backbone that, for example, enhance stability or resistance to degradation. Examples of such modifications are discussed herein below or known in the art. In one embodiment of any of the aspects described herein, the modification is not removal of the 2' hydroxyl that distinguishes RNA from deoxyribonucleic acid.

As used herein, the terms "protein" and "polypeptide" are used interchangeably to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

The term "expression" as used herein refers to the biosynthesis of a gene or nucleic acid sequence, preferably to the transcription and/or translation of a nucleotide sequence, for example an endogenous gene or a heterologous gene, in a cell.

As used herein, "contacting" refers to any suitable means for delivering, or exposing, an agent to at least one component as described herein (e.g., sample, target nucleic acid, target RNA, cDNA, amplification product, etc.). In some embodiments, contacting comprises physical human activity, e.g., an injection; an act of dispensing, mixing, and/or decanting; and/or manipulation of a delivery device or machine.

The methods and uses of the compositions, assays, and kits, provided herein can involve in vivo, ex vivo, or in vitro use. The term "in vivo" refers to assays or processes that occur in or within an organism, such as a multicellular animal. The term "ex vivo" refers to methods and uses that are performed using a living cell with an intact membrane that is outside of the body of a multicellular animal or plant, e.g., explants, cultured cells, including primary cells and cell lines, transformed cell lines, and extracted tissue or cells, including blood cells, among others. The term "in vitro" refers to assays and methods that do not require the presence of a cell with an intact membrane, such as cellular extracts, and can refer to the introducing any of the systems described herein into a non-cellular system, such as a media not comprising cells or cellular systems, such as cellular extracts.

As used herein, the term "hybridizing", "hybridize", "hybridization", "annealing", or "anneal" are used interchangeably in reference to the pairing of complementary nucleic acids using any process by which a strand of nucleic acid joins with a complementary strand through base pairing to form a hybridization complex. In other words, the term "hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex."

In some embodiments of the various aspects described herein, the step of hybridizing the probe with the amplified product comprises heating and/or cooling. For example, a reaction comprising the amplified product and the probe can be heated and then cooled to promote hybridization.

It is noted that the hybridization step can be carried out in the same reaction vessel used for preparing the amplified product. Alternatively, the amplified product can be isolated or purified from the amplification reaction prior to the hybridization step. In other words, the amplification step and the hybridization steps are in different reaction vessels.

"Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the Tm for the specific sequence at a defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, Molecular Cloning A Laboratory Manual, 2nd Ed. Cold Spring Harbor Press (1989) and Anderson Nucleic Acid Hybridization, 1st Ed., BIOS Scientific Publishers Limited (1999). "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third non-target entity. A reagent specific for a given target is one that exhibits specific binding for that target under the conditions of the assay being utilized.

As used herein, a "subject" means a human or animal. Usually the animal is a vertebrate such as a primate, rodent, domestic animal or game animal. Primates include, for example, chimpanzees, cynomolgus monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments of any of the aspects, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of disease e.g., coronavirus infection model. A subject can be male or female.

A subject can be one who has been previously diagnosed with or identified as suffering from or having a disease or disorder in need of treatment (e.g., COVID 19) or one or more complications related to such a disease or disorder, and optionally, have already undergone treatment for the disease or disorder or the one or more complications related to the disease or disorder. A subject can be resistant to at least one treatment for the disease or disorder. Alternatively, a subject can also be one who has not been previously diagnosed as having such disease or disorder or related complications. For example, a subject can be one who exhibits one or more risk factors for the disease or disorder or one or more complications related to the disease or disorder or a subject who does not exhibit risk factors.

As used herein, the terms "treat," "treatment," or "treating," refer to therapeutic treatments, wherein the object is to reverse, alleviate, inhibit, slow down or stop the progression or severity of a condition associated with a viral infection, e.g., SARS-Cov-2 infection. The term "treating" includes reducing or alleviating at least one adverse effect or symptom of a viral infection. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment). Symptoms and clinical markers of a viral infection are further described herein below.

As used herein, the term "prevent" or "preventing" refers to the prevention of at least one symptom associated with a viral infection, or complete prevention of a viral infection, or the lessening of the severity of a viral infection (e.g., preventing the progression of a viral infection) in a subject, and/or delaying one or more symptoms of a viral infection, and/or delaying the onset of a viral infection and/or symptoms following exposure to a virus.

As used herein, the term "administering" refers to the placement of a therapeutic agent, or composition or pharmaceutical composition thereof as disclosed herein into a subject by a method or route which results in at least partial delivery of the agent to the subject. Compositions and pharmaceutical compositions comprising therapeutics (e.g., a compound or agent that treats SARS-CoV 2 infection or COVID 19) as disclosed herein can be administered by any appropriate route which results in an effective treatment in the subject.

The term "decrease", "reduced", "reduction", or "inhibit" are all used herein to mean a decrease by a statistically significant amount. In some embodiments of any of the aspects, "decrease", "reduced", "reduction", or "inhibit" typically means a decrease by at least 10% as compared to an appropriate control (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference value, appropriate control, or reference level.

The terms "increased," "increase," "increases," or "enhance" or "activate" are all used herein to generally mean an increase of a property, level, or other parameter by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference value, appropriate control, or reference level.

As used herein, a "reference value" refers to a parameter, number, value, or range of values that is determined or expected for a given sample (e.g., a positive or negative sample used as a control in the assay provided herein).

As used herein, an "appropriate control" refers to an untreated, otherwise identical sample or population (e.g., a sample from a subject who does not have a viral infection or a sample from a subject that is known to have a viral infection).

As used herein, a "reference level" refers to a normal, otherwise unaffected cell population or tissue (e.g., a biological sample obtained from a healthy subject, or a biological sample obtained from the subject at a prior time point, e.g., a biological sample obtained from a patient prior to being diagnosed with a viral infection or prior to receiving a given treatment, or a biological sample that has not been contacted with a therapeutic agent disclosed herein).

The term "statistically significant" or "significantly" refers to statistical significance and generally means a two standard deviation (2SD) or greater difference.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean±1%.

All patents and other publications identified are expressly incorporated herein by reference for the purpose of describing and disclosing, for example, the methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents are based on the information available to the applicants and do not constitute any admission as to the correctness of the dates or contents of these documents.

It should be understood that this disclosure is not limited to the particular methodology, protocols, and reagents, etc., provided herein and as such may vary. The terminology used herein is for the purpose of describing particular embodiments only, and is not intended to limit the scope of the present disclosure, which is defined solely by the claims. The invention is further illustrated by the following example, which should not be construed as further limiting.

Some embodiments of the technology described herein can be defined according to any of the following numbered paragraphs:

1) A composition for loop-mediated isothermal amplification (LAMP) of a SARS-coronavirus-2 (COVID-19) nucleic acid, comprising:
    a first nucleic acid strand (first primer) comprising a nucleotide sequence CGGTGGACAAATTGTCAC (SEQ ID NO: 1);
    a second nucleic acid strand (second primer) comprising a nucleotide sequence of CTTCTCTGGATTTAACACACTT (SEQ ID NO: 2)
    a third nucleic acid strand (third primer) comprising a nucleotide sequence of TCAGCACACAAAGCCAAAAATTTATCTGTGCAAAGGAAATTAAGGAG (SEQ ID NO: 3) or TCAGCACACAAAGCCAAAAATTTATTTTTCTGTGCAAAGGAAATTAAGGAG (SEQ ID NO: 4);
    a fourth nucleic acid strand (fourth primer) comprising a nucleotide sequence of TATTGGTGGAGCTAAACTTAAAGCCCTGTACAATCCCTTTGAGTG (SEQ ID NO: 5) or TATTGGTGGAGCTAAACTTAAAGCCTTTTCTGTACAATCCCTTTGAGTG (SEQ ID NO: 6);
    a fifth nucleic acid strand (fifth primer) comprising a nucleotide sequence of TTACAAGCTTAAAGAATGTCTGAACACT (SEQ ID NO: 7); and
    a sixth nucleic acid strand (sixth primer) comprising a nucleotide sequence of TTGAATTTAGGTGAAACATTTGTCACG (SEQ ID NO: 8).
2) The composition of paragraph 1, further comprising one or more reagents or buffers for loop-mediated isothermal amplification of a nucleic acid.
3) The composition of any one of paragraphs 1-2, further comprising a colorimetric reagent.
4) The composition of any one of paragraphs 1-3, further comprising dNTPs.
5) The composition of any one of claims 1-4, further comprising a polymerase enzyme.
6) The composition of any one of paragraphs 1-5, further comprising a reverse transcriptase.
7) The composition of any one of paragraphs 1-6, further comprising a buffer solution for loop-mediated isothermal amplification of a nucleic acid.
8) The composition of any one of paragraphs 1-7, further comprising a detergent.
9) The composition of any one of paragraphs 1-8, further comprising a sample suspected of comprising SARS-coronavirus-2.
10) A kit for detecting SARS-coronavirus-2, the kit comprising the composition of any one of paragraphs 1-8.
11) The kit of paragraph 10, further comprising a nucleic acid strand comprising a nucleotide sequence substantially complementary to SEQ ID NO: 1, SEQ ID NO: 2, SEQ ID NO: 3, SEQ ID NO: 4, SEQ ID NO: 5, SEQ ID NO: 6, SEQ ID NO: 7, and/or SEQ ID NO: 8.
12) The kit of paragraph 10 or 11, further comprising reagents and packaging materials thereof.
13) An assay for detecting a SARS-coronavirus-2 nucleic acid in a sample, the method comprising:
    (a) contacting a sample with a composition of any one of paragraphs 1-8 to produce a reaction mixture, wherein the reaction mixture comprises one or more reagents or buffers for loop-mediated isothermal amplification of a nucleic acid; and
    (b) heating the reaction mixture of step (a) to a temperature of about 65° C. for a period of time,
    wherein a color change in the reaction mixture indicates the presence of a SARS-coronavirus-2 in the sample.
14) The assay of paragraph 13, further comprising obtaining the biological sample from a subject having or suspected of having a SARS-coronavirus-2 infection.
15) The assay of paragraph 13 or 14, further comprising cooling the reaction mixture from step (b) to room temperature.
16) The assay of any one of paragraphs 13-15, further comprising a lysis step prior to step (a).
17) The assay of any one of paragraphs 13-16, further comprising a step of nucleic acid isolation or purification prior to step (a).
18) The assay of any one of paragraphs 13-17, further comprising a step of isolating or purifying the SARS-coronavirus-2 nucleic acid sample, where said isolating or purifying comprises contacting the sample with silica particles.
19) The assay of any one of paragraphs 13-18, wherein the reaction mixture further comprises a denaturing agent.
20) The assay of any one of paragraphs 13-19, wherein the reaction mixture further comprises guanidinium thiocyanate or guanidinium isothiocyanate.

EXAMPLES

Example 1—Warmstart™ Lamp Kit (DNA & RNA) Protocol (E1700)

Reaction Setup: For simplicity in setting up reactions, we recommend making stocks of the LAMP primers at a usable concentration. For example, we suggest a 10× Primer Mix containing all 6 LAMP primers.

TABLE 4

| 10X LAMP Primer Mix | | |
| --- | --- | --- |
| PRIMER | 10X CONCENTRATION (STOCK) | 1X CONCENTRATION (FINAL) |
| FIP | 16 μM | 1.6 μM |
| BIP | 16 μM | 1.6 μM |
| F3 | 2 μM | 0.2 μM |
| B3 | 2 μM | 0.2 μM |
| LOOP F | 4 μM | 0.4 μM |
| LOOP B | 4 μM | 0.4 μM |

Prepare primer stocks in nuclease-free water and store at −20° C. for up to 2 years.

1. Thaw all components to be used at room temperature and place on ice. Vortex briefly to mix and centrifuge to collect material.
2. Prepare reaction mix as described below. Volumes are listed for a 25 μl LAMP reaction, but other volumes (10, 20, 50 μl etc.) are all effective; if desired, adjust volumes accordingly. A 1 μl target DNA volume is shown; if higher sample volumes are needed, adjust volume of H2O. For non-template reactions add equivalent volume of H2O or sample storage buffer.

TABLE 5

Target Detection Reaction Mix

|  | DNA TARGET DETECTION | RNA TARGET DETECTION | NO-TEMPLATE CONTROL (NTC) |
|---|---|---|---|
| WarmStart LAMP 2X Master Mix | 12.5 µl | 12.5 µl | 12.5 µl |
| Fluorescent dye (50X) | 0.5 µl | 0.5 µl | 0.5 µl |
| LAMP Primer Mix (10X) | 2.5 µl | 2.5 µl | 2.5 µl |
| Target DNA | 1 µl | — | — |
| Target RNA | — | 1 µl | — |
| dH$_2$O | 8.5 µl | 8.5 µl | 9.5 µl |
| Total Volume | 25 µl | 25 µl | 25 µl |

3. Vortex reaction mix and centrifuge to collect material.
4. Pipet 24 µl per reaction into desired reaction vessels and add sample. Mix by vortexing and centrifuge to collect, or by pipetting if using a plate or other vessel.
5. Seal reaction vessel.
6. Incubate at 65° C. for 30 minutes. Time can be extended as necessary for very low copy targets, challenging sample types, or reactions known to produce slower amplification times.
7. If reaction products will be manipulated or analyzed after LAMP is complete, Bst 2.0 and RTx can be inactivated by heating at >80° C. for 5 minutes.

Resources

Product Categories:

Isothermal Amplification & Strand Displacement Products

Available on the world-wide web at https <www.neb.com/products/pcr-qpcr-and-amplification-technologies/isothermal-amplification-and-strand-displacement>

Applications:

Isothermal Amplification

Available on the world-wide web at https <www.neb.com/applications/dna-amplification-pcr-and-qpcr/isothermal-amplification>

Related Products:

WarmStart® LAMP Kit (DNA & RNA)

Available on the world-wide web at https <www.neb.com/products/e1700-warmstart-lamp-kit-dna-rna>

Available on the world-wide web at https <www.neb.com/protocols/2016/08/15/warmstart-lamp-kit-dna-rna-protocol-e1700>

Example 2—Warmstart™ Colorimetric Lamp 2× Master Mix Typical Lamp Protocol (M1800)

Reaction Setup: For simplicity in setting up reactions, we recommend making stocks of the LAMP primers at a usable concentration. For example, we suggest a 10× Primer Mix containing all 6 LAMP primers (Table 4).

Make primer stock in molecular biology grade H2O rather than TE or other buffer in order to avoid carryover of additional buffer to the LAMP reaction. Prepare primer stocks in nuclease free water and store at −20° C. for up to 2 years. 1. Thaw all components to be used at room temperature and place on ice. Salt may appear in the bottom of the tube so vortex briefly or invert tubes several times to mix thoroughly. Centrifuge to collect material and place on ice. 2. Prepare reaction mix as described below using Colorimetric LAMP Master Mix, LAMP primers and nuclease free water. Volumes listed per 25 µl LAMP reaction, but other volumes (10, 20, 50 µl etc.) are all effective if desired, just adjust volumes accordingly. Sample is assumed here to be 1 µl, but for higher sample volumes add as needed and reduce volume of H$_2$O to compensate. For non-template reactions add equivalent volume of H2O or sample storage buffer.

TABLE 6

WarmStart Colorimetric LAMP 2X Reaction Mix

| DNA TARGET RNA | TARGET DETECTION | NO-TEMPLATE CONTROL (NTC) |
|---|---|---|
| Master Mix (Table 4) | 12.5 µl | 12.5 µl |
| LAMP Primer Mix (10X) | 2.5 µl | 2.5 µl |
| Target DNA 1 µl | — | — |
| Target RNA 1 µl | — | — |
| dH$_2$O | 9 µl | 10 µl |
| Total Volume | 25 µl | 25 µl |

Vortex reaction mix and centrifuge to collect material.

Pipet 24 µl per reaction into desired reaction vessels and add 1 µl of sample.

Mix by vortexing or by pipetting if using a plate or similar vessel, centrifuge to collect if necessary. Check that reaction solutions have a bright pink color, which indicates initial high pH required for successful pH-LAMP reaction.

Seal reaction vessels.

Incubate at 65° C. for 30 minutes.

Remove tubes or vessels from incubation and examine by eye. Positive reactions will have turned yellow while negative controls should remain pink. If color change is not robust, e.g. an orange color is visible, return reactions to 65° C. for an additional 10 minutes.

Reactions can be examined earlier if desired, and high copy or input reactions can exhibit full color change in as little as 10-15 minutes. Color will be visible directly on removal from incubation temperature, but can be intensified by allowing reaction to cool to room temperature.

The result can be photographed or scanned to record the colorimetric results, or simply kept at room temperature in the reaction vessel.

Links to this resource:

Product Categories: Isothermal Amplification & Strand Displacement Products

Applications: Isothermal Amplification

Related Products: WarmStart® Colorimetric LAMP 2×Master Mix (DNA & RNA)

<www.neb.com/protocols/2016/08/15/warmstart-colorimetric-lamp-2x-master-mix-typical-lamp-protocol-m1800>.

Example 3—Lamp Primer Sequences

Compositions and sequences for use in the detection of SARS-Cov-2 in a sample (e.g., using a LAMP protocol) are provided in the following table.

TABLE 7

Oligo sequences

| Name | Sequence | Assay Concentration (µM) |
|---|---|---|
| As1_F3 | CGGTGGACAAATTGTCAC (SEQ ID NO: 1) | 0.2 |
| As1_B3 | CTTCTCTGGATTTAACACACTT (SEQ ID NO: 2) | 0.2 |
| As1_FIP | TCAGCACACAAAGCCAAAAATTTA TCTGTGCAAAGGAAATTAAGGAG (SEQ ID NO: 3) | 1.6 |
| As1_BIP | TATTGGTGGAGCTAAACTTAAAGC CCTGTACAATCCCTTTGAGTG (SEQ ID NO: 5) | 1.6 |
| As1_LF | TTACAAGCTTAAAGAATGTCTGAA CACT (SEQ ID NO: 7) | 0.4 |
| As1_LB | TTGAATTTAGGTGAAACATTTGTCA CG (SEQ ID NO: 8) | 0.4 |
| As1e_FIP | TCAGCACACAAAGCCAAAAATTTATT TTTCTGTGCAAAGGAAATTAAGGAG (SEQ ID NO: 4) | 1.6 |
| As1e_BIP | TATTGGTGGAGCTAAACTTAAAGC CTTTTCTGTACAATCCCTTTGAGTG (SEQ ID NO: 6) | 1.6 |

Example 4—Reaction Mixtures and Protocols

Several reaction mixtures and LAMP detection protocols were tested and are set out in FIGS. 1-13B. A preparation protocol and sample protocol for glass milk and column-based assay are provided below.

Glass Milk—Alternative to Silica Columns

Preparation Protocol:

1. Start with Silica Dioxide 325 Mesh (Spectrum Chemicals—S1108-500GM)
2. Wash in 10% HCL for 4-12 hours
3. Pellet (5,000×g for 5 minutes)
4. Pour off supernatant, replace with 2 volumes MilliQ water
5. Repeat pellet/wash 4-5 times
6. Wash twice with 10 mM Tris-HCL (pH 7.5-8) and 0.2 mM EDTA
7. Check pH, ensure ~7-8
8. Resuspend glass pellet in 1 volume 10 mM Tris and 0.2 mM EDTA (to create a 50% slurry)
9. Autoclave to destroy any contaminating nucleic acids Sample Protocol:

1. Lyse samples and prepare for binding as described in a column-based kit
2. Instead of adding to column, simply add 2-5 ul of glass milk, mix and allow to bind for one minute
3. Short spin to pellet, remove supernatant
4. Wash with first wash buffer (add buffer, pipette or vortex to mix)
5. Repeat spins and washes as described for the kit (e.g., one more ethanol wash after initial guanidinium-based washes)
6. Remove last wash after spinning, air dry briefly, add water, mix, spin
7. Supernatant contains eluted nucleic acid ready for downstream applications.

Example 5: Rt-Lamp Assays for SARS-CoV-2 Detection

Introduction/Background

The current SARS-CoV-2 pandemic has had and will continue to have an enormous impact on society worldwide, threatening the lives and livelihoods of many. As the disease spreads, the need for rapid point-of-care diagnostic tools has become immense. Many efforts are currently underway to develop such an assay that can be easily used in a variety of settings.[1] Such an assay would require no specialized equipment and would have a rapid and easy to read result. To that end, we have developed a novel assay using the reverse-transcription loop-mediated isothermal amplification (RT-LAMP) technique as well as a simple and rapid sample preparation protocol that yields results in under an hour with great sensitivity. Furthermore, our sample preparation protocol utilizes reagents that are simple to prepare in great abundance.

LAMP is a method of isothermal DNA replication that utilizes, in an accelerated format, six DNA oligos that hybridize with 8 different regions of a target molecule.[2] Utilizing a strand displacing polymerase and loops formed during this reaction, an incredibly fast amplification reaction can occur upon proper oligo binding to the desired target. Such reactions are capable of generating microgram quantities of DNA in a very short period of time at a single reaction temperature. Furthermore, although the included polymerase has reverse transcriptase activity, a reverse transcriptase can be included to optimize sensitivity within the reaction when detecting an RNA target (RT-LAMP), such as the SARS-CoV-2 genomic RNA. LAMP assays have a variety of readouts due to the enormous quantity of DNA generated, included fluorescence using an intercalating DNA dye, turbidity, or, by a drop in the pH if the reaction is minimally buffered.[1, 3, 4] This change in pH, sufficient to cause a pH indicator dye to visibly change color, is the most enticing method for a point-of-care LAMP-based diagnostic.

We decided to design and test our own RT-LAMP assay utilizing the LAMP reaction reagents from New England Biolabs. For each of 11 assays tested we utilized PrimerExplorer V5 (https://primerexplorer.jp/e/) to design all primers with the exception of the loop primers for Assay 1, for which PrimerExplorer could find none, which were designed by hand. As we prepared to test these assays, we learned of several other assays designed by researchers at New England Biolabs, and so we also tested their two most sensitive assays, Gene N-A and Orf1a-C, in order to compare these with our own assays.[1]

Figure 14:
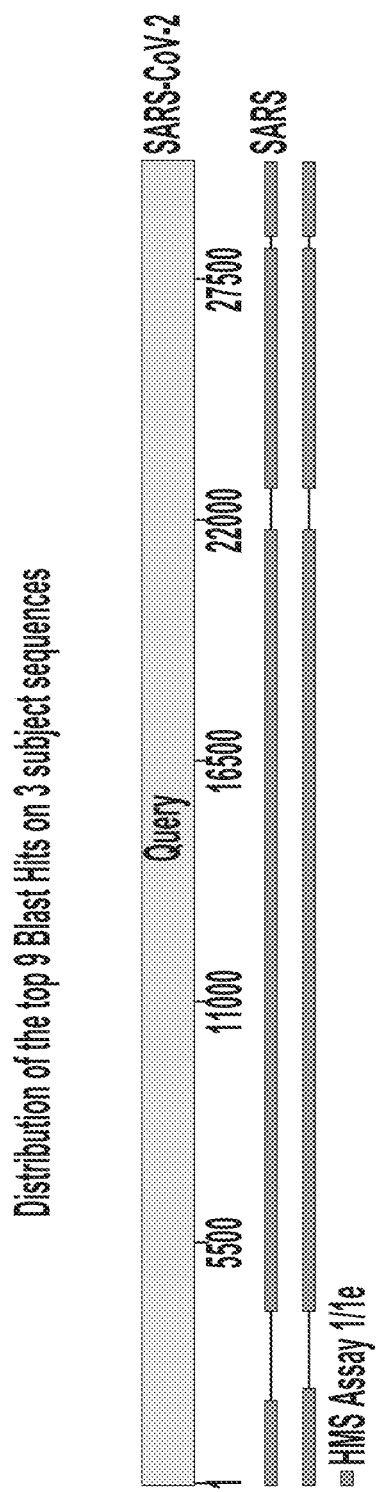
FIG. 14 demonstrates alignment of SARS-CoV-2 to related coronaviruses. An alignment (blastn, megablast) of SARS, Bat SARS-like coronavirus isolate Rs4084, and the sequence detected by HMS Assay 1/1e.

One of the assays, HMS Assay 1, performed particularly well compared to the others (data not shown for others) and we then modified the forward inner primer (FIP) and backward inner primer (BIP) of this assay to include "TTTT" linker between the F1c and F2 regions to create HMS Assay 1e, as this has been reported to further improve the reaction (for HMS Assay 1 and HMS Assay 1e oligo sequences, see Table 1 and Table 7).[5] HMS Assay 1/1e is designed within the ORFlab of SARS-CoV-2 in a region that is not highly conserved with either SARS or Bat SARS-like coronavirus isolate Rs4084, two closely related coronaviruses (FIG. 14). As we demonstrate, HMS Assay 1 and HMS Assay 1e outperform NEB Gene N-A and NEB Orf1a-C in terms of sensitivity and speed.

In addition to developing a robust RT-LAMP primer set, we also sought to optimize downstream sample preparation in a way that would increase sensitivity to the greatest extent possible. In order to do this, we explored the tolerance of the RT-LAMP reaction to detergents and chaotropic salts that might aid in lysis and purification of viral genomes. As we demonstrate, these tolerance tests have allowed us to create a simple and rapid process by which viral RNA can be concentrated from as little as 0.5 ml of collection media such that, when used with the HMS Assay 1e, 10 genomes per microliter can be detected. Unlike purification schemes used for the current FDA approved qRT-PCR-based test, this purification does not require a commercial kit or a centrifuge. In addition, the RNA in the samples is kept in either a high ethanol solution or in the presence of enough guanidinium thiocyanate (GuSCN) to inhibit RNAse activity throughout, ensuring the samples will remain stable while testing. Furthermore, we can easily prepare enough of the silica particles used for millions of purifications in an afternoon.

Results

Sensitivity of HMS and NEB RT-LAMP Assays

We first tested HMS Assay 1, HMS Assay 1e, NEB Gene N-A, and NEB Orf1a-C using the NEB's WarmStart LAMP Kit (NEB E1700) with a real-time fluorescence-based readout (FIG. 15A-15D). In this reaction scheme, each cycle represents 30 seconds at 65 C. Ideally, a positive result will be read after 30 minutes, or the 60$^{th}$ cycle, a time point used by Zhang et al[1]. We used positive control RNAs from Twist Bioscience (Sku 102019). We ran 10 μl reactions in triplicate, including 0, 100, 200, or 300 RNA genomes per reaction. As can be seen, all four assays are capable of detecting genomes at low levels, although in this setup NEB Gene N-A demonstrated lower sensitivity and later amplification than the rest.

In order to further assess sensitivity, we ran repeated reactions using the same fluorescence-based readout with HMS Assay 1, HMS Assay 1e, and NEB Orf1a-C (FIG. 16A-16C). For each, we ran 48 10 μl reactions with 200 genomes each and 48 10 μl reactions with no genomes added. As can be seen, both HMS assay 1 and HMS assay 1e performed very well, showing high amplification in 45 and 47 out of 48 reactions with 200 genomes, respectively. Furthermore, none of the reactions without genomes exhibited any amplification by 60 minutes. NEB Orf1a-C did not perform as well, as the time to amplification in the 200 genome reactions was highly variable with many not amplifying until just before or after the 30-minute point. Furthermore, two reactions without genomes exhibited amplification, but we cannot rule out the possibility that these reactions, as sensitive as they are, were contaminated. These data suggest that HMS Assay 1 and HMS Assay 1e are the more robust assays.

Detergent Tolerance: In order to potentially improve the sensitivity of the RT-LAMP reaction when using patient samples, we hypothesized that an increase in detergent within the reaction might help to more readily lyse virions, thus making their genomes accessible for detection and amplification. Thus, using HMS Assay 1 and the same 10 μl fluorescent reactions as described above, we ran reactions with 500 genomes and differing amounts of added Tween20 or TritonX100 (FIG. 17A-17B). As can be seen, the reaction is quite tolerant of added detergents, and robust amplification can be seen up to at least 1.5% Tween20 and 1% TritonX100. Amplification can still be detected for both detergents up to 3%, but the reactions appear to plateau at a lower level of fluorescence as detergent levels increase.

Figure 18B:
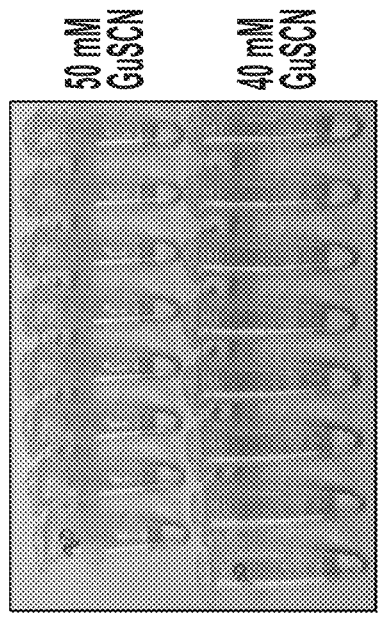
FIG. 18A-18B shows the assessment of RT-LAMP GuSCN tolerance. 25 µl RT-LAMP reactions were run with a colorimetric readout. All reactions used the HMS Assay 1e primer set and 27 mM-160 mM GuSCN (1:25-1:150 dilution of sample lysis buffer). Each reaction was incubated at 65 C for 30 minutes.
Figure 18A:
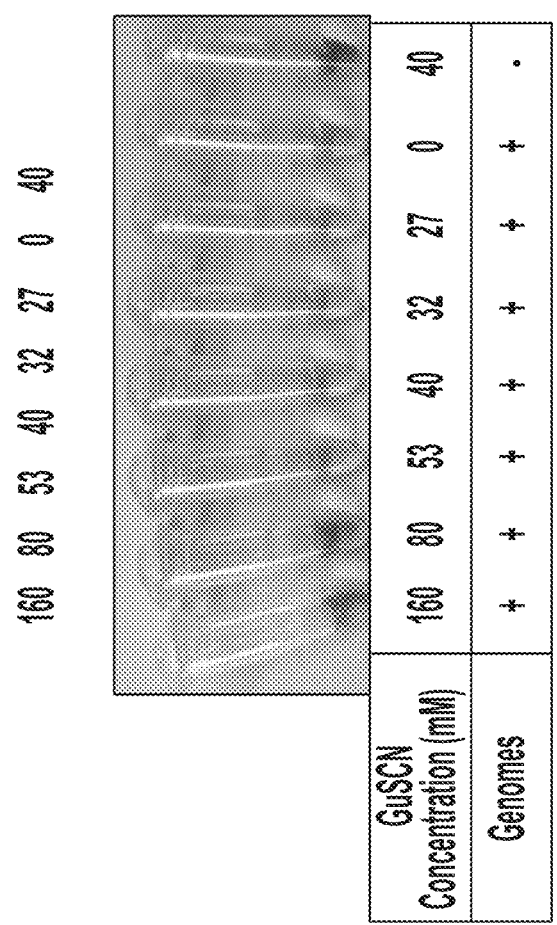

Guanidinium Thiocyanate Tolerance: Most RNA purification schemes utilize guanidinium thiocyanate (GuSCN).[6] This chaotropic salt is a powerful protein denaturant that can aid in lysis and RNAse inactivation. We wanted to test the tolerance of the RT-LAMP reactions to this chemical in order to optimize a rapid purification protocol that might not remove all GuSCN traces. In order to test this, we created a sample lysis buffer containing 4 M GuSCN and 2% TritonX100. We then added varying amounts of this buffer into HMS Assay 1e 25 μl colorimetric RT-LAMP reactions (NEB M1800) with 500 genomes, such that the final GuSCN concentration would range from 160 mM to 27 mM (i.e. a final dilution of 1:25 to 1:150 in the final reaction, FIG. 18A). All colorimetric reactions were run for 30 minutes at 65 C. As can be seen, the reaction is visibly positive at GuSCN concentrations at or below 53 mM (1:75 dilution) although the 53 mM reaction is slightly more orange than the rest. To repeat this result, we ran 8 replicates of the same reactions at 50 mM and 40 mM GuSCN (1:80, and 1:100 dilution, respectively, FIG. 18B), and all were robustly positive. This indicates that the colorimetric RT-LAMP reactions are tolerant to GuSCN up to 50 mM.

Guanidinium Effects on Sensitivity and Direct HMS vs NEB Sensitivity Comparison with Colorimetric Assays To confirm that 50 mM GuSCN did not impact the sensitivity of the colorimetric RT-LAMP reactions, we directly compared the sensitivities of HMS Assay 1, HMS Assay 1e, NEB Gene N-A, and NEB Orf1a-C in the colorimetric RT-LAMP reactions. To do this, we ran 25 μl colorimetric RT-LAMP reactions with 0, 100, or 200 genomes, with or without 50 mM GuSCN. These reactions were all run for 30 minutes at 65 C.

Figure 19A:
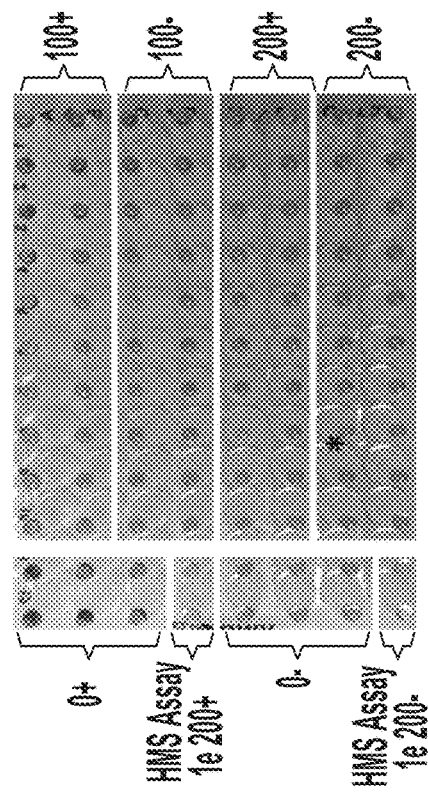
FIG. 19A-19C shows the assessment of GuSCN effects on sensitivity in neb colorimetric RT-LAMP assays. 25 µl RT-LAMP reactions were run with a colorimetric readout. Number of genomes per reaction (0, 100, or 200) noted. Reactions were run with 50 mM GuSCN (+) or without GuSCN (−) as noted. Each reaction was incubated at 65 C for 30 minutes.
Figure 19B:
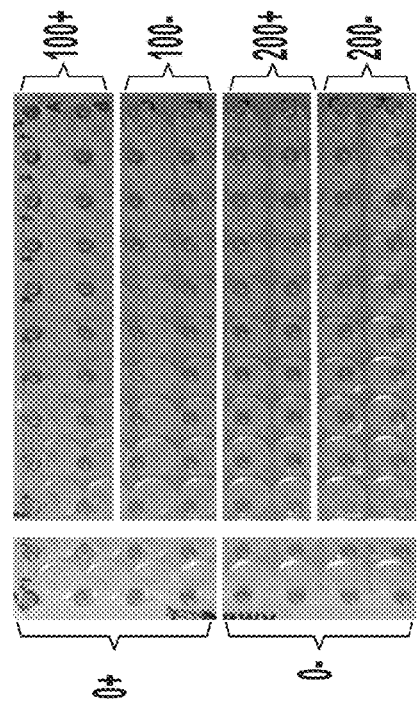

NEB Orf1a-C performed poorly in the presence of 50 mM GuSCN (FIG. 19A), detecting 2/40 with 100 genomes and 5/40 with 200 genomes. This result was surprising, so we ran the experiment again, remaking all reagents including primer mixes and including four reactions of HMS Assay 1e with 200 genomes as a plate control (FIG. 19B).

Figure 19C:
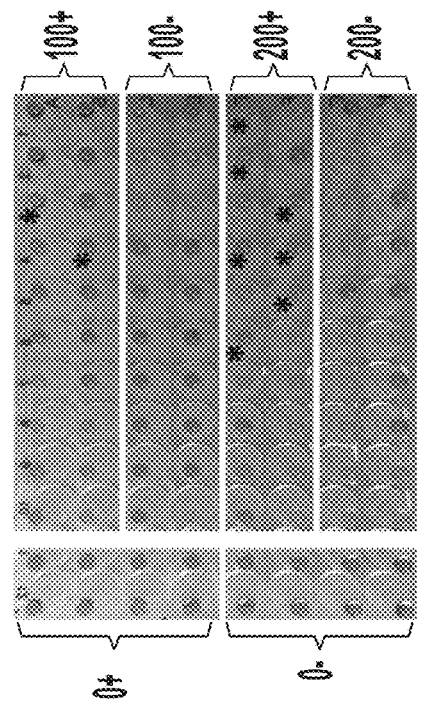
Figure 20B:
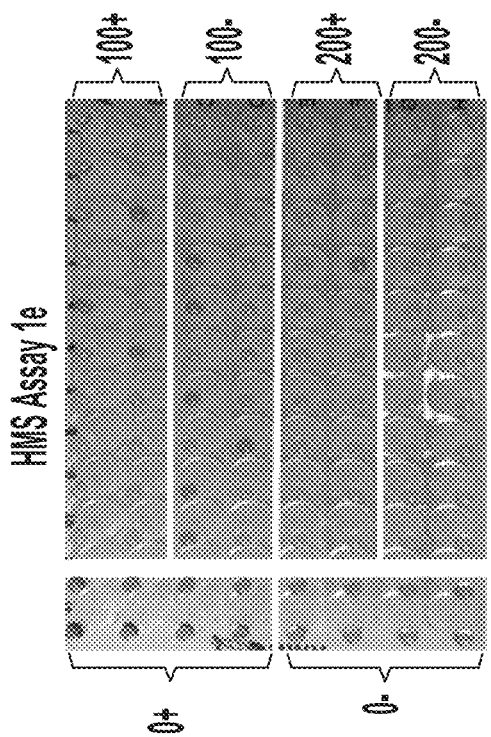
FIG. 20A-20B shows the assessment of GuSCN effects on sensitivity in HMS colorimetric RT-LAMP Assays. 25 µl RT-LAMP reactions were run with a colorimetric readout. Number of genomes per reaction (0, 100, or 200) noted. Reactions were run with 50 mM GuSCN (+) or without GuSCN (−) as noted. Each reaction was incubated at 65 C for 30 minutes.
Figure 20A:
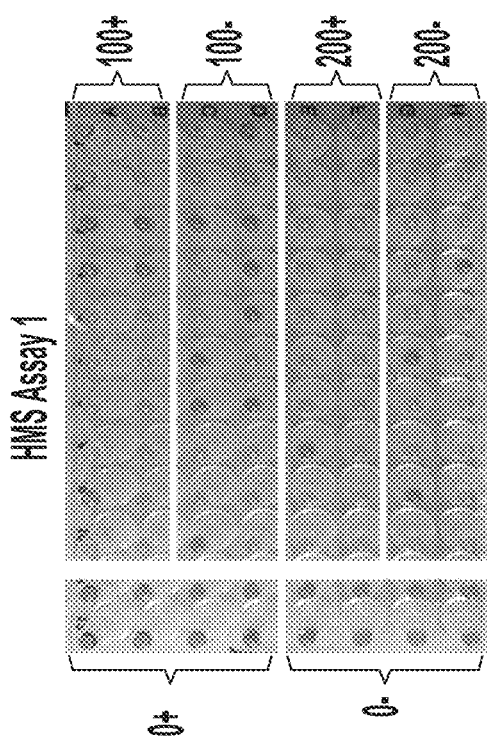

The results were the same, detecting 1/40 with 100 genomes, and 1-2/40 with 200 genomes (one of the 200 genomes reactions turned visibly orange, but not yellow). NEB Gene N-A performed better, detecting 11-13/40 with 100 genomes (depending on whether orange reactions are to be called as positive) and 22-29/40 with 200 genomes (FIG. 19C). HMS Assay 1 and HMS Assay 1e performed much better. At 100 genomes HMS Assay 1 and HMS Assay 1e detected 26/40 and 31/40, respectively (FIG. 20A-20B). At 200 genomes, HMS Assay 1 and HMS Assay 1e detected 36/40 and 39/40, respectively. Furthermore, all positive reactions were completely yellow, leaving no ambiguous orange reactions. Altogether, none of the reactions without genomes resulted in a positive for any of the assays tested (FIG. 19A-19C and FIG. 20A-20B). Finally, there was no difference in sensitivity between reactions that did or did not contain 50 mM GuSCN.

Optimization of a Rapid Purification Scheme

The current sample collection methods used for SARS-CoV-2 testing involve placing swabs in 2-3 ml of collection media.[7] This method presents two challenges for detection. First, very little (no more than 1 μl) can be used in a 25 μl reaction due to the presence of dyes and buffers that would prevent visualization of a pH shift in a positive reaction (data not shown). Furthermore, swabs may contain inhibitors of downstream reactions from saliva, mucous, sputum, etc. This also limits the amount of sample that can be added to a reaction without purification. Thus we set out to design a fast, inexpensive, easy, and robust purification scheme that would allow for the concentration of viral RNAs away from potential inhibitors, thus allowing a far larger portion of collected genomes to be added to the reaction to increase sensitivity. We designed this protocol such that it can be done easily in a clinic without specialized equipment.

Figure 21A:
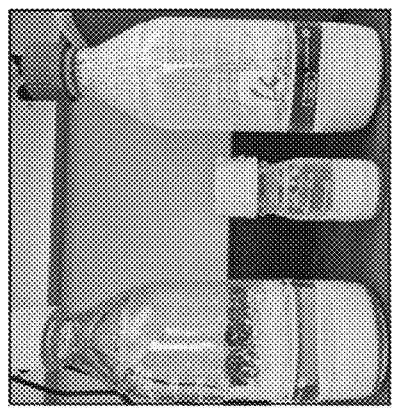
FIG. 21A-21E shows a simple and rapid RNA concentration and purification with glass milk.

To do this, we decided to rely on silica-based purification using a silica particle suspension (i.e. "glass milk") that can be prepared in enormous quantities very quickly and easily (we easily prepared over 700 ml in an afternoon with less than an hour of hands-on time, and use 2 µl per purification, FIG. 21A).[6] We optimized a lysis/binding buffer that contains 2.29 M GuSCN, 0.76% TritonX100, and 62% ethanol that can be combined with a small amount of a glass milk prior to sample addition. These silica particles settle very quickly and can be "pelleted" by allowing a tube to stand for ~3 minutes or by pulse spinning for a few seconds with a table-top pulse spin centrifuge, and washes can simply be poured off.

Figure 21B:
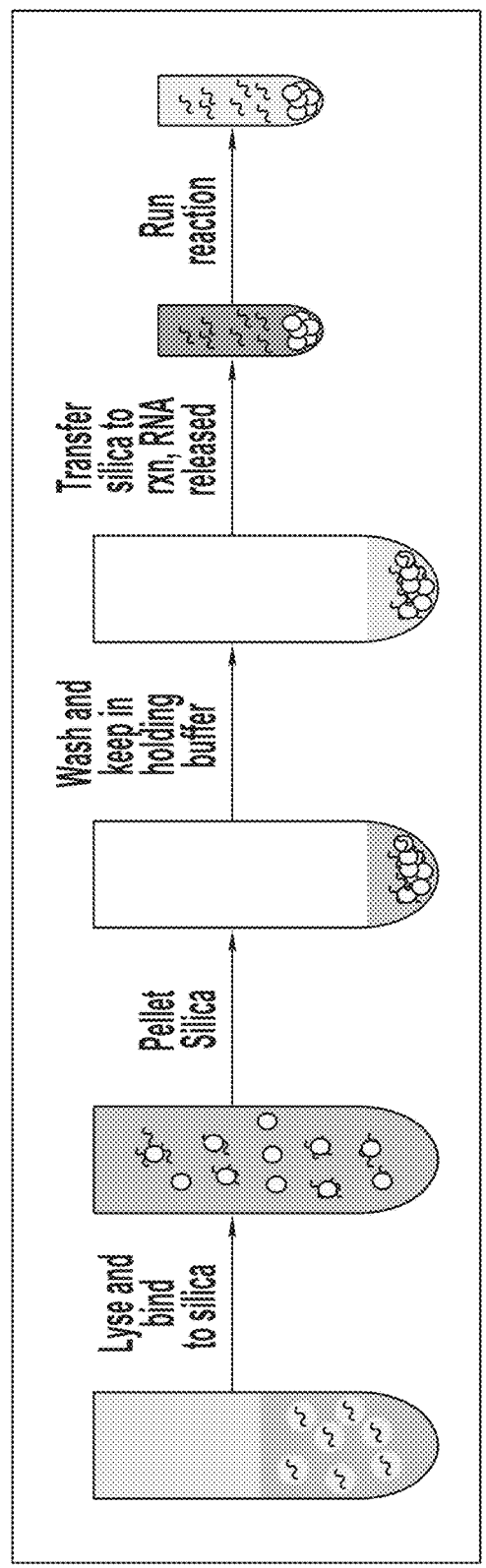
Figure 21E:
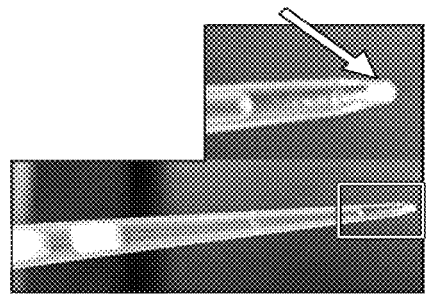
Figure 21D:
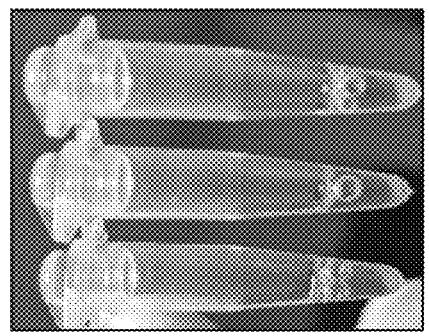
Figure 21C:
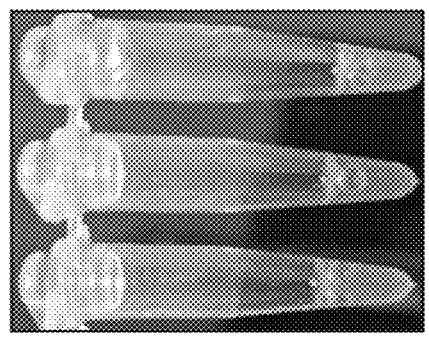

The sample preparation protocol provided herein is very simple (FIG. 21B). The nucleic acids are bound to the silica particles in a lysis/binding buffer which is then poured off to be replaced by an 80% ethanol wash which is then poured off. Finally, a 1 M GuSCN 0.33% TritonX100 "holding solution" is added and poured off. Between each step the silica is pelleted either by gravity or a pulse spin. This protocol leaves the nucleic acids bound to silica particles in a small volume of holding solution, in which RNAses from throat swabs are not very active (FIG. 24A-24C). 1 µl of this slurry can be added directly to a 25 µl colorimetric RT-LAMP. This dilutes the GuSCN sufficiently (40 mM) to prevent inhibition of the RT-LAMP reaction (FIG. 18A-18B) and to release the RNA from the silica particles. The silica particles themselves simply remain inert at the bottom of the tube.

Testing Sensitivity of HMS Assay 1e with Glass Milk Purification

Figure 22A:
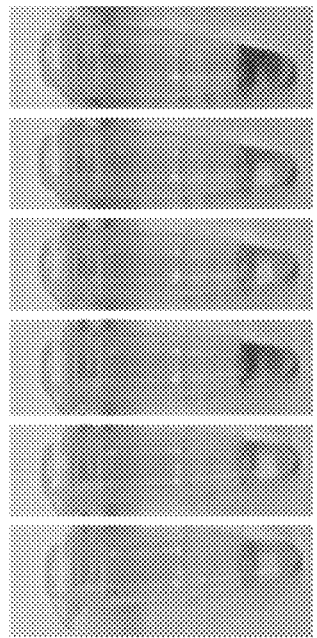
FIG. 22A-22C shows sensitivity test of glass milk purification protocol. Simulated sample purification performed with mock sample (throat and nasal swabs in 1×PBS). Control genomes were spiked into lysis/binding buffer and glass milk prior to adding to sample (to protect RNA from sample RNAse activity). Genome numbers added (1×104, 5×103, or 0) simulated 20, 10, or 0 genomes per microliter in a 0.5 ml mock sample. Following purification, resulting RNA-silica slurry added to 25 μl HMS Assay 1e RT-LAMP reactions without (FIG. 22A) and with (FIG. 22B) control genomes added separately. Reactions were run for 30 minutes at 65 C.
Figure 22B:
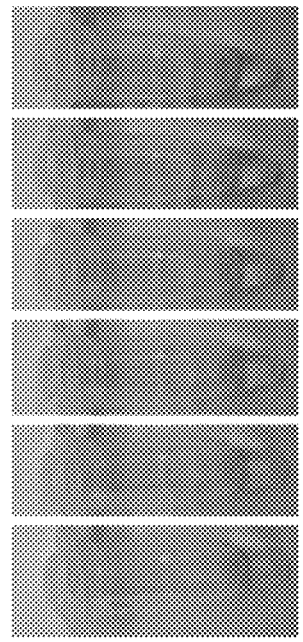
Figure 22C:
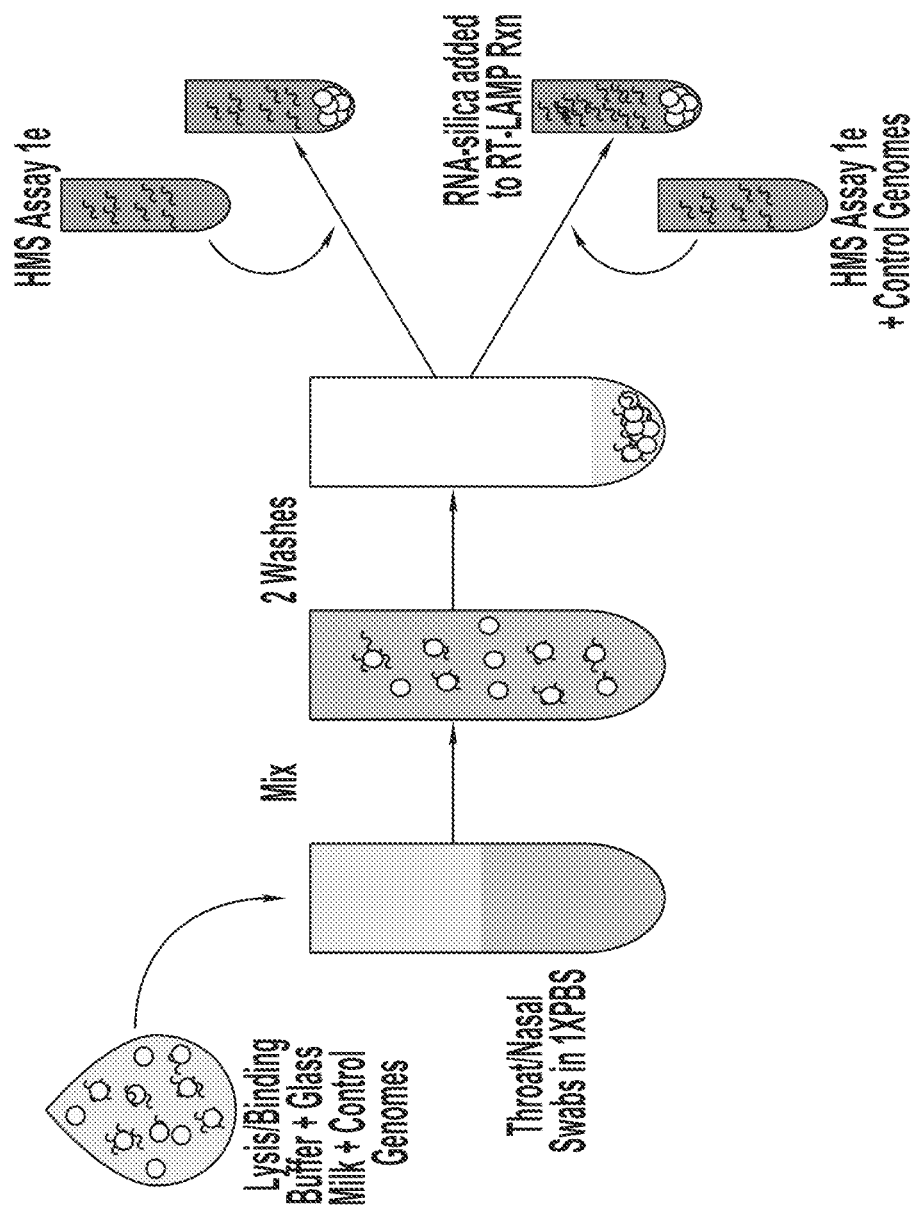

In order to test the sensitivity of detection with this purification scheme and HMS Assay 1e, we set up mock purifications using throat and nasal swabs in 1×PBS to simulate patient samples. Due to the RNAse activity found in throat and nasal swabs, spike-in control genomes had to be spiked directly into lysis/binding buffer, not into swab samples. This lysis/binding buffer with spike-in genomes and glass milk was then added to 0.5 ml of mock samples (one throat and nasal swab agitated in 3 ml 1×PBS), and the purification was performed (FIG. 22C). For each sample, $1\times10^4$, $5\times10^3$, or 0 control genomes were used, simulating 20, 10, or 0 genomes per microliter of mock sample. Purification was performed using either gravity or pulse-spinning to pellet the silica particles. Following purification, 1 µl of the resulting slurry was used in 25 µl HMS Assay 1e RT-LAMP reactions. For each sample, two reactions were run, one with the slurry only, and one with 1,000 control genomes spiked in directly to test for reaction inhibition. As can be seen in FIG. 22A-22B, this protocol was sufficient to detect the equivalent of 10 genomes per microliter of sample (FIG. 22A) and removed inhibitors sufficiently to allow the RT-LAMP reaction to proceed (FIG. 22B).

Testing Purification Scheme with Saliva Rich Sample

Figure 23A:
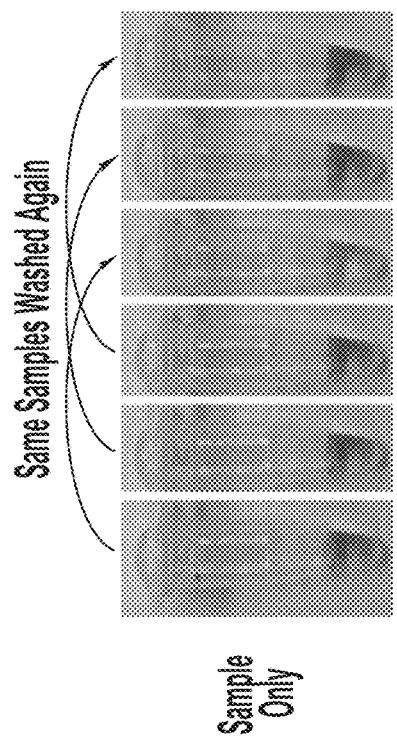
FIG. 23A-23C shows a sensitivity test of glass milk purification protocol with saliva-rich sample. Simulated sample purification performed with mock sample (saliva in 1×PBS). Control genomes were spiked into lysis/binding buffer and glass milk prior to adding to sample (to protect RNA from sample RNAse activity). Genome numbers added (1×104, 5×103, or 0) simulated 20, 10, or 0 genomes per microliter in a 0.5 ml mock sample. Following purification, resulting RNA-silica slurry added to 25 μl HMS Assay 1e RT-LAMP reactions without (FIG. 23A) and with (FIG. 23B) control genomes added separately. Remaining slurry was washed again with holding solution and similarly added to HMS Assay 1e RT-LAMP reactions. Reactions were run for 30 minutes at 65 C.
Figure 23B:
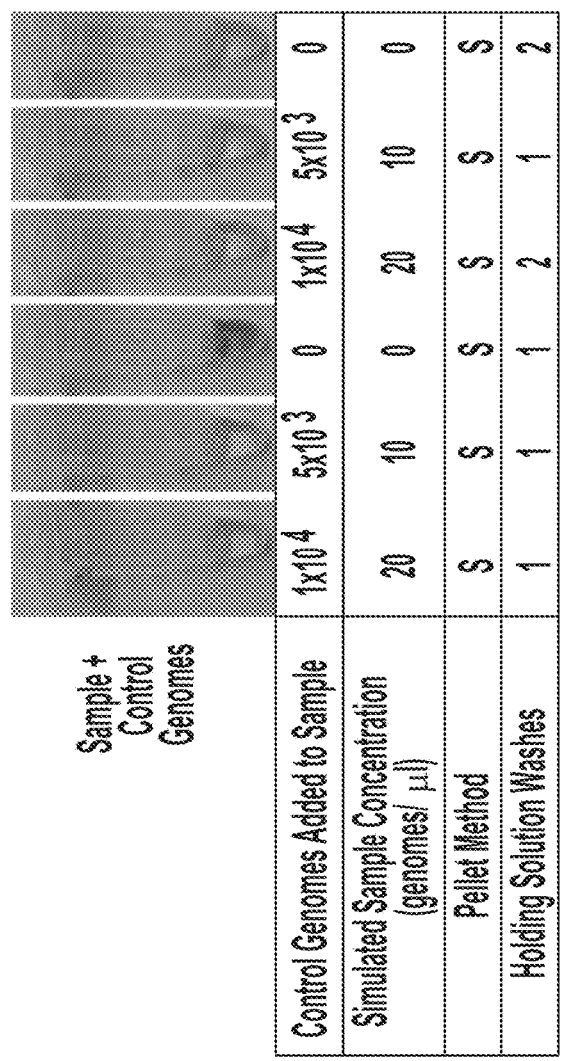
Figure 23C:
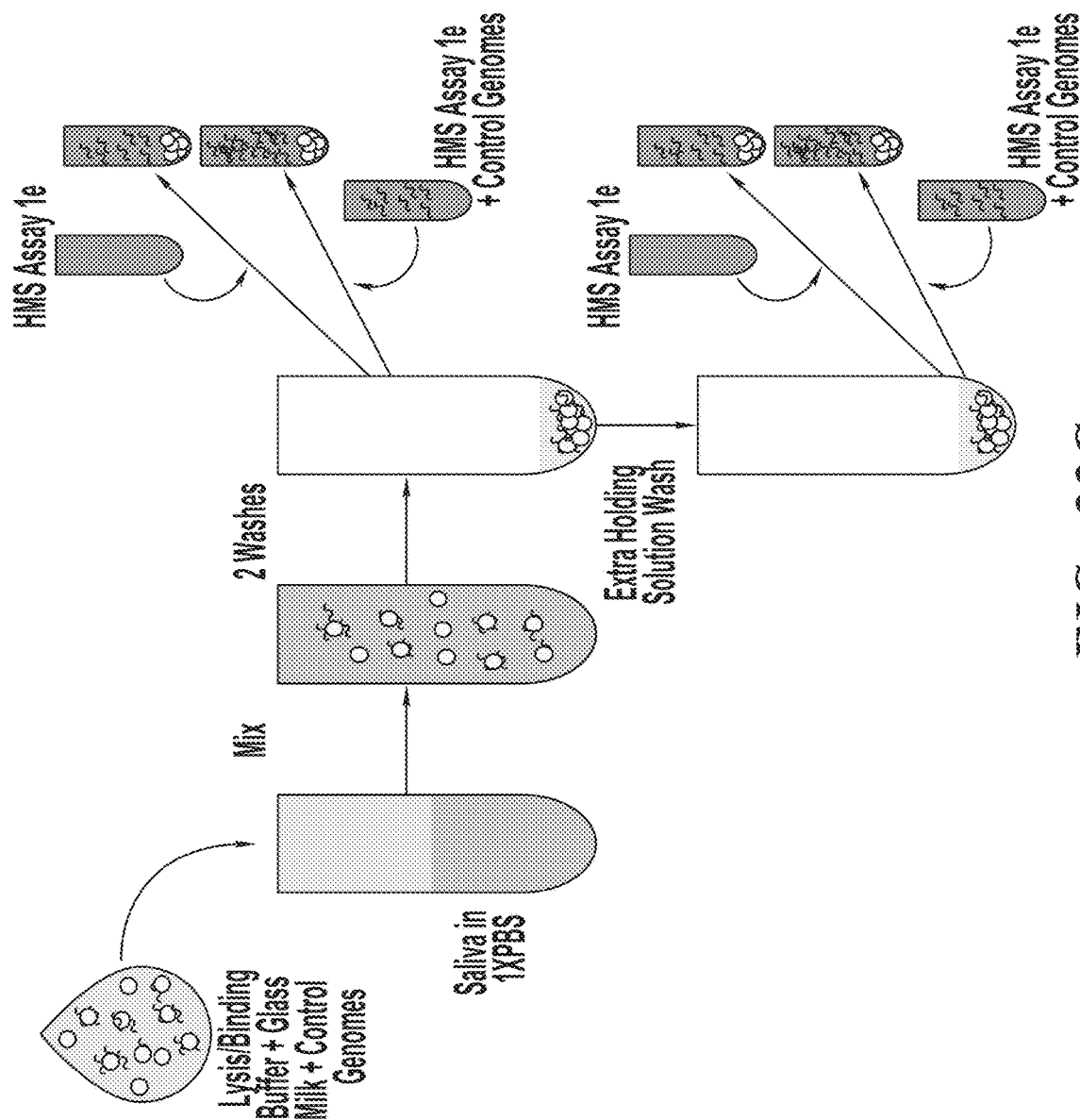

The same sample preparation and purification scheme was repeated as above, with pulse spinning to pellet, using a mock saliva-rich sample (0.5 ml saliva combined with 3 ml 1×PBS). After adding slurry to HMS Assay 1e RT-LAMP reactions, the remaining slurry was washed again in holding solution, and the resulting slurry was used again in HMS Assay 1e RT-LAMP reactions (FIG. 23C). This was done to determine if an additional wash would help to remove inhibitors from saliva-rich samples. As can be seen, saliva appears to decrease sensitivity and can introduce inhibitors of RT-LAMP reactions (FIG. 23A-23B). Following the standard protocol with a single wash with holding solution, no reactions without separately added control genomes detected genomes, while two of the three corresponding reactions with spiked in control genomes did. This indicates that the sensitivity was decreased modestly even when enough inhibitors were removed to allow for some amplification. Following another wash with holding solution, the reaction with the sample simulating 20 genomes per microliter detected genomes while all reactions with separately spiked in control genomes did as well. This indicates that the sensitivity can be somewhat rescued by an additional wash step, a simple step to include if samples are particularly saliva heavy. It should also be noted that these saliva-rich mock samples contained more saliva than would typically be found in a swab sample. Furthermore, the improvement of detection following a second holding solution wash indicates that the RNA remains bound to the silica particles in the holding solution and thus does not become diluted upon further washes.

Figures 24A, 24B, 24C:
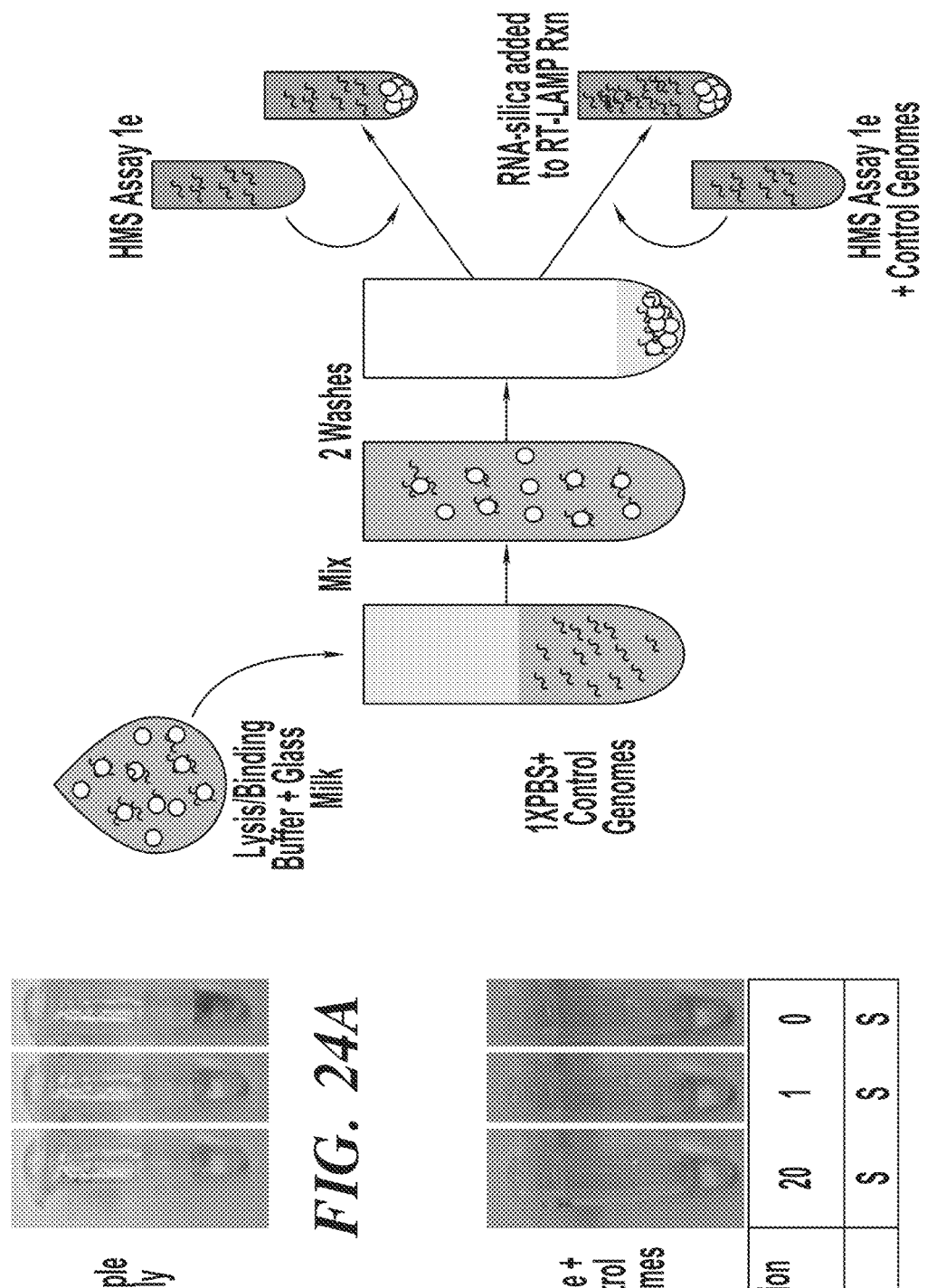
FIG. 24A-24C demonstrates the verification of relevant binding conditions. Simulated sample purification performed with 0.5 ml of 1×PBS containing 20, 10, or 0 control genomes. Following purification, resulting RNA-silica slurry was added to 25 μl HMS Assay 1e RT-LAMP reactions without (FIG. 24A) and with (FIG. 24B) control genomes added separately. Reactions were run for 30 minutes at 65 C.
Figure 25B:
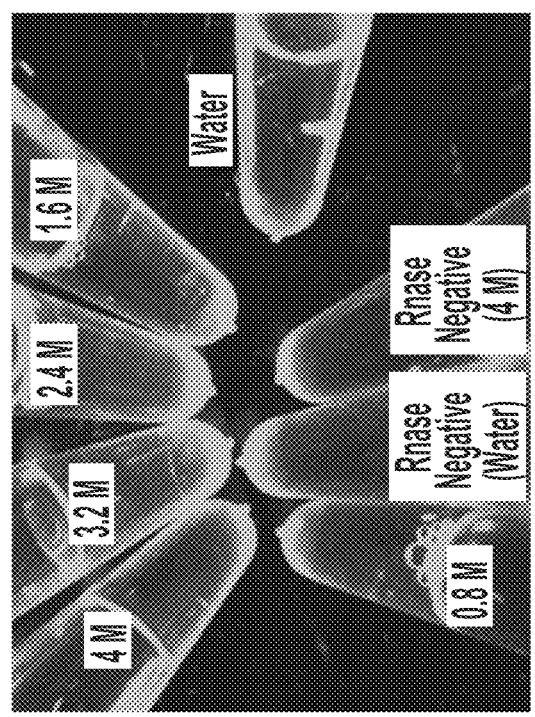
FIG. 25A-25B shows verification of RNAse Inactivation in Low GuSCN Concentrations. Throat swabs were resuspended in 0.8M-4M GuSCN or water. 40 μl was used in an RNAseAlert RNAse detection reaction incubated for 30 minutes at 37 C (fluorescence indicates RNAse activity). Negative control reactions were run using clean water or clean 4 M GuSCN.
Figure 25A:
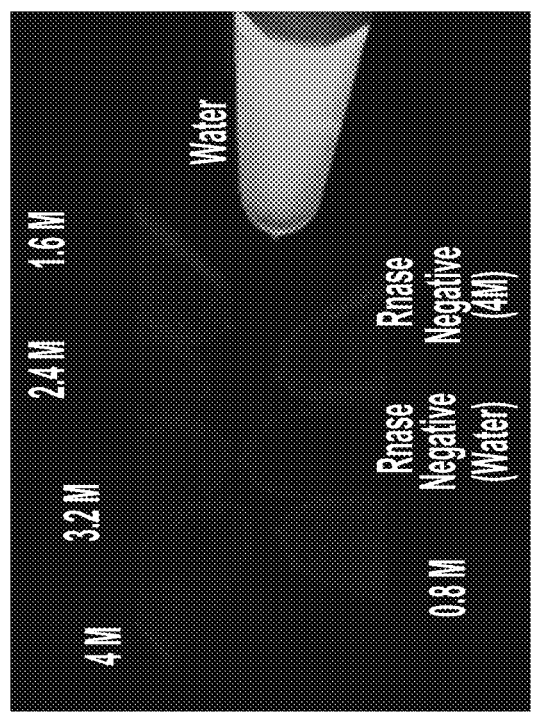
Figure 27:
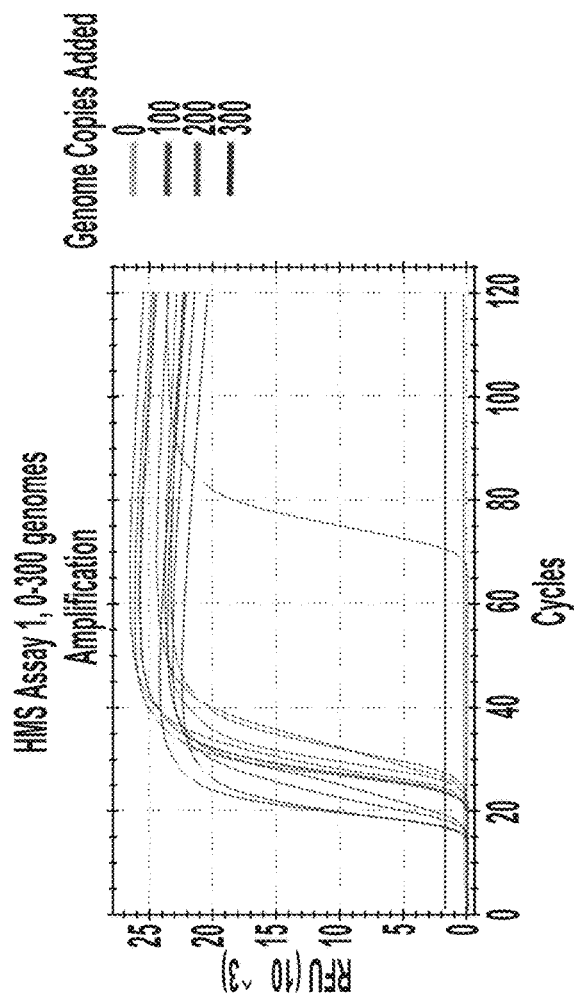
FIG. 27 shows results from HMS Assay 1, 0-300 genomes.
Figure 28:
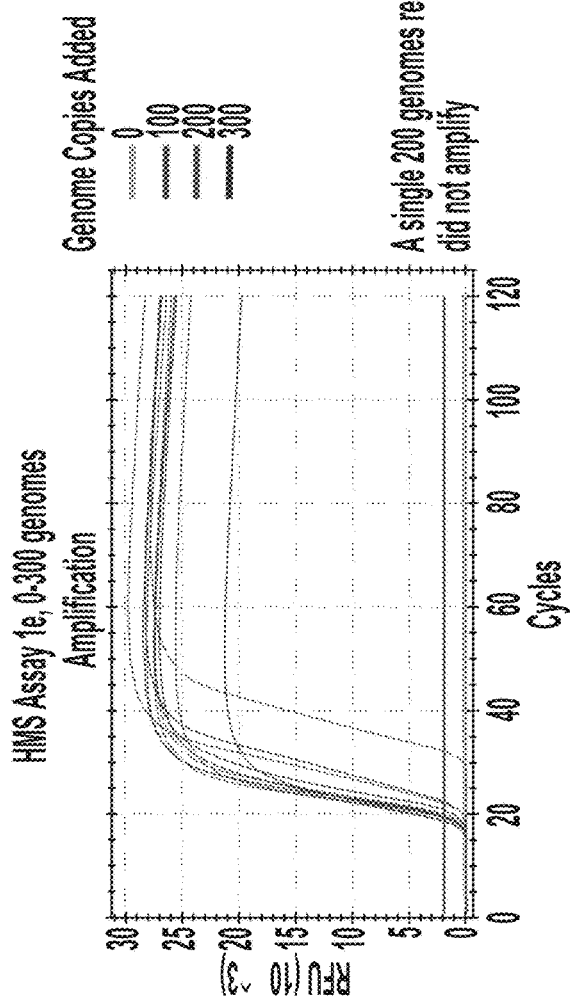
FIG. 28 shows results from HMS Assay 1e, 0-300 genomes.
Figure 29:
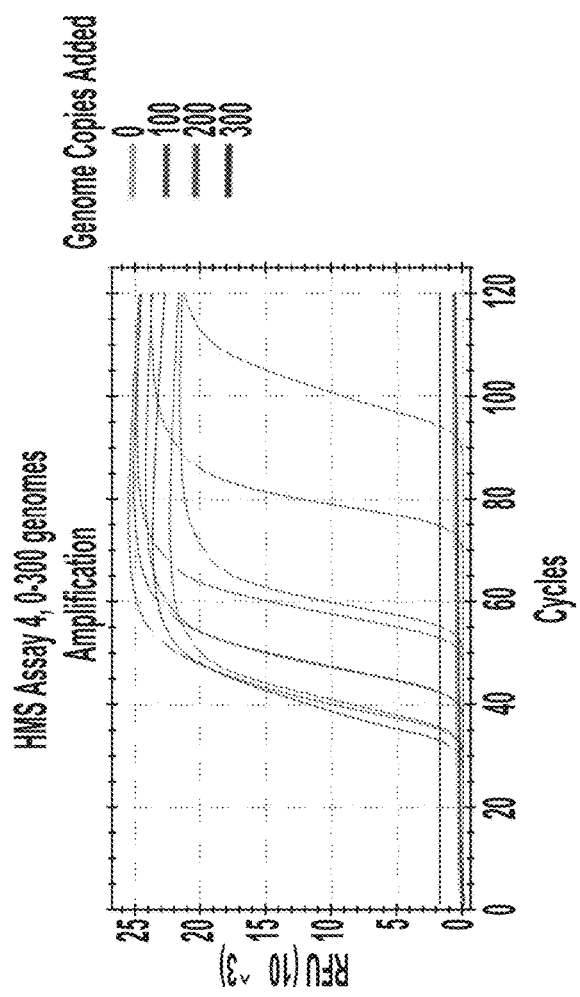
FIG. 29 shows results from HMS Assay 4, 0-300 genomes.
Figure 30:
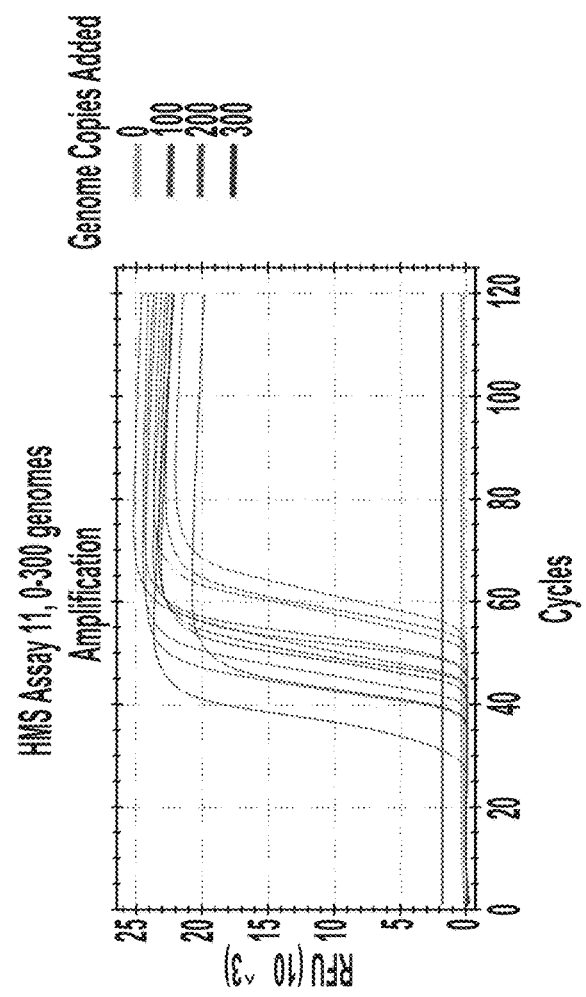
FIG. 30 shows results from HMS Assay 11, 0-300 genomes.
Figure 31:
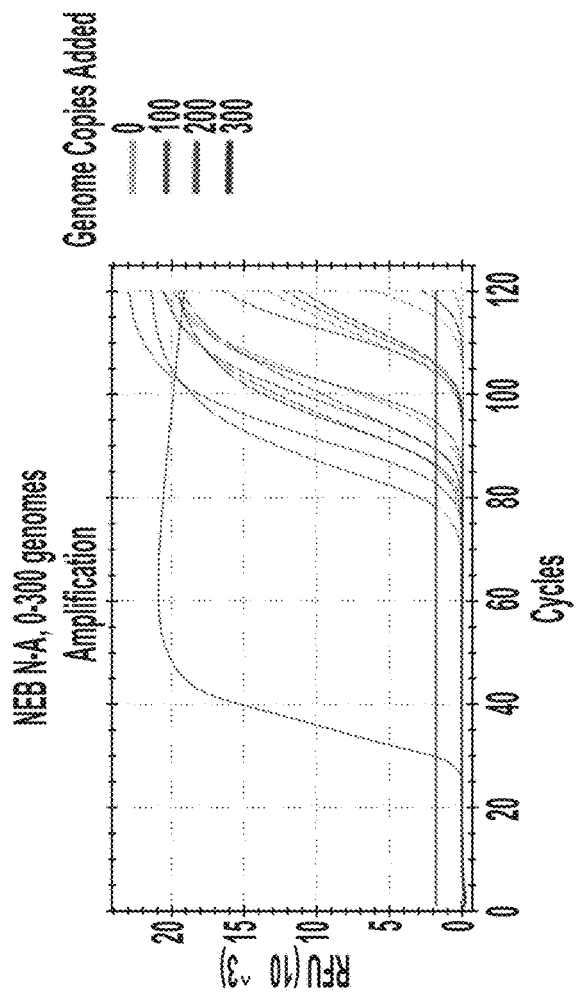
FIG. 31 shows results from NEB N-A, 0-300 genomes.
Figure 32:
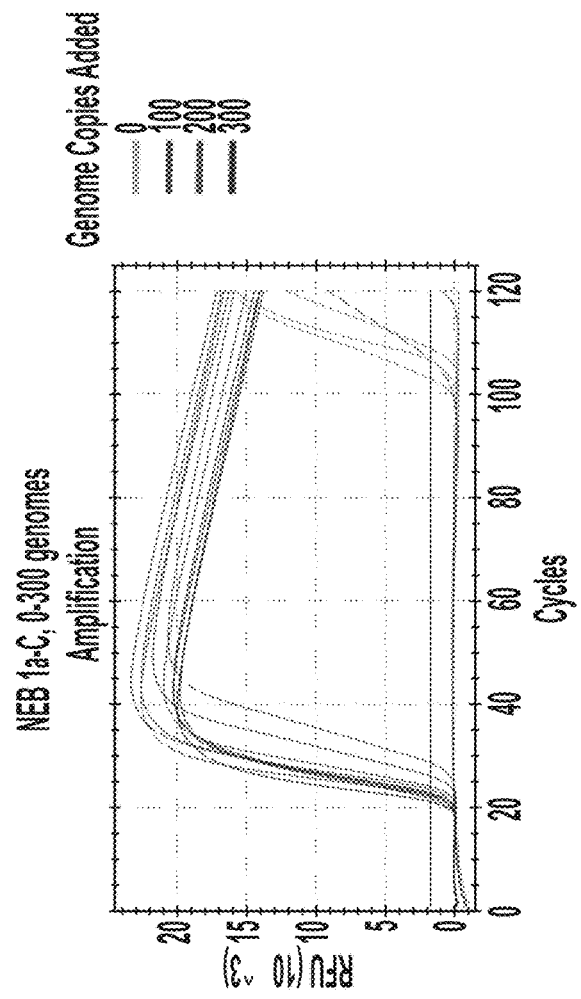
FIG. 32 shows results from NEB 1a-C, 0-300 genomes.
Figure 33:
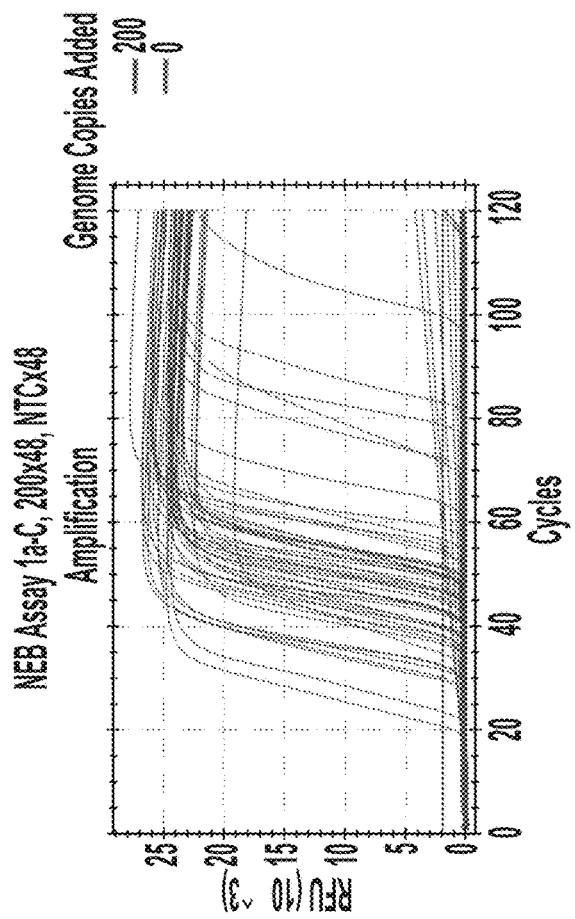
FIG. 33 shows results from NEB Assay 1a-C, 200×48, NTC×48.
Figure 34:
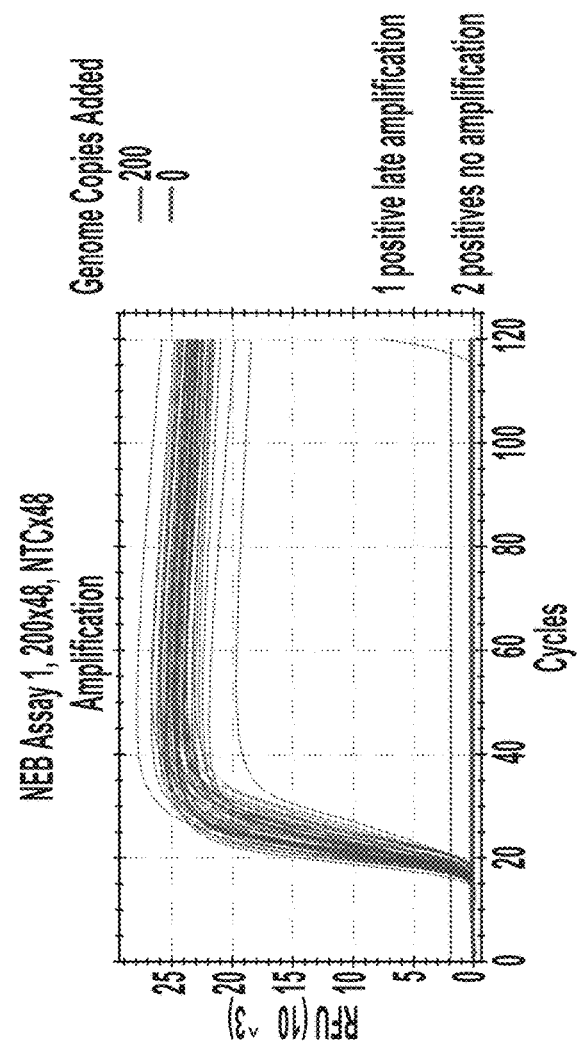
FIG. 34 shows results from HMS Assay 1, 200×48, NTC×48.
Figure 35:
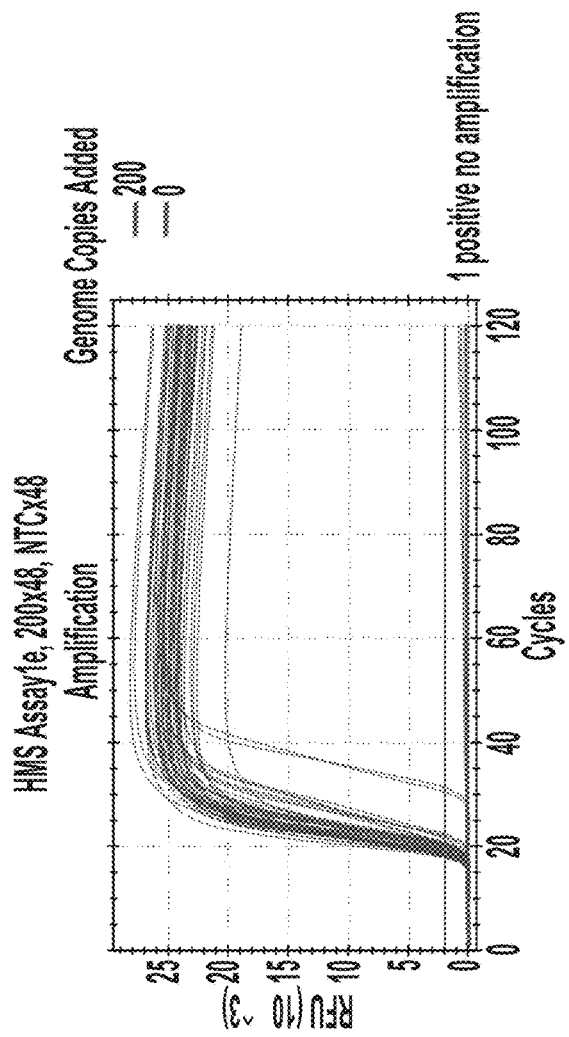
FIG. 35 shows results from HMS Assay 1e, 200×48, NTC×48.
Figure 36:
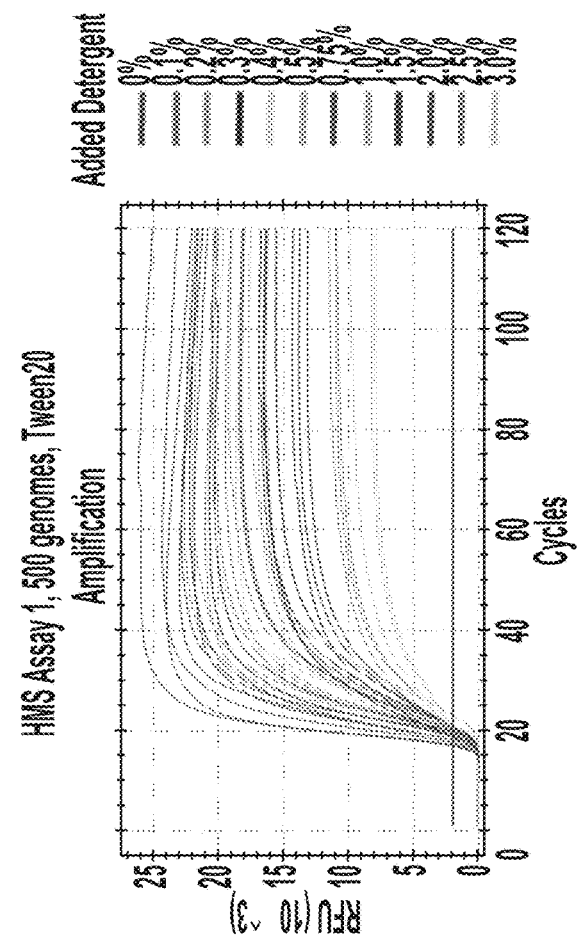
FIG. 36 shows results from HMS Assay 1, 500 genomes Tween 20.
Figure 37:
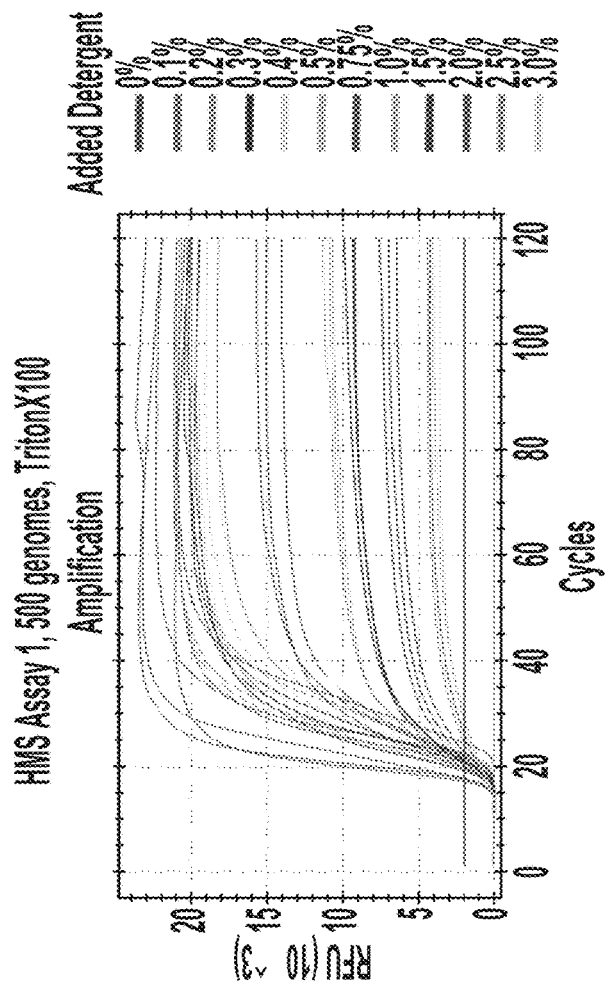
FIG. 37 shows results from HMS Assay 1, 500 genomes, Triton X 100.
Figure 38:
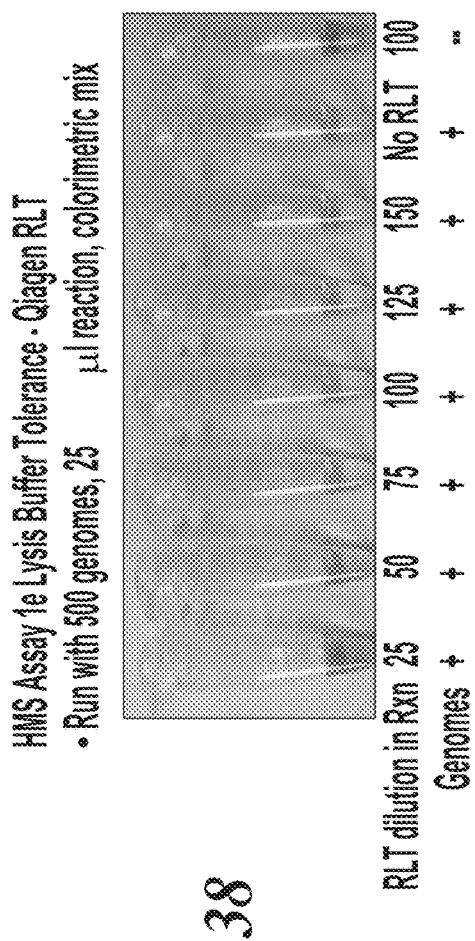
FIG. 38 and FIG. 39 show HMS Assay 1e Lysis Buffer Tolerance with Qiagen RLT buffer.
Figure 39:
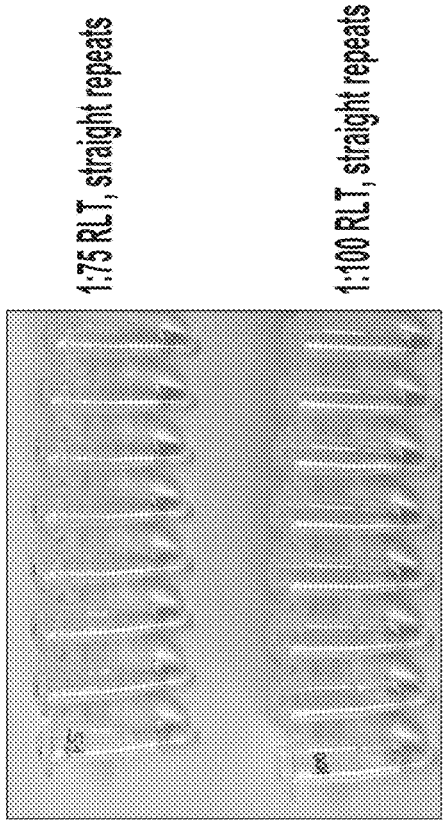
Figure 40:
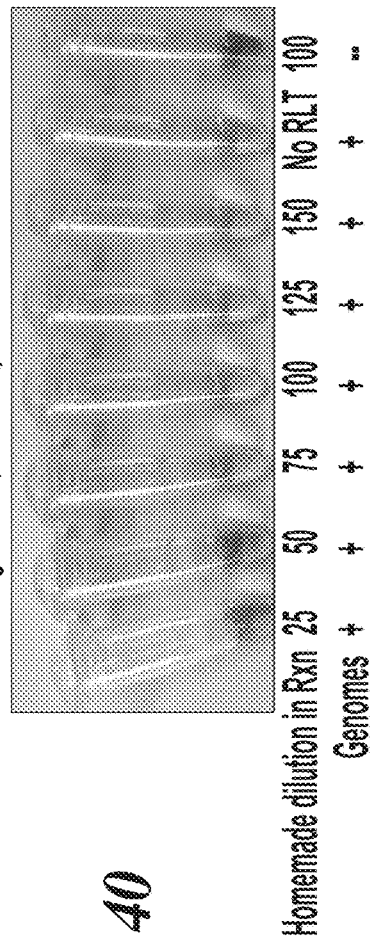
FIG. 40 and FIG. 41 show HMS Assay 1e Lysis Buffer Tolerance with Homemade lysis buffer.
Figure 41:
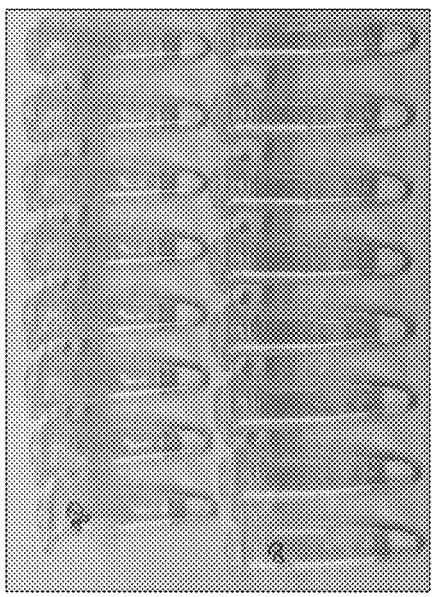
Figure 42:
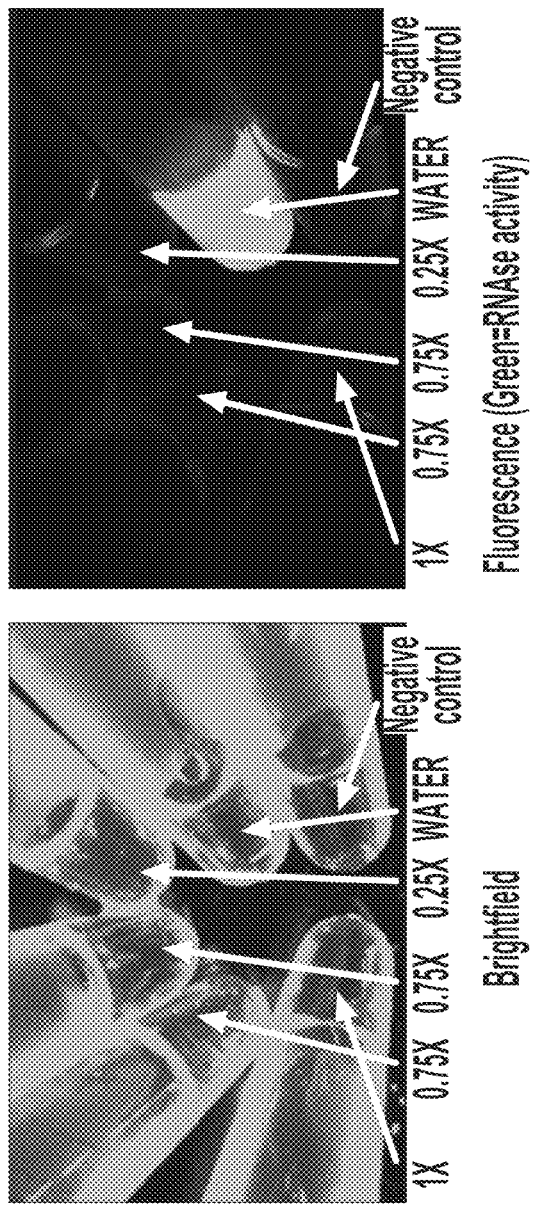
FIG. 42 shows throat swab samples and varying concentrations of RLT buffer.
Figure 43:
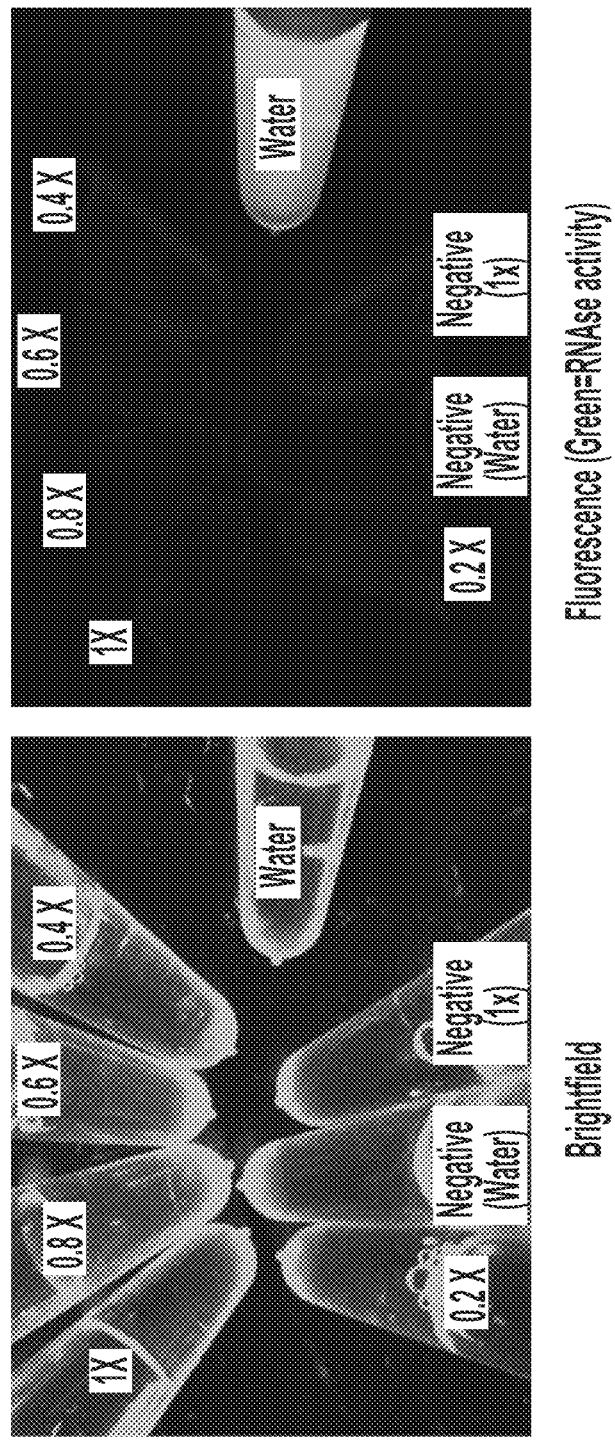
FIG. 43 shows throat swab samples and varying concentrations of homemade lysis buffer.
Figure 44:
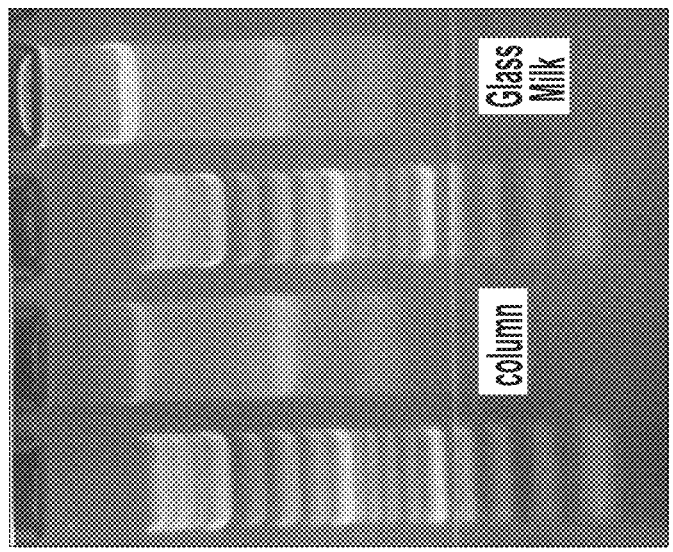
FIG. 44 shows that homemade lysis buffer can be used to purify nucleic acids from 293T cells with a column or with glass beads.
Figure 45:
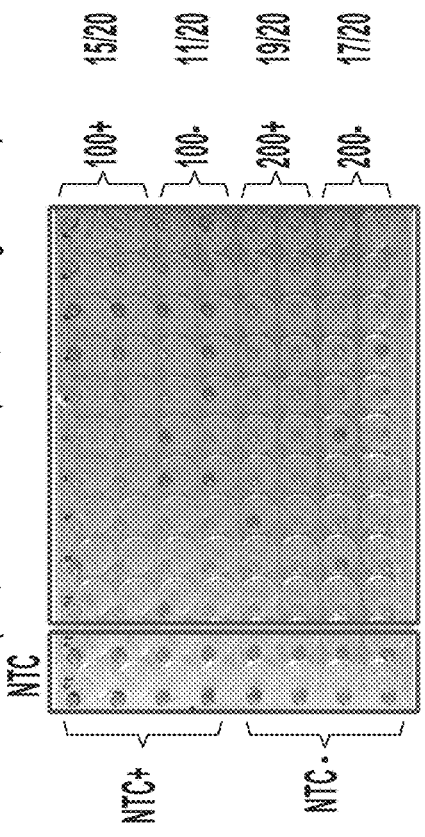
FIG. 45 shows colorimetric HMS Assay 1.
Figure 46:
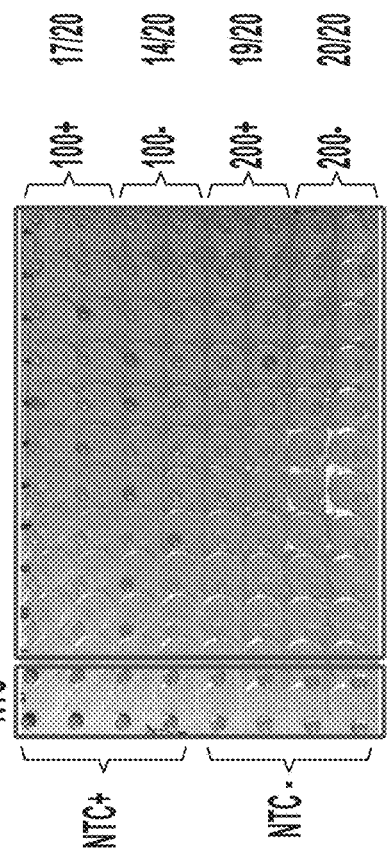
FIG. 46 shows colorimetric HMS Assay 1e.
Figure 47:
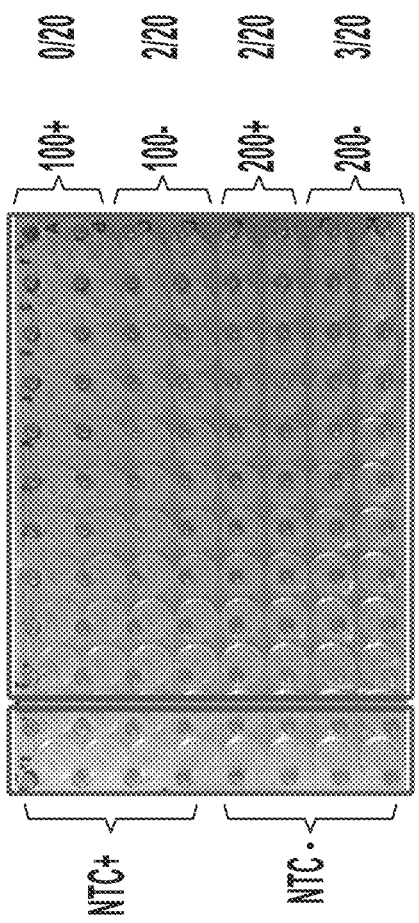
FIG. 47 and FIG. 48 show colorimetric NEB 1a-C.
Figure 48:
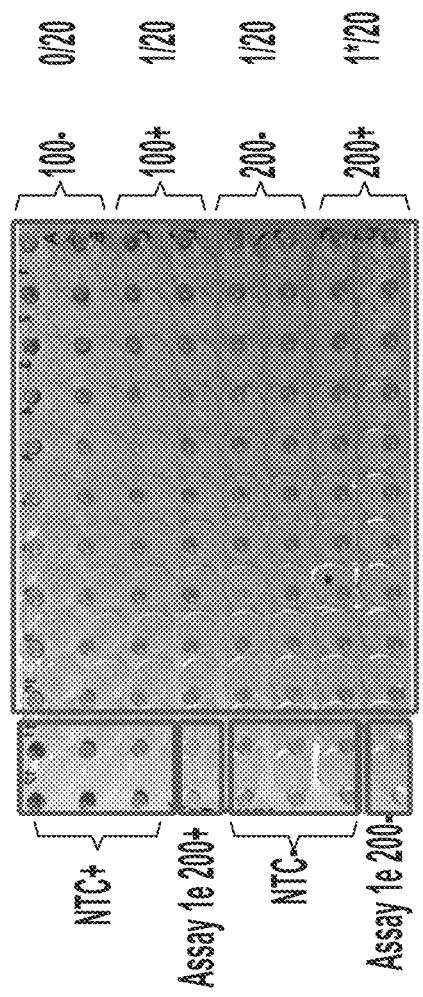
Figure 49:
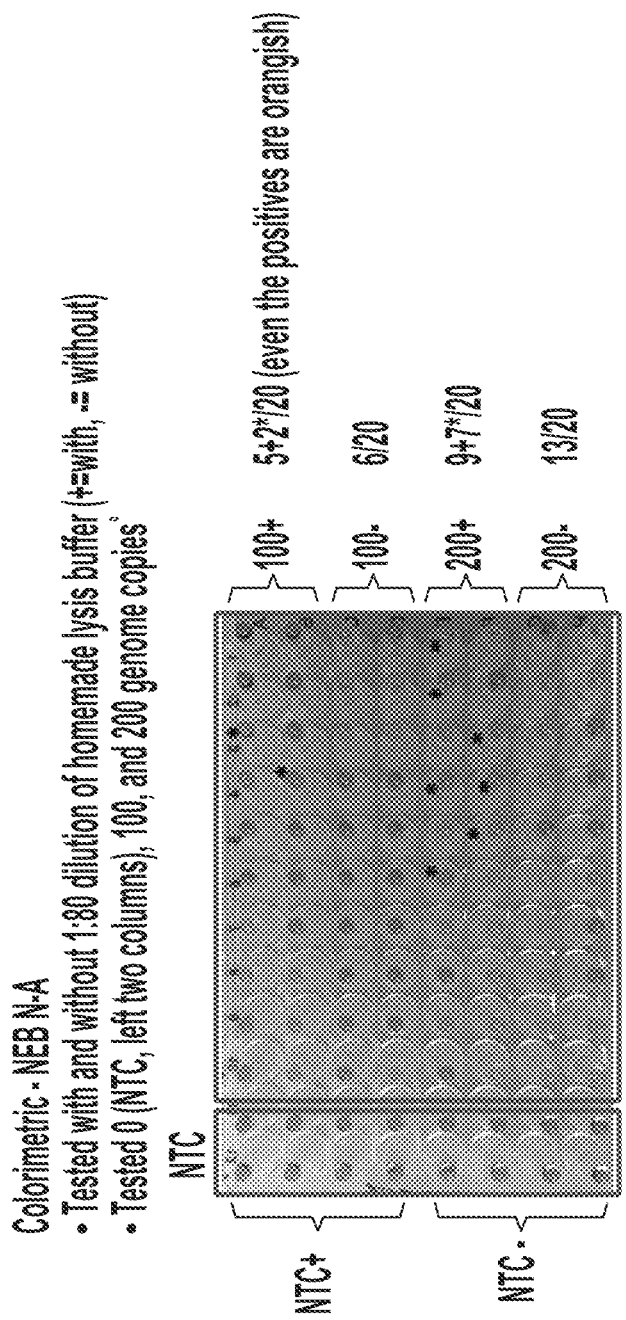
FIG. 49 shows results from a colorimetric NEB N-A Assay tested with and without 1:80 dilution of homemade lysis buffer.

Ensuring RNA Binding in Relevant Conditions and RNAse Inactivation in Low Concentration GuSCN Solutions To ensure that RNA will bind to the silica particles when first diluted in an aqueous solution, we tried the same purification using clean 1×PBS into which the positive control RNA's were added prior to addition of the lysis/binding buffer with glass milk (FIG. 24A-24C). In order to ensure that RNAse activity is inhibited in holding solution, throat swabs were placed into 200 d of various GuSCN solutions and then assayed with IDT's RNAseAlert kit to assess residual RNAse activity (40 ul used in a 50 µl detection reaction, FIG. 25A-25B). As can be seen, RNAse activity is undetectable even in 0.8 M GuSCN after 30 minutes at 37 C (holding solution contains 1 M GuSCN). These experiments together indicate that RNA diluted in a sample prior to addition of lysis/binding buffer will bind to the silica particles and that RNAse activity is minimal in the holding solution.

Discussion

In this report, we have presented evidence of an extremely sensitive RT-LAMP assay for the SARS-CoV-2 virus made even more sensitive by a rapid and highly accessible purification scheme compatible with current collection methods in which swabs are placed into a large volume of collection media. This purification scheme and RT-LAMP assay are simple and fast, and do not rely on specialized equipment.

The silica particles used for purification are made from a crude silica dioxide powder and can be prepared in enormous quantities very quickly and very little is used per purification (one liter is enough for at least 500,000 purifications). A single lab could easily make enough for an entire state or more, allowing for institutions with basic equipment like centrifuges and autoclaves to generate enough supply to meet demand for an entire country. This purification can be performed in a single tube without a centrifuge using only three buffers in minutes and easily in parallel, allowing for efficient purification by medical personnel in point-of-care institutions.

The RT-LAMP assay (HMS Assay 1e) provided herein is fast and sensitive, and when used with NEB's colorimetric LAMP mix, can be run in 30 minutes with nothing more than a heat block. On its own HMS Assay 1e is sensitive down to 100-200 genomes. However, due to the inability to directly add more than 1 µl of sample to a reaction, this sensitivity may not be enough for samples with low viral titers. However, when combined with the glass milk purification protocol provided herein, the sensitivity is greatly increased, allowing for detection of 10 genomes per microliter of sample and only adding a few minutes to the testing protocol, less with a pulse spin mini centrifuge.

Given the incredible demand for tests for COVID 19, a collection of tests with different components from different industry sources will be important for addressing the immediate shortage of tests in the face of a sweeping pandemic. Thus, this test protocol can serve an important function and can be more sensitive than many of tests reaching the market now.

Materials and Methods

Assay 1/1e Primer Design: The primary oligos for Assay 1/1e, F3, B3, FIP, and BIP primers, were designed by PrimerExplorer V5 (https://primerexplorer.jp/e/). The loop primers (LF and LB) were designed by hand, checking for appropriate melting temperatures using SnapGene software predictions.

Oligos: All oligos were ordered from IDT and resuspended in UltraPure water at a 100 µM concentration. Oligos were combined to make a 10× primer mix as follows—16 µl FIP, 16 µl BIP, 2 µl F3, 2 µl B3, 4 µl LF, 4 µl LB.

RT-LAMP Reactions: All RT-LAMP reactions were setup as described by NEB protocols (E1700 and M1800) and run at 65 C. Fluorescence based reactions were run as 10 µl reactions in a Bio-Rad CFX96 thermocycler for 60 minutes monitored every 30 seconds for fluorescence in the SYBR channel. Colorimetric assays were run as 25 µl reactions for 30 minutes at 65 C in an Eppendorf thermocycler. Colorimetric assays were imaged using a Pixel 2 smartphone with basic settings.

Control Genomes: All genomes used in this study were purified RNA controls from Twist Bioscience (Sku 102019, $1 \times 10^6$ genomes per microliter) diluted appropriately in nuclease free water.

Clean Reaction Setup: All reactions were assembled and sealed prior to running in a dedicated clean room that was regularly decontaminated with bleach and had limited personnel access. Once reactions were run, the reaction tubes or plates were never opened again to prevent post-amplification contamination of future reactions.

Solutions: All solutions were created from molecular grade reagents. To make the lysis/binding buffer, first a 6 M GuSCN 2% TritonX100 solution was made by dissolving 35.5 g GuSCN (Millipore Sigma G9277) and 1.06 g (1 ml) TritonX100 (Millipore Sigma T8787) in enough UltraPure water (ThermoFisher Scientific 10977015) to bring the volume to 49 ml. The pH was adjusted to 8 with approximately 40 µl of 1N NaOH. To create the lysis/binding buffer, 10 ml of this is combined with 16.16 ml of 100% ethanol (VWR 71002-426). Prior to use, glass milk is added such that 2 µl of glass milk will be used per sample. Other GuSCN solutions were prepared in a similar fashion and diluted where indicated with UltraPure water. Holding solution was made by combining 8 ml of the previously described 6 M GuSCN, 2% TritonX100 solution with 40 ml of UltraPure water.

Glass Milk Preparation: To prepare glass milk, 325 mesh silicon dioxide (Spectrum Chemicals—SI108) is combined with an excess volume of 10% HCl (~3 N HCl) made from combining 37% HCl (Millipore Sigma 320331) and MilliQ water (Millipore) in a fume hood (dry silica powder should not be inhaled). After acid washing was allowed to continue for 4-8 hours at room temperature, beads are pelleting by spinning 2 minutes at 5,000×g and the supernatant is poured off. The pellet is resuspended in 4 pellet volumes of MilliQ water and then pelleted again. This wash step is repeated for a total of 6 washes. Then pellet is then washed with 4 pellet volumes of 10 mM Tris HCl, pH=8 (ThermoFisher Scientific AM9855G) and 1 mM EDTA (ThermoFisher Scientific 15575020) brought up in MilliQ water and pelleted. Finally, the pellet is resuspended in 1 pellet volume of 10 mM Tris HCl and 1 mM EDTA and autoclaved. The resulting 50% glass milk slurry can be stored at room temperature. Before use, the silica particles are vigorously resuspended.

RNAse Activity determination: RNAse activity was tested using IDT's RNAseAlert substrate (IDT 11-04-02-03). Briefly, the detection substrate (an RNA oligo with a fluor and quencher) was resuspended in UltraPure water at a 10 µM. For each test, 5 µl of this and 5 µl of 10× buffer was combined with 40 µl of solution created by submerging in and vigorously agitating 200 µl of the designated GuSCN solution with a cotton tip applicator (Puritan 806-WC) swabbed thoroughly at the back of the throat. A positive control was created by submerging a swab in water, and a negative control had clean UltraPure water used without any additions. These reactions were then incubated for 30 minutes at 37 C and imaged in brightfield and 488 nm with a Leica stereoscope.

Mock Samples: Mock samples were created in 1×PBS. To simulate a typical swab collection, one nasopharyngeal and one oropharyngeal swab were submerged and agitated in 3 ml 1×PBS. For a simulated saliva-rich sample, 0.5 ml of saliva was combined with 3 ml of 1×PBS.

Test Purifications: For all test purifications, 654 µl lysis/binding buffer combined with 2 µl of glass milk was added to 500 µl of sample. In the case of the typical swab and saliva-rich samples, the lysis/binding buffer and glass milk was first combined with 0 µl, 0.5 µl, or 1 µl of SARS-CoV-2 control genomes at 10,000 genomes per microliter to simulate 0, 10, and 20 genomes per microliter for the 500 µl sample. For the 1×PBS control samples, the control genomes were instead spiked directly into 500 µl of 1×PBS which was then used as the sample.

Once the sample, lysis/binding buffer and glass milk were all combined and mixed, the silica particles were pelleted either by standing for 3-5 minutes (G) or by pulse spinning (S) for 2-3 seconds in a pulse spin mini centrifuge (VWR galaxy mini, 6 positions). All purifications were performed in 2 ml Eppendorf SafeLock tubes (Eppendorf 022363344), whose rounded bottom allowed for more effective pouring off of supernatant than small volume tubes. After pelleting, the supernatant was gently poured off. The pellet was resuspended in 700 µl of 80% ethanol. For purifications using gravity, resuspension was accomplished simply by adding solution quickly down the side of the tube, if using a centrifuge tubes were flicked to resuspend. Silica particles were again pelleted and the solution poured off. The pellet was then resuspended in 700 µl of holding solution. After pelleting again, the supernatant was again poured off. The pellet was then left in the residual holding solution. 1 µl of silica particles was taken with a pipette off the bottom of the tube and added to a 25 µl colorimetric LAMP reaction with or without 1000 genomes spiked in separately as a positive control. Reactions were flicked to resuspend beads and then pulse spun to pellet before incubating for 30 minutes at 65 C.

REFERENCES

1. Yinhua Zhang, N. O., Jin Xiong, Luo Sun, Raphael Ohuru Nyaruaba, Hongping Wei, Nathan A. Tanner, Rapid Molecular Detection of SARS-CoV-2 (COVID-19) Virus RNA Using Colorimetric LAMP. MedRxiv, 2020.

2. Nagamine, K., T. Hase, and T. Notomi, Accelerated reaction by loop-mediated isothermal amplification using loop primers. Mol Cell Probes, 2002. 16(3): p. 223-9.
3. Calvert, A. E., et al., Rapid colorimetric detection of Zika virus from serum and urine specimens by reverse transcription loop-mediated isothermal amplification (RT-LAMP). PLoS One, 2017. 12(9): p. e0185340.
4. Poole, C. B., et al., Colorimetric tests for diagnosis of filarial infection and vector surveillance using non-instrumented nucleic acid loop-mediated isothermal amplification (NINA-LAMP). PLoS One, 2017. 12(2): p. e0169011.
5. Torres, C., et al., LAVA: an open-source approach to designing LAMP (loop-mediated isothermal amplification) DNA signatures. BMC Bioinformatics, 2011. 12: p. 240.
6. Boom, R., et al., Rapid and simple method for purification of nucleic acids. J Clin Microbiol, 1990. 28(3): p. 495-503.
7. Coronavirus Disease 2019 (COVID-19) Guidelines for Clinical Specimens. Centers for Disease Control.

The contents of the references provided herein above are incorporated by reference in their entirety.

Example 6: Rt-Lamp Assays for SARS-CoV-2 Detection Supplemental Experiments

The methods, compositions, and assays provided herein were optimized for use in the detection of the SARS-COV-2 virus. Additional examples of reaction mixtures and assays that can be used are shown in FIGS. 27-49.

We claim:

1. A composition for loop-mediated isothermal amplification (LAMP) of a SARS-coronavirus-2 (COVID-19) nucleic acid, comprising:
   (i) a first nucleic acid strand (first primer) comprising a nucleotide sequence CGGTGGACAAATTGTCAC (SEQ ID NO: 1);
   (ii) a second nucleic acid strand (second primer) comprising a nucleotide sequence of CTTCTCTGGATTTAACACACTT (SEQ ID NO: 2)
   (iii) a third nucleic acid strand (third primer) comprising a nucleotide sequence of TCAGCACACAAAGCCAAAAATTTATCTGTGCAAAGGAAATTAAGGAG (SEQ ID NO: 3) or TCAGCACACAAAGCCAAAAATTTATTTTCTGTGCAAAGGAAATTAAGGAG (SEQ ID NO: 4);
   (iv) a fourth nucleic acid strand (fourth primer) comprising a nucleotide sequence of TATTGGTGGAGCTAAACTTAAAGCCCTGTACAATCCCTTTGAGTG (SEQ ID NO: 5) or TATTGGTGGAGCTAAACTTAAAGCCTTTTCTGTACAATCCCTTTGA GTG (SEQ ID NO: 6);
   (v) a fifth nucleic acid strand (fifth primer) comprising a nucleotide sequence of TTACAAGCTTAAAGAATGTCTGAACACT (SEQ ID NO: 7); and
   (vi) a sixth nucleic acid strand (sixth primer) comprising a nucleotide sequence of TTGAATTTAGGTGAAACATTTGTCACG (SEQ ID NO: 8).

2. The composition of claim 1, further comprising one or more reagents or buffers for loop-mediated isothermal amplification of a nucleic acid.

3. The composition of claim 1, further comprising a colorimetric reagent.

4. The composition of claim 1, further comprising dNTPs.

5. The composition of claim 1, further comprising a polymerase enzyme.

6. The composition of claim 1, further comprising a reverse transcriptase.

7. The composition of claim 1, further comprising a buffer solution for loop-mediated isothermal amplification of a nucleic acid.

8. The composition of claim 1, further comprising a detergent.

9. The composition of claim 1, further comprising a sample suspected of comprising SARS-coronavirus-2.

10. A kit for detecting SARS-coronavirus-2, the kit comprising the composition of claim 1, reagents and packaging materials thereof.

11. The kit of claim 10, further comprising a nucleic acid strand comprising a nucleotide sequence complementary to SEQ ID NO: 1, SEQ ID NO: 2, SEQ ID NO: 3, SEQ ID NO: 4, SEQ ID NO: 5, SEQ ID NO: 6, SEQ ID NO: 7, and/or SEQ ID NO: 8.

12. The kit of claim 10, wherein the reagents comprise reagents for loop-mediated isothermal amplification of a nucleic acid, and/or wherein the kit further comprises a buffer solution for loop-mediated isothermal amplification of a nucleic acid.

13. An assay for detecting a SARS-coronavirus-2 nucleic acid in a sample, the assay comprising:
   (a) contacting a sample with a composition of any one of claims 1-8 to produce a reaction mixture, wherein the reaction mixture comprises one or more reagents or buffers for loop-mediated isothermal amplification of a nucleic acid; and (b) heating the reaction mixture of step (a) to a temperature of about 65° C. for a period of time, wherein production of an amplification product in the reaction mixture indicates the presence of a SARS-coronavirus-2 in the sample.

14. The assay of claim 13, wherein the sample is a biological sample, and further comprising obtaining the biological sample from a subject having or suspected of having a SARS-coronavirus-2 infection.

15. The assay of claim 13, further comprising cooling the reaction mixture from step (b) to room temperature.

16. The assay of claim 13, further comprising a lysis step prior to step (a).

17. The assay of claim 13, further comprising a step of nucleic acid isolation or purification prior to step (a).

18. The assay of claim 13, further comprising a step of isolating or purifying the SARS-coronavirus-2 nucleic acid sample, where said isolating or purifying comprises contacting the sample with silica particles.

19. The assay of claim 13, wherein the reaction mixture further comprises a denaturing agent.

20. The assay of claim 13, wherein the reaction mixture further comprises guanidinium thiocyanate or guanidinium isothiocyanate.

* * * * *

```
                        SEQUENCE LISTING

<160> NUMBER OF SEQ ID NOS: 11

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cggtggacaa attgtcac                                                  18

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cttctctgga tttaacacac tt                                             22

<210> SEQ ID NO 3
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcagcacaca aagccaaaaa tttatctgtg caaaggaaat taaggag                  47

<210> SEQ ID NO 4
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcagcacaca aagccaaaaa tttattttc tgtgcaaagg aaattaagga g              51

<210> SEQ ID NO 5
<211> LENGTH: 45
<212> TYPE: DNA
```

-continued

<213> ORGANISM: Artificial Sequence
<220> FEATURE:
<223> OTHER INFORMATION: Description of Artificial Sequence: Synthetic
      primer

<400> SEQUENCE: 5
tattggtgga gctaaactta aagccctgta caatccctttt gagtg                    45

<210> SEQ ID NO 6
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tattggtgga gctaaactta aagccttttc tgtacaatcc ctttgagtg                 49

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttacaagctt aaagaatgtc tgaacact                                        28

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttgaatttag gtgaaacatt tgtcacg                                         27

<210> SEQ ID NO 9
<211> LENGTH: 1260
<212> TYPE: DNA
<213> ORGANISM: Severe acute respiratory syndrome coronavirus 2

<400> SEQUENCE: 9
atgtctgata atggacccca aaatcagcga aatgcacccc gcattacgtt tggtggaccc     60
tcagattcaa ctggcagtaa ccagaatgga gaacgcagtg gggcgcgatc aaaacaacgt    120
cggccccaag gtttacccaa taatactgcg tcttggttca ccgctctcac tcaacatggc    180
aaggaagacc ttaaattccc tcgaggacaa ggcgttccaa ttaacaccaa tagcagtcca    240
gatgaccaaa ttggctacta ccgaagagct accagacgaa ttcgtggtgg tgacggtaaa    300
atgaaagatc tcagtccaag atggtatttc tactacctag gaactgggcc agaagctgga    360
cttccctatg gtgctaacaa agacggcatc atatgggttg caactgaggg agccttgaat    420
acaccaaaag atcacattgg cacccgcaat cctgctaaca atgctgcaat cgtgctacaa    480
cttcctcaag gaacaacatt gccaaaaggc ttctacgcag aagggagcag aggcggcagt    540
caagcctctt ctcgttcctc atcacgtagt cgcaacagtt caagaaattc aactccaggc    600
agcagtaggg gaacttctcc tgctagaatg gctggcaatg gcggtgatgc tgctcttgct    660
ttgctgctgc ttgacagatt gaaccagctt gagagcaaaa tgtctggtaa aggccaacaa    720

```
caacaaggcc aaactgtcac taagaaatct gctgctgagg cttctaagaa gcctcggcaa      780
aaacgtactg ccactaaagc atacaatgta acacaagctt tcggcagacg tggtccagaa      840
caaacccaag gaaattttgg ggaccaggaa ctaatcagac aaggaactga ttacaaacat      900
tggccgcaaa ttgcacaatt tgcccccagc gcttcagcgt tcttcggaat gtcgcgcatt      960
ggcatggaag tcacaccttc gggaacgtgg ttgacctaca caggtgccat caaattggat     1020
gacaaagatc caaatttcaa agatcaagtc attttgctga ataagcatat tgacgcatac     1080
aaaacattcc caccaacaga gcctaaaaag acaaaaaga agaaggctga tgaaactcaa     1140
gccttaccgc agagacagaa gaaacagcaa actgtgactc ttcttcctgc tgcagatttg     1200
gatgatttct ccaaacaatt gcaacaatcc atgagcagtg ctgactcaac tcaggcctaa     1260
```

<210> SEQ ID NO 10
<211> LENGTH: 21290
<212> TYPE: DNA
<213> ORGANISM: Severe acute respiratory syndrome coronavirus 2

<400> SEQUENCE: 10

```
atggagagcc ttgtccctgg tttcaacgag aaaacacacg tccaactcag tttgcctgtt       60
ttacaggttc gcgacgtgct cgtacgtggc tttggagact ccgtggagga ggtcttatca      120
gaggcacgtc aacatcttaa agatggcact tgtggcttag tagaagttga aaaggcgtt      180 ttgcctcaac ttgaacagcc ctatgtgttc atcaaacgtt cggatgctcg aactgcacct      240
catggtcatg ttatggttga gctggtagca gaactcgaag cattcagta cggtcgtagt      300 ggtgagacac ttggtgtcct tgtccctcat gtgggcgaaa taccagtggc ttaccgcaag      360
gttcttcttc gtaagaacgg taataaagga gctggtggcc atagttacgg cgccgatcta      420
aagtcatttg acttaggcga cgagcttggc actgatcctt atgaagattt tcaagaaaac      480
tggaacacta acatagcag tggtgttacc cgtgaactca tgcgtgagct aacggaggg      540 gcatacactc gctatgtcga taacaacttc tgtggccctg atggctaccc tcttgagtgc      600
attaaagacc ttctagcacg tgctggtaaa gcttcatgca cttgtccga caactggac      660 tttattgaca ctaagagggg tgtatactgc tgccgtgaac atgagcatga aattgcttgg      720
tacacggaac gttctgaaaa gagctatgaa ttgcagacac cttttgaaat taaattggca      780
aagaaatttg acaccttcaa tggggaatgt ccaaattttg tatttcctt aaattccata      840 atcaagacta ttcaaccaag ggttgaaaag aaaaagcttg atggctttat gggtagaatt      900
cgatctgtct atccagttgc gtcaccaaat gaatgcaacc aaatgtgcct tcaactctc      960 atgaagtgtg atcattgtgg tgaaacttca ggcagacgg gcgatttgt taaagccact     1020 tgcgaatttt gtggcactga aatttgact aaagaaggtg ccactacttg tggttactta     1080
ccccaaaatg ctgttgttaa atttattgt ccagcatgtc acaattcaga gtaggacct     1140 gagcatagtc ttgccgaata ccataatgaa tctggcttga aaccattct tcgtaagggt     1200 ggtcgcacta ttgcctttgg aggctgtgtg ttctcttatg ttggttgcca taacaagtgt     1260
gcctattggg ttccacgtgc tagcgctaac ataggttgta accatacagg tgttgttgga     1320
gaaggttccg aaggtcttaa tgacaacctt cttgaaatac tccaaaaaga gaaagtcaac     1380
atcaatattg ttggtgactt taaacttaat gaagagatcg ccattatttt ggcatctttt     1440
tctgcttcca caagtgcttt tgtggaaact gtgaaaggtt tggattataa agcattcaaa     1500
caaattgttg aatcctgtgg taattttaaa gttacaaaag gaaaagctaa aaaaggtgcc     1560
```

```
tggaatattg gtgaacagaa atcaatactg agtcctcttt atgcatttgc atcagaggct    1620
gctcgtgttg tacgatcaat tttctcccgc actcttgaaa ctgctcaaaa ttctgtgcgt    1680
gttttacaga aggccgctat aacaatacta gatggaattt cacagtattc actgagactc    1740
attgatgcta tgatgttcac atctgatttg gctactaaca atctagttgt aatggcctac    1800
attacaggtg gtgttgttca gttgacttcg cagtggctaa ctaacatctt tggcactgtt    1860
tatgaaaaac tcaaacccgt ccttgattgg cttgaagaga gtttaagga aggtgtagag    1920 tttcttagag acggttggga aattgttaaa tttatctcaa cctgtgcttg tgaaattgtc    1980
ggtggacaaa ttgtcacctg tgcaaaggaa attaaggaga gtgttcagac attctttaag    2040
cttgtaaata aattttttggc tttgtgtgct gactctatca ttattggtgg agctaaactt    2100
aaagccttga atttaggtga aacatttgtc acgcactcaa agggattgta cagaaagtgt    2160
gttaaatcca gagaagaaac tggcctactc atgcctctaa agccccaaa agaaattatc    2220 ttcttagagg gagaaacact tcccacagaa gtgttaacag aggaagttgt cttgaaaact    2280
ggtgatttac aaccattaga caacctact agtgaagctg ttgaagctcc attggttggt    2340
acaccagttt gtattaacgg gcttatgttg ctcgaaatca agacacaga aaagtactgt    2400 gcccttgcac ctaatatgat ggtaacaaac aataccttca cactcaaagg cggtgcacca    2460
acaaaggtta ctttttggtga tgacactgtg atagaagtgc aaggttacaa gagtgtgaat    2520 atcactttg aacttgatga aaggattgat aaagtactta atgagaagtg ctctgcctat    2580
acagttgaac tcggtacaga agtaaatgag ttcgcctgtg ttgtggcaga tgctgtcata    2640
aaaactttgc aaccagtatc tgaattactt acaccactgg gcattgattt agatgagtgg    2700
agtatggcta catactactt atttgatgag tctggtgagt ttaaattggc ttcacatatg    2760
tattgttctt tctaccctcc agatgaggat gaagaagaag gtgattgtga agaagaagag    2820
tttgagccat caactcaata tgagtatggt actgaagatg attaccaagg taaacctttg    2880
gaatttggtg ccacttctgc tgctcttcaa cctgaagaag agcaagaaga agattggtta    2940
gatgatgata gtcaacaaac tgttggtcaa caagacggca gtgaggacaa tcagacaact    3000
actattcaaa caattgttga ggttcaacct caattagaga tggaacttac accagttgtt    3060
cagactattg aagtgaatag ttttagtggt tatttaaaac ttactgacaa tgtatacatt    3120
aaaaatgcag acattgtgga agaagctaaa aaggtaaaac caacagtggt tgttaatgca    3180
gccaatgttt accttaaaca tggaggaggt gttgcaggag ccttaaataa ggctactaac    3240
aatgccatgc aagttgaatc tgatgattac atagctacta tggaccact taaagtgggt    3300 ggtagttgtg ttttaagcgg acacaatctt gctaaacact gtcttcatgt tgtcggccca    3360
aatgttaaca aggtgaaga cattcaactt cttaagagtg cttatgaaaa ttttaatcag    3420
cacgaagttc tacttgcacc attattatca gctggtattt ttggtgctga ccctatacat    3480
tctttaagag tttgtgtaga tactgttcgc acaaatgtct acttagctgt ctttgataaa    3540
aatctctatg acaaacttgt ttcaagcttt ttggaaatga gagtgaaaa gcaagttgaa    3600 caaaagatcg ctgagattcc taaagaggaa gttaagccat ttataactga agtaaaccct    3660
tcagttgaac agagaaaaca agatgataag aaaatcaaag cttgtgttga agaagttaca    3720
acaactctgg aagaaactaa gttcctcaca gaaaacttgt tactttatat tgacattaat    3780
ggcaatcttc atccagattc tgccactctt gttagtgaca ttgacatcac tttcttaaag    3840
aaagatgctc catatatagt gggtgatgtt gttcaagagg gtgttttaac tgctgtggtt    3900
atacctacta aaaaggctgg tggcacatact gaaatgctag cgaaagcttt gagaaaagtg    3960
```

```
ccaacagaca attatataac cacttacccg ggtcagggtt taaatggtta cactgtagag    4020
gaggcaaaga cagtgcttaa aaagtgtaaa agtgcctttt acattctacc atctattatc    4080
tctaatgaga agcaagaaat tcttggaact gtttcttgga atttgcgaga atgcttgca    4140 catgcagaag aaacacgcaa attaatgcct gtctgtgtgg aaactaaagc catagtttca    4200
actatacagc gtaaatataa gggtattaaa atacaagagg gtgtggttga ttatggtgct    4260
agattttact tttacaccag taaaacaact gtagcgtcac ttatcaacac acttaacgat    4320
ctaaatgaaa ctcttgttac aatgccactt ggctatgtaa cacatggctt aaatttggaa    4380
gaagctgctc ggtatatgag atctctcaaa gtgccagcta cagtttctgt ttcttcacct    4440
gatgctgtta cagcgtataa tggttatctt acttcttctt ctaaaacacc tgaagaacat    4500
tttattgaaa ccatctcact tgctggttcc tataaagatt ggtcctattc tggacaatct    4560
acacaactag gtatagaatt tcttaagaga ggtgataaaa gtgtatatta cactagtaat    4620
cctaccacat tccacctaga tggtgaagtt atcacctttg acaatcttaa gacacttctt    4680
tctttgagag aagtgaggac tattaaggtg tttacaacag tagacaacat taacctccac    4740
acgcaagttg tggacatgtc aatgacatat ggacaacagt ttggtccaac ttatttggat    4800
ggagctgatg ttactaaaat aaaacctcat aattcacatg aaggtaaaac atttatgtt    4860 ttacctaatg atgacactct acgtgttgag gcttttgagt actaccacac aactgatcct    4920
agttttctgg gtaggtacat gtcagcatta aatcacacta aaaagtggaa atacccacaa    4980
gttaatggtt taacttctat taaatgggca gataacaact gttatcttgc cactgcattg    5040
ttaacactcc aacaaataga gttgaagttt aatccacctg ctctacaaga tgcttattac    5100
agagcaaggg ctggtgaagc tgctaacttt tgtgcactta tcttagccta ctgtaataag    5160
acagtaggtg agttaggtga tgttagagaa acaatgagtt acttgtttca acatgccaat    5220
ttagattctt gcaaaagagt cttgaacgtg gtgtgtaaaa cttgtggaca acagcagaca    5280
acccttaagg gtgtagaagc tgttatgtac atgggcacac tttcttatga acaatttaag    5340
aaaggtgttc agataccttg tacgtgtggt aaacaagcta caaatatctc agtacaacag    5400
gagtcacctt ttgttatgat gtcagcacca cctgctcagt atgaacttaa gcatggtaca    5460
tttacttgtg ctagtgagta cactggtaat taccagtgtg gtcactataa acatataact    5520
tctaaagaaa ctttgtattg catagacggt gctttactta caaagtcctc agaatacaaa    5580
ggtcctatta cggatgtttt ctacaaagaa aacagttaca caacaaccat aaaaccagtt    5640
acttataaat tggatggtgt tgtttgtaca gaaattgacc ctaagttgga caattattat    5700
aagaaagaca attcttattt cacagagcaa ccaattgatc ttgtaccaaa ccaaccatat    5760
ccaaacgcaa gcttcgataa ttttaagttt gtatgtgata atatcaaatt tgctgatgat    5820
ttaaaccagt taactggtta taagaaacct gcttcaagag agcttaaagt tacattttc     5880 cctgacttaa atggtgatgt ggtggctatt gattataaac actacacacc ctcttttaag    5940
aaaggagcta aattgttaca taaacctatt gtttggcatg ttaacaatgc aactaataaa    6000
gccacgtata aaccaaatac ctggtgtata cgttgtcttt ggagcacaaa accagttgaa    6060
acatcaaatt cgtttgatgt actgaagtca gaggacgcgc agggaatgga taatcttgcc    6120
tgcgaagatc taaaaccagt ctctgaagaa gtagtggaaa atcctaccat acagaaagac    6180
gttcttgagt gtaatgtgaa aactaccgaa gttgtaggag acattatact taaaccagca    6240
aataatagtt taaaaattac agaagaggtt ggccacacag atctaatggc tgcttatgta    6300
```

```
gacaattcta gtcttactat taagaaacct aatgaattat ctagagtatt aggtttgaaa    6360
acccttgcta ctcatggttt agctgctgtt aatagtgtcc cttgggatac tatagctaat    6420
tatgctaagc cttttcttaa caaagttgtt agtacaacta ctaacatagt tacacggtgt    6480
ttaaaccgtg tttgtactaa ttatatgcct tatttcttta ctttattgct acaattgtgt    6540
acttttacta gaagtacaaa ttctagaatt aaagcatcta tgccgactac tatagcaaag    6600
aatactgtta agagtgtcgg taaattttgt ctagaggctt catttaatta tttgaagtca    6660
cctaattttt ctaaactgat aaatattata atttggtttt tactattaag tgtttgccta    6720
ggttctttaa tctactcaac cgctgcttta ggtgttttaa tgtctaattt aggcatgcct    6780
tcttactgta ctggttacag agaaggctat ttgaactcta ctaatgtcac tattgcaacc    6840
tactgtactg gttctatacc ttgtagtgtt tgtcttagtg gtttagattc tttagacacc    6900
tatccttctt tagaaactat acaaattacc atttcatctt ttaaatggga tttaactgct    6960
tttggcttag ttgcagagtg gtttttggca tatattcttt tcactaggtt tttctatgta    7020
cttgattgg ctgcaatcat gcaattgttt ttcagctatt ttgcagtaca tttattagt    7080
aattcttggc ttatgtggtt aataattaat cttgtacaaa tggccccgat ttcagctatg    7140
gttagaatgt acatcttctt tgcatcattt tattatgtat ggaaaagtta tgtgcatgtt    7200
gtagacggtt gtaattcatc aacttgtatg atgtgttaca aacgtaatag agcaacaaga    7260
gtcgaatgta caactattgt taatggtgtt agaaggtcct tttatgtcta tgctaatgga    7320
ggtaaaggct tttgcaaact acacaattgg aattgtgtta attgtgatac attctgtgct    7380
ggtagtacat ttattagtga tgaagttgcg agagacttgt cactacagtt taaaagacca    7440
ataaatccta ctgaccagtc ttcttacatc gttgatagtg ttacagtgaa gaatggttcc    7500
atccatcttt actttgataa agctggtcaa aagacttatg aaagacattc tctctctcat    7560
tttgttaact tagacaaacct gagagctaat aacactaaag gttcattgcc tattaatgtt    7620
atagttttttg atggtaaatc aaaatgtgaa gaatcatctg caaaatcagc gtctgtttac    7680
tacagtcagc ttatgtgtca acctatactg ttactagatc aggcattagt gtctgatgtt    7740
ggtgatagtc cggaagttgc agttaaaatg tttgatgctt acgttaatac gttttcatca    7800
acttttaacg taccaatgga aaaactcaaa acactagttg caactgcaga agctgaactt    7860
gcaaagaatg tgtccttaga caatgtctta tctactttta tttcagcagc tcggcaaggg    7920
tttgttgatt cagatgtaga aactaaagat gttgttaat gtcttaaatt gtcacatcaa    7980
tctgacatag aagttactgg cgatagttgt aataactata tgctcaccta taacaaagtt    8040
gaaaacatga caccccgtga ccttggtgct tgtattgact gtagtgcgcg tcatattaat    8100
gcgcaggtag caaaaagtca caacattgct ttgatatgga acgttaaaga tttcatgtca    8160
ttgtctgaac aactacgaaa acaaatacgt agtgctgcta aaaagaataa cttacctttt    8220
aagttgacat gtgcaactac tagacaagtt gttaatgttg taacaacaaa gatagcactt    8280
aagggtggta aaattgttaa taattggttg aagcagttaa ttaaagttac acttgtgttc    8340
cttttttgttg ctgctatttt ctatttaata acacctgttc atgtcatgtc taaacatact    8400
gacttttcaa gtgaaatcat aggatacaag gctattgatg gtgtgtcac tcgtgacata    8460
gcatctacag atacttgttt tgctaacaaa catgctgatt ttgacacatg gtttagccag    8520
cgtggtggta gttatactaa tgacaaagct tgcccattga ttgctgcagt cataacaaga    8580
gaagtgggtt ttgtcgtgcc tggtttgcct ggcacgatat tacgcacaac taatggtgac    8640
ttttttgcatt tcttacctag agttttttagt gcagttggta acatctgtta cacaccatca    8700
```

```
aaacttatag agtacactga cttttgcaaca tcagcttgtg ttttggctgc tgaatgtaca    8760
attttttaaag atgcttctgg taagccagta ccatattgtt atgataccaa tgtactagaa    8820
ggttctgttg cttatgaaag tttacgccct gacacacgtt atgtgctcat ggatggctct    8880
attattcaat ttcctaacac ctaccttgaa ggttctgtta gagtggtaac aacttttgat    8940
tctgagtact gtaggcacgg cacttgtgaa agatcagaag ctggtgtttg tgtatctact    9000
agtggtagat gggtacttaa caatgattat tacagatctt taccaggagt tttctgtggt    9060
gtagatgctg taaatttact tactaatatg tttacaccac taattcaacc tattggtgct    9120
ttggacatat cagcatctat agtagctggt ggtattgtag ctatcgtagt aacatgcctt    9180
gcctactatt ttatgagggtt tagaagagct tttggtgaat acagtcatgt agttgccttt    9240
aatactttac tattccttat gtcattcact gtactctgtt taacaccagt ttactcattc    9300
ttacctggtg tttattctgt tatttacttg tacttgacat tttatcttac taatgatgtt    9360
tctttttag cacatattca gtggatggtt atgttcacac ctttagtacc tttctggata    9420
acaattgctt atatcatttg tatttccaca aagcatttct attggttctt tagtaattac    9480
ctaaagagac gtgtagtctt taatggtgtt tcctttagta cttttgaaga agctgcgctg    9540
tgcaccttt tgttaaataa agaaatgtat ctaaagttgc gtagtgatgt gctattacct    9600
cttacgcaat ataatagata cttagctctt tataataagt acaagtattt tagtggagca    9660
atggatacaa ctagctacag agaagctgct tgttgtcatc tcgcaaaggc tctcaatgac    9720
ttcagtaact caggttctga tgttctttac caaccaccac aaacctctat cacctcagct    9780
gttttgcaga gtggttttag aaaaatggca ttcccatctg gtaaagttga gggttgtatg    9840
gtacaagtaa cttgtggtac aactacactt aacggtcttt ggcttgatga cgtagtttac    9900
tgtccaagac atgtgatctg cacctctgaa gacatgctta accctaatta tgaagattta    9960
ctcattcgta agtctaatca taattctctg gtacaggctg gtaatgttca actcagggtt   10020
attggacatt ctatgcaaaa ttgtgtactt aagcttaagg ttgatacagc caatcctaag   10080
acacctaagt ataagtttgt tcgcattcaa ccaggacaga cttttttcagt gttagcttgt   10140
tacaatggtt caccatctgg tgtttaccaa tgtgctatga ggcccaattt cactattaag   10200
ggttcattcc ttaatggttc atgtggtagt gttggttttta acatagatta tgactgtgtc   10260
tcttttttgtt acatgcacca tatggaatta ccaactggag ttcatgctgg cacagactta   10320
gaaggtaact tttatggacc ttttgttgac aggcaaacag cacaagcagc tggtacggac   10380
acaactatta cagttaatgt tttagcttgg ttgtacgctg ctgttataaa tggagacagg   10440
tggtttctca atcgatttac cacaactctt aatgacttta accttgtggc tatgaagtac   10500
aattatgaac ctctaacaca agaccatgtt gacatactag gacctctttc tgctcaaact   10560
ggaattgccg ttttagatat gtgtgcttca ttaaaagaat tactgcaaaa tggtatgaat   10620
ggacgtacca tattgggtag tgctttatta gaagatgaat ttacaccttt tgatgttgtt   10680
agacaatgct caggtgttac tttccaaagt gcagtgaaaa gaacaatcaa gggtacacac   10740
cactggttgt tactcacaat tttgacttca cttttagttt tagtccagag tactcaatgg   10800
tctttgttct ttttttgta tgaaaatgcc ttttttacctt ttgctatggg tattattgct   10860
atgtctgctt ttgcaatgat gtttgtcaaa cataagcatg catttctctg tttgttttg   10920
ttaccttctc ttgccactgt agcttatttt aatatggtct atatgcctgc tagttgggtg   10980
atgcgtatta tgacatggtt ggatatggtt gatactagtt tgtctggttt taagctaaaa   11040
```

```
gactgtgtta tgtatgcatc agctgtagtg ttactaatcc ttatgacagc aagaactgtg   11100
tatgatgatg gtgctaggag agtgtggaca cttatgaatg tcttgacact cgtttataaa   11160
gtttattatg gtaatgcttt agatcaagcc atttccatgt gggctcttat aatctctgtt   11220
acttctaact actcaggtgt agttacaact gtcatgtttt tggccagagg tattgttttt   11280
atgtgtgttg agtattgccc tattttcttc ataactggta atacacttca gtgtataatg   11340
ctagtttatt gtttcttagg ctattttgt acttgttact ttggcctctt ttgtttactc   11400
aaccgctact ttagactgac tcttggtgtt tatgattact tagtttctac acaggagttt   11460
agatatatga attcacaggg actactccca cccaagaata gcatagatgc cttcaaactc   11520
aacattaaat tgttgggtgt tggtggcaaa ccttgtatca agtagccac tgtacagtct   11580 aaaatgtcag atgtaaagtg cacatcagta gtcttactct cagttttgca acaactcaga   11640
gtagaatcat catctaaatt gtgggctcaa tgtgtccagt tacacaatga cattctctta   11700
gctaaagata ctactgaagc cttgaaaaa atggtttcac tactttctgt tttgctttcc   11760
atgcagggtg ctgtagacat aaacaagctt tgtgaagaaa tgctggacaa cagggcaacc   11820
ttacaagcta tagcctcaga gtttagttcc cttccatcat atgcagcttt tgctactgct   11880
caagaagctt atgagcaggc tgttgctaat ggtgattctg aagttgttct taaaaagttg   11940
aagaagtctt tgaatgtggc taaatctgaa tttgaccgtg atgcagccat gcaacgtaag   12000
ttggaaaaga tggctgatca agctatgacc caaatgtata acaggctag atctgaggac   12060 aagagggcaa aagttactag tgctatgcag acaatgcttt tcactatgct tagaaagttg   12120
gataatgatg cactcaacaa cattatcaac aatgcaagag atggttgtgt tcccttgaac   12180
ataatacctc ttacaacagc agccaaacta atggttgtca taccagacta taacacatat   12240 aaaatacgt gtgatggtac aacatttact tatgcatcag cattgtggga aatccaacag   12300
gttgtagatg cagatagtaa aattgttcaa cttagtgaaa ttagtatgga caattcacct   12360
aatttagcat ggcctcttat tgtaacagct ttaagggcca attctgctgt caaattacag   12420
aataatgagc ttagtcctgt tgcactacga cagatgtctt gtgctgccgg tactacacaa   12480
actgcttgca ctgatgacaa tgcgttagct tactacaaca caacaaaggg aggtaggttt   12540
gtacttgcac tgttatccga tttacaggat ttgaaatggg ctagattccc taagagtgat   12600
ggaactggta ctatctatac agaactggaa ccaccttgta ggtttgttac agacacacct   12660
aaaggtccta agtgaagta tttatacttt attaaaggat taaacaacct aaatagaggt   12720
atggtacttg gtagtttagc tgccacagta cgtctacaag ctggtaatgc aacagaagtg   12780
cctgccaatt caactgtatt atctttctgt gcttttgctg tagatgctgc taaagcttac   12840
aaagattatc tagctagtgg gggacaacca atcactaatt gtgttaagat gttgtgtaca   12900
cacactggta ctggtcaggc aataacagtt acaccggaag ccaatatgga tcaagaatcc   12960
tttggtggtg catcgtgttg tctgtactgc cgttgccaca tagatcatcc aaatcctaaa   13020
ggattttgtg acttaaaagg taagtatgta caaatacta caacttgtgc taatgaccct   13080
gtgggtttta cacttaaaaa cacagtctgt accgtctgcg gtatgtggaa aggttatggc   13140
tgtagttgtg atcaactccg cgaacccatg cttcagtcag ctgatgcaca atcgttttta   13200
aacgggtttg cggtgtaagt gcagcccgtc ttacaccgtg cggcacaggc actagtactg   13260
atgtcgtata cagggctttt gacatctaca atgataaagt agctggtttt gctaaattcc   13320
taaaaactaa ttgttgtcgc ttccaagaaa aggacgaaga tgacaattta attgattctt   13380
actttgtagt taagagacac actttctcta actaccaaca tgaagaaaca atttataatt   13440
```

```
tacttaagga ttgtccagct gttgctaaac atgacttctt taagtttaga atagacggtg   13500
acatggtacc acatatatca cgtcaacgtc ttactaaata cacaatggca gacctcgtct   13560
atgctttaag gcattttgat gaaggtaatt gtgacacatt aaaagaaata cttgtcacat   13620
acaattgttg tgatgatgat tatttcaata aaaaggactg gtatgatttt gtagaaaacc   13680
cagatatatt acgcgtatac gccaacttag gtgaacgtgt acgccaagct ttgttaaaaa   13740
cagtacaatt ctgtgatgcc atgcgaaatg ctggtattgt tggtgtactg acattagata   13800
atcaagatct caatggtaac tggtatgatt tcggtgattt catacaaacc acgccaggta   13860
gtggagttcc tgttgtagat tcttattatt cattgttaat gcctatatta accttgacca   13920
gggctttaac tgcagagtca catgttgaca ctgacttaac aaagccttac attaagtggg   13980
atttgttaaa atatgacttc acggaagaga ggttaaaaact cttttgaccgt tattttaaat   14040 attgggatca gacataccac ccaaattgtg ttaactgttt ggatgacaga tgcattctgc   14100
attgtgcaaa ctttaatgtt ttattctcta cagtgttccc acctacaagt tttggaccac   14160
tagtgagaaa aatatttgtt gatggtgttc catttgtagt ttcaactgga taccacttca   14220
gagagctagg tgttgtacat aatcaggatg taaacttaca tagctctaga cttagtttta   14280
aggaattact tgtgtatgct gctgaccctg ctatgcacgc tgcttctggt aatctattac   14340
tagataaacg cactacgtgc ttttcagtag ctgcacttac taacaatgtt gcttttcaaa   14400
ctgtcaaacc cggtaatttt aacaaagact tctatgactt tgctgtgtct aagggtttct   14460
ttaaggaagg aagttctgtt gaattaaaac acttcttctt tgctcaggat ggtaatgctg   14520
ctatcagcga ttatgactac tatcgttata atctaccaac aatgtgtgat atcagacaac   14580
tactatttgt agttgaagtt gttgataagt actttgattg ttacgatggt ggctgtatta   14640
atgctaacca agtcatcgtc aacaacctag acaaatcagc tggttttcca tttaataaat   14700
ggggtaaggc tagactttat tatgattcaa tgagttatga ggatcaagat gcacttttcg   14760
catatacaaa acgtaatgtc atccctacta taactcaaat gaatcttaag tatgccatta   14820
gtgcaaagaa tagagctcgc accgtagctg gtgtctctat ctgtagtact atgaccaata   14880
gacagtttca tcaaaaatta ttgaaatcaa tagccgccac tagaggagct actgtagtaa   14940
ttggaacaag caaattctat ggtggttggc acaacatgtt aaaaactgtt tatagtgatg   15000
tagaaaaccc tcaccttatg ggttgggatt atcctaaatg tgatagagcc atgcctaaca   15060
tgcttagaat tatggcctca cttgttcttg ctcgcaaaca tacaacgtgt tgtagcttgt   15120
cacaccgttt ctatagatta gctaatgagt gtgctcaagt attgagtgaa atggtcatgt   15180
gtggcggttc actatatgtt aaaccaggtg gaacctcatc aggagatgcc acaactgctt   15240
atgctaatag tgttttttaac atttgtcaag ctgtcacggc caatgttaat gcactttat   15300 ctactgatgg taacaaaatt gccgataagt atgtccgcaa tttacaacac agactttatg   15360
agtgtctcta tagaaataga gatgttgaca cagactttgt gaatgagttt tacgcatatt   15420
tgcgtaaaca tttctcaatg atgatactct ctgacgatgc tgttgtgtgt ttcaatagca   15480
cttatgcatc tcaaggtcta gtggctagca taaagaactt taagtcagtt ctttattatc   15540
aaaacaatgt ttttatgtct gaagcaaaat gttggactga gactgacctt actaaaggac   15600
ctcatgaatt ttgctctcaa catacaatgc tagttaaaca gggtgatgat tatgtgtacc   15660
ttccttaccc agatccatca agaatcctag gggccggctg ttttgtagat gatatcgtaa   15720
aaacagatgg tacacttatg attgaacggt tcgtgtcttt agctatagat gcttacccac   15780
```

| | | | | |
|---|---|---|---|---|
| ttactaaaca | tcctaatcag | gagtatgctg | atgtctttca | tttgtactta caatacataa | 15840 |
| gaaagctaca | tgatgagtta | acaggacaca | tgttagacat | gtattctgtt atgcttacta | 15900 |
| atgataacac | ttcaaggtat | tgggaacctg | agtttatga | ggctatgtac acaccgcata | 15960 |
| cagtcttaca | ggctgttggg | gcttgtgttc | tttgcaattc | acagacttca ttaagatgtg | 16020 |
| gtgcttgcat | acgtagacca | ttcttatgtt | gtaaatgctg | ttacgaccat gtcatatcaa | 16080 |
| catcacataa | attagtcttg | tctgttaatc | cgtatgtttg | caatgctcca ggttgtgatg | 16140 |
| tcacagatgt | gactcaactt | tacttaggag | gtatgagcta | ttattgtaaa tcacataaac | 16200 |
| cacccattag | ttttccattg | tgtgctaatg | acaagttttt | tggtttatat aaaaatacat | 16260 |
| gtgttggtag | cgataatgtt | actgacttta | atgcaattgc | aacatgtgac tggacaaatg | 16320 |
| ctggtgatta | cattttagct | aacacctgta | ctgaaagact | caagcttttt gcagcagaaa | 16380 |
| cgctcaaagc | tactgaggag | acatttaaac | tgtcttatgg | tattgctact gtacgtgaag | 16440 |
| tgctgtctga | cagagaatta | catctttcat | gggaagttgg | taaacctaga ccaccactta | 16500 |
| accgaaatta | tgtctttact | ggttatcgtg | taactaaaaa | cagtaaagta caaataggag | 16560 |
| agtacacctt | tgaaaaaggt | gactatggtg | atgctgttgt | ttaccgaggt acaacaactt | 16620 |
| acaaattaaa | tgttggtgat | tattttgtgc | tgacatcaca | tacagtaatg ccattaagtg | 16680 |
| cacctacact | agtgccacaa | gagcactatg | ttagaattac | tggcttatac ccaacactca | 16740 |
| atatctcaga | tgagttttct | agcaatgttg | caaattatca | aaaggttggt atgcaaaagt | 16800 |
| attctacact | ccagggacca | cctggtactg | gtaagagtca | ttttgctatt ggcctagctc | 16860 |
| tctactaccc | ttctgctcgc | atagtgtata | cagcttgctc | tcatgccgct gttgatgcac | 16920 |
| tatgtgagaa | ggcattaaaa | tatttgccta | tagataaatg | tagtagaatt atacctgcac | 16980 |
| gtgctcgtgt | agagtgtttt | gataaattca | aagtgaattc | aacattagaa cagtatgtct | 17040 |
| tttgtactgt | aaatgcattg | cctgagacga | cagcagatat | agttgtcttt gatgaaattt | 17100 |
| caatggccac | aaattatgat | ttgagtgttg | tcaatgccag | attacgtgct aagcactatg | 17160 |
| tgtacattgg | cgaccctgct | caattacctg | caccacgcac | attgctaact aagggcacac | 17220 |
| tagaaccaga | atatttcaat | tcagtgtgta | gacttatgaa | aactataggt ccagacatgt | 17280 |
| tcctcggaac | ttgtcggcgt | tgtcctgctg | aaattgttga | cactgtgagt gctttggttt | 17340 |
| atgataataa | gctaaagca | cataaagaca | atcagctca | atgctttaaa atgttttata | 17400 |
| agggtgttat | cacgcatgat | gtttcatctg | caattaacag | gccacaaata ggcgtggtaa | 17460 |
| gagaattcct | tacacgtaac | cctgcttgga | gaaaagctgt | cttatttca ccttataatt | 17520 |
| cacagaatgc | tgtagcctca | aagattttgg | gactaccaac | tcaaactgtt gattcatcac | 17580 |
| agggctcaga | atatgactat | gtcatattca | ctcaaaccac | tgaaacagct cactcttgta | 17640 |
| atgtaaacag | atttaatgtt | gctattacca | gagcaaaagt | aggcatactt tgcataatgt | 17700 |
| ctgatagaga | cctttatgac | aagttgcaat | ttacaagtct | tgaaattcca cgtaggaatg | 17760 |
| tggcaacttt | acaagctgaa | aatgtaacag | gactctttaa | agattgtagt aaggtaatca | 17820 |
| ctgggttaca | tcctacacag | gcacctacac | acctcagtgt | tgacactaaa ttcaaaactg | 17880 |
| aaggtttatg | tgttgacata | cctggcatac | ctaaggacat | gacctataga agactcatct | 17940 |
| ctatgatggg | ttttaaaatg | aattatcaag | ttaatggtta | ccctaacatg tttatcaccc | 18000 |
| gcgaagaagc | tataagacat | gtacgtgcat | ggattggctt | cgatgtcgag gggtgtcatg | 18060 |
| ctactagaga | agctgttggt | accaatttac | ctttacagct | aggttttcct acaggtgtta | 18120 |
| acctagttgc | tgtacctaca | ggttatgttg | atacacctaa | taatacagat ttttccagag | 18180 |

```
ttagtgctaa accaccgcct ggagatcaat ttaaacacct cataccactt atgtacaaag    18240
gacttccttg gaatgtagtg cgtataaaga ttgtacaaat gttaagtgac acacttaaaa    18300
atctctctga cagagtcgta tttgtcttat gggcacatgg ctttgagttg acatctatga    18360
agtattttgt gaaaatagga cctgagcgca cctgttgtct atgtgataga cgtgccacat    18420
gcttttccac tgcttcagac acttatgcct gttggcatca ttctattgga tttgattacg    18480
tctataatcc gtttatgatt gatgttcaac aatggggttt tacaggtaac ctacaaagca    18540
accatgatct gtattgtcaa gtccatggta atgcacatgt agctagttgt gatgcaatca    18600
tgactaggtg tctagctgtc cacgagtgct tgttaagcg tgttgactgg actattgaat    18660
atcctataat tggtgatgaa ctgaagatta atgcggcttg tagaaaggtt caacacatgg    18720
ttgttaaagc tgcattatta gcagacaaat tcccagttct tcacgacatt ggtaaccta    18780
aagctattaa gtgtgtacct caagctgatg tagaatggaa gttctatgat gcacagcctt    18840
gtagtgacaa agcttataaa atagaagaat tattctattc ttatgccaca cattctgaca    18900
aattcacaga tggtgtatgc ctattttgga attgcaatgt cgatagatat cctgctaatt    18960
ccattgtttg tagatttgac actagagtgc tatctaacct taacttgcct ggttgtgatg    19020
gtggcagttt gtatgtaaat aaacatgcat tccacacacc agcttttgat aaaagtgctt    19080
ttgttaattt aaaacaatta ccattttct attactctga cagtccatgt gagtctcatg    19140
gaaaacaagt agtgtcagat atagattatg taccactaaa gtctgctacg tgtataacac    19200
gttgcaattt aggtggtgct gtctgtagac atcatgctaa tgagtacaga ttgtatctcg    19260
atgcttataa catgatgatc tcagctggct ttagcttgtg ggtttacaaa caatttgata    19320
cttataacct ctggaacact tttacaagac ttcagagttt agaaaatgtg gcttttaatg    19380
ttgtaaataa gggacacttt gatggacaac agggtgaagt accagtttct atcattaata    19440
acactgttta cacaaaagtt gatggtgttg atgtagaatt gtttgaaaat aaaacaacat    19500
tacctgttaa tgtagcattt gagctttggg ctaagcgcaa cattaaacca gtaccagagg    19560
tgaaaatact caataatttg ggtgtggaca ttgctgctaa tactgtgatc tgggactaca    19620
aaagagatgc tccagcacat atatctacta ttggtgtttg ttctatgact gacatagcca    19680
agaaaccaac tgaaacgatt tgtgcaccac tcactgtctt ttttgatggt agagttgatg    19740
gtcaagtaga cttatttaga aatgcccgta atggtgttct tattacagaa ggtagtgtta    19800
aaggtttaca accatctgta ggtcccaaac aagctagtct taatggagtc acattaattg    19860
gagaagccgt aaaaacacag ttcaattatt ataagaaagt tgatggtgtt gtccaacaat    19920
tacctgaaac ttactttact cagagtagaa atttacaaga atttaaaccc aggagtcaaa    19980
tggaaattga tttcttagaa ttagctatgg atgaattcat tgaacggtat aaattagaag    20040
gctatgcctt cgaacatatc gtttatggag attttagtca tagtcagtta ggtggtttac    20100
atctactgat tggactagct aaacgtttta aggaatcacc ttttgaatta gaagatttta    20160
ttcctatgga cagtacagtt aaaaactatt tcataacaga tgcgcaaaca ggttcatcta    20220
agtgtgtgtg ttctgttatt gatttattac ttgatgattt tgttgaaata ataaaatccc    20280
aagatttatc tgtagtttct aaggttgtca agtgactat tgactataca gaaatttcat    20340
ttatgctttg gtgtaaagat ggccatgtag aaacatttta cccaaaatta caatctagtc    20400
aagcgtggca accgggtgtt gctatgccta atctttacaa aatgcaaaga atgctattag    20460
aaaagtgtga ccttcaaaat tatggtgata gtgcaacatt acctaaaggc ataatgatga    20520
```

-continued

```
atgtcgcaaa atatactcaa ctgtgtcaat atttaaacac attaacatta gctgtaccct    20580
ataatatgag agttatacat tttggtgctg gttctgataa aggagttgca ccaggtacag    20640
ctgttttaag acagtggttg cctacgggta cgctgcttgt cgattcagat cttaatgact    20700
ttgtctctga tgcagattca actttgattg gtgattgtgc aactgtacat acagctaata    20760
aatgggatct cattattagt gatatgtacg accctaagac taaaaatgtt acaaaagaaa    20820
atgactctaa agagggtttt ttcacttaca tttgtgggtt tatacaacaa aagctagctc    20880
ttggaggttc cgtggctata aagataacag aacattcttg gaatgctgat ctttataagc    20940
tcatgggaca cttcgcatgg tggacagcct ttgttactaa tgtgaatgcg tcatcatctg    21000
aagcattttt aattggatgt aattatcttg gcaaaccacg cgaacaaata gatggttatg    21060
tcatgcatgc aaattacata ttttggagga atacaaatcc aattcagttg tcttcctatt    21120
ctttatttga catgagtaaa tttcccctta aattaagggg tactgctgtt atgtctttaa    21180
aagaaggtca aatcaatgat atgattttat ctcttcttag taaaggtaga cttataatta    21240
gagaaaacaa cagagttgtt atttctagtg atgttcttgt taacaactaa                21290
```

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 11

```
ttttttttt ttttttt                                                        18
```